(12) United States Patent
Gregersen

(10) Patent No.: US 8,292,841 B2
(45) Date of Patent: Oct. 23, 2012

(54) SOLID-BODY CATHETER INCLUDING LATERAL DISTAL OPENINGS

(75) Inventor: Colin S. Gregersen, Salt Lake City, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 505 days.

(21) Appl. No.: 12/414,467

(22) Filed: Mar. 30, 2009

(65) Prior Publication Data

US 2009/0192435 A1  Jul. 30, 2009

Related U.S. Application Data

(63) Continuation-in-part of application No. 12/253,870, filed on Oct. 17, 2008, now Pat. No. 8,066,660.

(60) Provisional application No. 60/983,032, filed on Oct. 26, 2007, provisional application No. 61/036,848, filed on Mar. 14, 2008, provisional application No. 61/085,748, filed on Aug. 1, 2008.

(51) Int. Cl.
*A61M 37/00* (2006.01)
*A61M 1/00* (2006.01)
*A61M 31/00* (2006.01)

(52) U.S. Cl. ................... 604/29; 604/508; 604/6.16

(58) Field of Classification Search .............. 604/28, 604/29, 43, 93.01, 94.01
See application file for complete search history.

(56) References Cited

U.S. PATENT DOCUMENTS

| | | | |
|---|---|---|---|
| 701,075 A | 5/1902 | McCully | |
| 1,696,018 A | 12/1928 | Scheliberg | |
| 1,856,811 A | 7/1931 | Inaki | |
| 2,024,982 A | 12/1935 | Scott | |
| 2,173,527 A | 9/1939 | Agayoff | |
| 2,286,462 A | 6/1942 | Chaffin | |
| 2,393,002 A | 1/1946 | Smith | |
| 2,910,981 A | 11/1959 | Wilson et al. | |

(Continued)

FOREIGN PATENT DOCUMENTS

BE  834211  2/1976

(Continued)

OTHER PUBLICATIONS

Camp, "Care of the Groshong Catheter", Oncol Nurs Forum, vol. 15, No. 6, 1988.

(Continued)

*Primary Examiner* — Kevin C Sirmons
*Assistant Examiner* — Andrew Gilbert
(74) *Attorney, Agent, or Firm* — Rutan & Tucker, LLP

(57) ABSTRACT

A split-tip catheter for placement within the vasculature of a patient and for use in hemodialysis or other suitable procedures is disclosed. In one embodiment, the split-tip catheter includes a catheter body that defines a first lumen and a second lumen. The catheter body further comprises a split distal region, including a venous segment and an arterial segment. The venous segment includes a recess extending proximally of a nose portion; and a lateral opening in fluid communication with the first lumen. The arterial segment also includes a lateral opening, is separate from the venous segment, and is removably seatable in the recess provided by the venous segment. In one embodiment, the distal region is un-split, but includes symmetrically opposed lateral openings, as well as distal openings, in communication with the first and second lumens for providing a functional stagger for blood flow in both forward and reverse catheter flow directions.

20 Claims, 47 Drawing Sheets

U.S. PATENT DOCUMENTS

| | | |
|---|---|---|
| 3,144,868 A | 8/1964 | Jascalevich |
| 3,176,690 A | 4/1965 | H'Doubler |
| 3,256,885 A | 6/1966 | Higgins et al. |
| 3,416,532 A | 12/1968 | Grossman |
| 3,426,759 A | 2/1969 | Smith |
| 3,460,255 A | 8/1969 | Hutson |
| D217,795 S | 6/1970 | Spaven |
| 3,612,038 A | 10/1971 | Halligan |
| 3,736,939 A | 6/1973 | Taylor |
| 3,805,794 A | 4/1974 | Schlesinger |
| 3,812,851 A | 5/1974 | Rodriguez |
| 3,848,604 A | 11/1974 | Sackner |
| 3,890,977 A | 6/1975 | Wilson |
| 3,929,126 A | 12/1975 | Corsaut |
| 3,935,857 A | 2/1976 | Co |
| 3,995,623 A | 12/1976 | Blake et al. |
| 4,068,659 A | 1/1978 | Moorehead |
| 4,072,146 A | 2/1978 | Howes |
| 4,072,153 A | 2/1978 | Swartz |
| 4,098,275 A | 7/1978 | Consalvo |
| 4,114,625 A | 9/1978 | Onat |
| 4,117,836 A | 10/1978 | Erikson |
| 4,129,129 A | 12/1978 | Amrine |
| 4,134,402 A | 1/1979 | Mahurkar |
| 4,149,535 A | 4/1979 | Volder |
| 4,180,068 A | 12/1979 | Jacobsen et al. |
| 4,248,224 A | 2/1981 | Jones |
| 4,276,880 A | 7/1981 | Malmin |
| 4,292,976 A | 10/1981 | Banka |
| 4,299,228 A | 11/1981 | Peters |
| 4,300,550 A | 11/1981 | Gandi et al. |
| 4,309,994 A | 1/1982 | Grunwald |
| 4,327,722 A | 5/1982 | Groshong et al. |
| 4,385,631 A | 5/1983 | Uthmann et al. |
| 4,392,855 A | 7/1983 | Oreopoulos et al. |
| 4,403,983 A | 9/1983 | Edelman et al. |
| 4,405,313 A | 9/1983 | Sisley et al. |
| 4,406,656 A | 9/1983 | Hattler et al. |
| D272,651 S | 2/1984 | Mahurkar |
| 4,431,426 A | 2/1984 | Groshong et al. |
| 4,432,722 A | 2/1984 | Bohan, Jr. et al. |
| 4,432,752 A | 2/1984 | Marlon |
| 4,445,893 A | 5/1984 | Bodicky |
| 4,451,252 A | 5/1984 | Martin et al. |
| 4,453,928 A | 6/1984 | Steiger |
| 4,465,482 A | 8/1984 | Tittel et al. |
| 4,490,138 A | 12/1984 | Lipsky et al. |
| 4,493,696 A | 1/1985 | Uldall et al. |
| RE31,873 E | 4/1985 | Howes |
| 4,531,933 A | 7/1985 | Norton et al. |
| 4,543,087 A | 9/1985 | Sommercorn et al. |
| 4,545,373 A | 10/1985 | Christoudias |
| 4,557,261 A | 12/1985 | Rugheimer et al. |
| 4,568,329 A | 2/1986 | Mahurkar |
| 4,568,338 A | 2/1986 | Todd |
| 4,573,476 A | 3/1986 | Ruiz |
| 4,581,012 A | 4/1986 | Brown et al. |
| 4,583,968 A | 4/1986 | Mahurkar |
| 4,583,986 A | 4/1986 | Lapidus |
| 4,601,697 A | 7/1986 | Mammolenti et al. |
| 4,619,643 A | 10/1986 | Bai |
| 4,623,327 A | 11/1986 | Mahurkar |
| 4,626,240 A | 12/1986 | Edelman et al. |
| 4,642,101 A | 2/1987 | Krolikowski et al. |
| 4,643,711 A | 2/1987 | Bates |
| 4,666,426 A | 5/1987 | Aigner et al. |
| 4,668,221 A | 5/1987 | Luther |
| 4,670,009 A | 6/1987 | Bullock |
| 4,675,004 A | 6/1987 | Hadford et al. |
| 4,681,122 A | 7/1987 | Winters et al. |
| 4,681,564 A | 7/1987 | Landreneau |
| 4,681,570 A | 7/1987 | Dalton |
| 4,682,978 A | 7/1987 | Martin et al. |
| 4,687,471 A | 8/1987 | Twardowski et al. |
| 4,692,141 A | 9/1987 | Mahurkar |
| 4,694,838 A | 9/1987 | Wijayarthna et al. |
| 4,701,159 A | 10/1987 | Brown et al. |
| 4,702,917 A | 10/1987 | Schindler |
| 4,713,171 A | 12/1987 | Polaschegg |
| 4,717,379 A | 1/1988 | Ekholmer et al. |
| 4,735,620 A | 4/1988 | Ruiz |
| 4,737,141 A | 4/1988 | Spits et al. |
| 4,737,152 A | 4/1988 | Alchas |
| 4,738,667 A | 4/1988 | Galloway |
| 4,748,808 A | 6/1988 | Hill |
| 4,755,176 A | 7/1988 | Patel |
| 4,769,016 A | 9/1988 | Labianca et al. |
| 4,770,652 A | 9/1988 | Mahurkar |
| 4,772,268 A | 9/1988 | Bates |
| 4,772,269 A | 9/1988 | Twardowski et al. |
| 4,776,841 A | 10/1988 | Catalano |
| 4,777,951 A | 10/1988 | Cribier et al. |
| 4,784,638 A * | 11/1988 | Ghajar et al. ............. 604/523 |
| 4,790,809 A | 12/1988 | Kuntz |
| 4,795,439 A | 1/1989 | Guest |
| 4,801,297 A | 1/1989 | Mueller |
| 4,804,359 A | 2/1989 | Grunwald et al. |
| 4,808,155 A | 2/1989 | Mahurkar |
| 4,808,163 A | 2/1989 | Laub |
| 4,809,710 A | 3/1989 | Williamson |
| 4,820,265 A | 4/1989 | DeSatnick et al. |
| 4,832,687 A | 5/1989 | Smith, III |
| 4,834,709 A | 5/1989 | Banning et al. |
| 4,842,582 A | 6/1989 | Mahurkar |
| 4,842,592 A | 6/1989 | Caggiani et al. |
| 4,846,814 A | 7/1989 | Ruiz |
| 4,863,441 A | 9/1989 | Lindsay et al. |
| 4,867,742 A | 9/1989 | Calderon |
| 4,892,518 A | 1/1990 | Cupp et al. |
| 4,894,057 A | 1/1990 | Howes |
| 4,895,561 A | 1/1990 | Mahurkar |
| 4,898,591 A | 2/1990 | Jang et al. |
| 4,906,238 A | 3/1990 | Greenfeld et al. |
| 4,925,452 A | 5/1990 | Melinyshyn et al. |
| 4,927,418 A | 5/1990 | Dake et al. |
| 4,935,004 A | 6/1990 | Cruz |
| 4,935,010 A | 6/1990 | Cox et al. |
| 4,935,044 A | 6/1990 | Schoenpflug et al. |
| 4,936,826 A | 6/1990 | Amarasinghe |
| 4,950,232 A | 8/1990 | Ruzicka et al. |
| 4,950,259 A | 8/1990 | Geary et al. |
| 4,951,665 A | 8/1990 | Schneider |
| 4,961,729 A | 10/1990 | Vaillancourt |
| 4,961,731 A | 10/1990 | Bodicky et al. |
| 4,961,809 A | 10/1990 | Martin et al. |
| 4,968,307 A | 11/1990 | Dake et al. |
| 4,969,890 A | 11/1990 | Sugita et al. |
| 4,981,477 A | 1/1991 | Schon et al. |
| 4,985,014 A | 1/1991 | Orejola |
| 4,990,138 A | 2/1991 | Bacich et al. |
| 4,994,027 A | 2/1991 | Farrell |
| 4,995,865 A | 2/1991 | Gahara et al. |
| 5,009,636 A | 4/1991 | Wortley et al. |
| 5,015,230 A | 5/1991 | Martin et al. |
| 5,016,640 A | 5/1991 | Ruiz |
| 5,021,044 A | 6/1991 | Sharkawy |
| 5,041,101 A | 8/1991 | Seder et al. |
| 5,041,107 A | 8/1991 | Heil, Jr. |
| 5,049,138 A | 9/1991 | Chevalier et al. |
| 5,053,003 A | 10/1991 | Dadson et al. |
| 5,053,004 A | 10/1991 | Markel et al. |
| 5,053,023 A | 10/1991 | Martin |
| 5,057,073 A | 10/1991 | Martin |
| 5,059,170 A | 10/1991 | Cameron |
| 5,069,673 A | 12/1991 | Shwab |
| 5,074,841 A | 12/1991 | Ademovic et al. |
| 5,084,013 A | 1/1992 | Takase et al. |
| 5,098,412 A | 3/1992 | Shiu et al. |
| 5,100,395 A | 3/1992 | Rosenberg et al. |
| 5,102,402 A | 4/1992 | Dror et al. |
| 5,106,368 A | 4/1992 | Uldall et al. |
| 5,106,376 A | 4/1992 | Mononen et al. |
| 5,111,829 A | 5/1992 | Alvarez de Toledo |
| 5,112,301 A | 5/1992 | Fenton, Jr. et al. |
| 5,114,423 A | 5/1992 | Kasprzyk et al. |
| 5,117,836 A | 6/1992 | Millar |
| 5,120,299 A | 6/1992 | Lombardi |

| Patent | Date | Inventor |
|---|---|---|
| 5,120,304 A | 6/1992 | Sasaki |
| 5,122,125 A | 6/1992 | Deuss et al. |
| 5,125,904 A | 6/1992 | Lee |
| 5,129,891 A | 7/1992 | Young |
| 5,135,599 A | 8/1992 | Martin et al. |
| 5,139,486 A | 8/1992 | Moss |
| 5,156,592 A | 10/1992 | Martin et al. |
| 5,163,928 A | 11/1992 | Hobbs et al. |
| 5,167,623 A | 12/1992 | Cianci et al. |
| 5,171,216 A | 12/1992 | Dasse et al. |
| 5,171,227 A | 12/1992 | Twardowski et al. |
| 5,178,616 A | 1/1993 | Uemiya et al. |
| 5,188,592 A | 2/1993 | Hakki |
| 5,188,593 A | 2/1993 | Martin |
| 5,190,520 A | 3/1993 | Fenton, Jr. et al. |
| 5,190,529 A | 3/1993 | McCrory et al. |
| 5,191,898 A | 3/1993 | Millar |
| 5,195,962 A | 3/1993 | Martin et al. |
| 5,197,951 A | 3/1993 | Mahurkar |
| 5,197,973 A | 3/1993 | Pang et al. |
| 5,197,976 A | 3/1993 | Herweck et al. |
| 5,201,723 A | 4/1993 | Quinn |
| 5,207,648 A | 5/1993 | Gross |
| 5,207,650 A | 5/1993 | Martin |
| 5,209,723 A | 5/1993 | Twardowski et al. |
| 5,209,725 A | 5/1993 | Roth |
| 5,209,742 A | 5/1993 | Venema et al. |
| 5,211,256 A | 5/1993 | Muramatsu et al. |
| 5,215,527 A | 6/1993 | Beck et al. |
| 5,221,255 A | 6/1993 | Mahurkar et al. |
| 5,221,256 A | 6/1993 | Mahurkar |
| 5,222,949 A | 6/1993 | Kaldany |
| 5,226,880 A | 7/1993 | Martin et al. |
| 5,234,438 A | 8/1993 | Semrad |
| 5,236,016 A | 8/1993 | Vogelsang et al. |
| 5,242,398 A | 9/1993 | Knoll et al. |
| 5,246,430 A | 9/1993 | MacFarlane |
| 5,250,034 A | 10/1993 | Appling et al. |
| 5,254,084 A | 10/1993 | Geary |
| 5,273,527 A | 12/1993 | Schatz et al. |
| 5,273,534 A | 12/1993 | Knoepfler |
| 5,279,596 A | 1/1994 | Castaneda et al. |
| 5,279,599 A | 1/1994 | Wilk |
| 5,306,240 A | 4/1994 | Berry |
| 5,312,337 A | 5/1994 | Flaherty et al. |
| 5,312,357 A | 5/1994 | Buijs et al. |
| 5,318,517 A | 6/1994 | Reiman |
| 5,322,519 A | 6/1994 | Ash |
| 5,324,274 A | 6/1994 | Martin |
| 5,338,308 A | 8/1994 | Wilk |
| 5,342,295 A | 8/1994 | Imran |
| 5,342,386 A | 8/1994 | Trotta |
| 5,346,471 A | 9/1994 | Raulerson |
| 5,348,536 A | 9/1994 | Young et al. |
| 5,350,358 A | 9/1994 | Martin |
| 5,360,397 A | 11/1994 | Pinchuk |
| 5,360,407 A | 11/1994 | Leonard et al. |
| 5,364,344 A | 11/1994 | Beattie et al. |
| 5,374,245 A * | 12/1994 | Mahurkar ........................ 604/43 |
| 5,378,230 A | 1/1995 | Mahurkar |
| 5,380,276 A | 1/1995 | Miller et al. |
| 5,380,290 A | 1/1995 | Makower et al. |
| 5,382,238 A | 1/1995 | Abrahamson et al. |
| 5,389,087 A | 2/1995 | Miraki |
| 5,389,090 A | 2/1995 | Fischell et al. |
| 5,395,316 A * | 3/1995 | Martin ........................... 604/43 |
| 5,399,168 A | 3/1995 | Wadsworth, Jr. et al. |
| 5,403,291 A * | 4/1995 | Abrahamson ................ 604/523 |
| 5,405,320 A | 4/1995 | Twardowski et al. |
| 5,405,341 A | 4/1995 | Martin |
| 5,409,463 A | 4/1995 | Thomas et al. |
| 5,417,668 A | 5/1995 | Setzer et al. |
| 5,423,768 A | 6/1995 | Folden et al. |
| 5,431,661 A | 7/1995 | Koch |
| 5,451,026 A | 9/1995 | Smith |
| 5,451,206 A | 9/1995 | Young |
| 5,451,233 A | 9/1995 | Yock |
| 5,458,570 A | 10/1995 | May, Jr. |
| 5,458,582 A | 10/1995 | Nakao |
| 5,472,417 A | 12/1995 | Martin et al. |
| 5,472,432 A | 12/1995 | Martin |
| 5,476,453 A | 12/1995 | Mehta |
| 5,480,380 A | 1/1996 | Martin |
| 5,486,159 A | 1/1996 | Mahurkar |
| 5,489,278 A | 2/1996 | Abrahamson |
| 5,496,292 A | 3/1996 | Burnham |
| 5,505,710 A | 4/1996 | Dorsey, III |
| 5,507,723 A | 4/1996 | Keshaviah |
| 5,509,897 A | 4/1996 | Twardowski et al. |
| 5,509,900 A | 4/1996 | Kirkman |
| 5,509,902 A | 4/1996 | Raulerson |
| 5,542,925 A | 8/1996 | Orth |
| 5,545,373 A | 8/1996 | Maziasz et al. |
| 5,556,390 A | 9/1996 | Hicks |
| 5,556,930 A | 9/1996 | Brehm et al. |
| 5,558,635 A | 9/1996 | Cannon |
| 5,562,609 A | 10/1996 | Brumbach |
| 5,569,182 A | 10/1996 | Twardowski et al. |
| 5,569,195 A | 10/1996 | Saab |
| 5,571,093 A | 11/1996 | Cruz et al. |
| 5,584,803 A | 12/1996 | Stevens et al. |
| 5,599,304 A | 2/1997 | Shaari |
| 5,599,328 A | 2/1997 | Stevens |
| 5,607,462 A | 3/1997 | Imran |
| 5,624,392 A | 4/1997 | Saab |
| 5,624,413 A | 4/1997 | Markel et al. |
| 5,632,729 A | 5/1997 | Cai et al. |
| 5,637,102 A | 6/1997 | Tolkoff et al. |
| 5,642,270 A | 6/1997 | Green et al. |
| 5,655,867 A | 8/1997 | Gysi et al. |
| 5,662,606 A | 9/1997 | Cimino et al. |
| 5,665,067 A | 9/1997 | Linder et al. |
| 5,685,467 A | 11/1997 | Niemi et al. |
| 5,685,867 A | 11/1997 | Twardowski et al. |
| 5,686,867 A | 11/1997 | Sutardja et al. |
| 5,693,030 A | 12/1997 | Lee et al. |
| 5,695,457 A | 12/1997 | St. Goar et al. |
| 5,704,915 A | 1/1998 | Melsky et al. |
| 5,713,849 A | 2/1998 | Bosma et al. |
| 5,713,853 A | 2/1998 | Clark et al. |
| 5,717,216 A | 2/1998 | McCoy et al. |
| 5,718,678 A | 2/1998 | Fleming, III |
| 5,718,692 A | 2/1998 | Schon et al. |
| 5,720,735 A | 2/1998 | Dorros |
| 5,738,649 A | 4/1998 | Macoviak |
| 5,741,329 A | 4/1998 | Agrawal et al. |
| 5,743,873 A | 4/1998 | Cai et al. |
| 5,752,939 A | 5/1998 | Makoto et al. |
| 5,769,796 A | 6/1998 | Palermo et al. |
| 5,772,643 A | 6/1998 | Howell et al. |
| 5,776,096 A | 7/1998 | Fields |
| 5,776,111 A | 7/1998 | Tesio |
| 5,785,686 A | 7/1998 | Runge |
| 5,792,094 A | 8/1998 | Stevens et al. |
| 5,792,123 A | 8/1998 | Ensminger |
| 5,797,869 A | 8/1998 | Martin et al. |
| 5,800,384 A | 9/1998 | Russell et al. |
| 5,800,414 A | 9/1998 | Cazal et al. |
| 5,800,516 A | 9/1998 | Fine et al. |
| 5,807,311 A | 9/1998 | Palestrant |
| 5,807,318 A | 9/1998 | St. Goar et al. |
| 5,807,329 A | 9/1998 | Gelman |
| 5,809,897 A | 9/1998 | Powell et al. |
| 5,810,789 A | 9/1998 | Powers et al. |
| 5,814,016 A | 9/1998 | Valley et al. |
| 5,830,184 A | 11/1998 | Basta |
| 5,830,196 A | 11/1998 | Hicks |
| 5,833,671 A | 11/1998 | Macoviak et al. |
| 5,858,009 A | 1/1999 | Jonkman |
| 5,861,010 A | 1/1999 | Boussignac et al. |
| 5,868,717 A | 2/1999 | Prosl |
| 5,873,865 A | 2/1999 | Horzewski et al. |
| 5,876,366 A | 3/1999 | Dykstra et al. |
| 5,876,426 A | 3/1999 | Kume et al. |
| 5,882,347 A | 3/1999 | Mouris-Laan et al. |
| 5,891,111 A | 4/1999 | Ismael et al. |
| 5,904,670 A | 5/1999 | Schreiner |
| 5,911,715 A | 6/1999 | Berg et al. |

| | | | | | | |
|---|---|---|---|---|---|---|
| 5,913,848 | A | 6/1999 | Luther et al. | 6,585,705 B1 | 7/2003 | Maginot et al. |
| 5,916,208 | A | 6/1999 | Luther et al. | 6,592,565 B2 | 7/2003 | Twardowski |
| 5,919,160 | A | 7/1999 | Sanfilippo, II | 6,595,966 B2 | 7/2003 | Davey et al. |
| 5,944,732 | A | 8/1999 | Raulerson et al. | 6,620,118 B1 | 9/2003 | Prosl et al. |
| 5,947,937 | A | 9/1999 | Urrutia et al. | 6,638,242 B2 | 10/2003 | Wilson et al. |
| 5,947,953 | A | 9/1999 | Ash et al. | 6,659,134 B2 | 12/2003 | Navis |
| 5,957,879 | A | 9/1999 | Roberts et al. | 6,682,498 B2 | 1/2004 | Ross |
| 5,957,893 | A | 9/1999 | Luther et al. | 6,682,519 B1 | 1/2004 | Schon |
| 5,957,912 | A | 9/1999 | Heitzmann | 6,695,832 B2 | 2/2004 | Schon et al. |
| 5,961,486 | A | 10/1999 | Twardowski et al. | 6,702,776 B2 | 3/2004 | Quinn |
| 5,964,796 | A | 10/1999 | Imran | 6,712,797 B1 | 3/2004 | Southern, Jr. |
| 5,976,103 | A | 11/1999 | Martin | 6,712,798 B2 | 3/2004 | Constantz |
| 5,976,120 | A | 11/1999 | Chow et al. | 6,719,717 B1 | 4/2004 | Johnson et al. |
| 5,980,551 | A | 11/1999 | Summers et al. | 6,719,749 B1 | 4/2004 | Schweikert et al. |
| 5,984,908 | A | 11/1999 | Davis et al. | 6,723,084 B1 | 4/2004 | Maginot et al. |
| 5,989,206 | A | 11/1999 | Prosl et al. | 6,723,114 B1 | 4/2004 | Shalaby |
| 5,989,213 | A | 11/1999 | Maginot | 6,730,299 B1 | 5/2004 | Tayot et al. |
| 6,001,079 | A | 12/1999 | Pourchez | 6,752,827 B2 | 6/2004 | Ross et al. |
| 6,033,382 | A | 3/2000 | Basta | 6,755,851 B2 | 6/2004 | Noda et al. |
| 6,036,654 | A | 3/2000 | Quinn et al. | 6,758,836 B2 | 7/2004 | Zawacki |
| 6,059,771 | A | 5/2000 | Balbierz et al. | 6,786,664 B2 | 9/2004 | Claramunt et al. |
| 6,074,374 | A | 6/2000 | Fulton | 6,786,884 B1 | 9/2004 | DeCant, Jr. et al. |
| 6,086,555 | A | 7/2000 | Eliasen et al. | 6,796,991 B2 | 9/2004 | Nardeo |
| 6,090,096 | A | 7/2000 | St. Goar et al. | 6,797,107 B1 | 9/2004 | Kotzey |
| 6,099,513 | A | 8/2000 | Spehalski | 6,808,510 B1 | 10/2004 | DiFiore |
| 6,103,778 | A | 8/2000 | Hyon et al. | 6,814,718 B2 | 11/2004 | McGuckin, Jr. et al. |
| 6,106,540 | A | 8/2000 | White et al. | 6,819,951 B2 | 11/2004 | Patel et al. |
| 6,113,572 | A | 9/2000 | Gailey et al. | 6,821,287 B1 | 11/2004 | Jang |
| 6,117,117 | A | 9/2000 | Mauch | 6,824,554 B1 | 11/2004 | Jang |
| 6,120,494 | A | 9/2000 | Jonkman | 6,835,452 B1 | 12/2004 | Hamerski |
| 6,126,631 | A | 10/2000 | Loggie | 6,837,864 B1 | 1/2005 | Bertolero et al. |
| 6,146,354 | A | 11/2000 | Beil | 6,852,079 B2 | 2/2005 | Miyano et al. |
| 6,146,373 | A | 11/2000 | Cragg et al. | 6,852,097 B1 | 2/2005 | Fulton, III |
| 6,152,909 | A | 11/2000 | Bagaoisan et al. | 6,858,019 B2 | 2/2005 | McGuckin, Jr. et al. |
| 6,156,016 | A | 12/2000 | Maginot | 6,872,198 B1 | 3/2005 | Wilson et al. |
| 6,161,547 | A | 12/2000 | Barbut | 6,878,143 B2 * | 4/2005 | Andersen ................ 604/270 |
| 6,178,356 | B1 | 1/2001 | Chastain et al. | 6,881,211 B2 | 4/2005 | Schweikert et al. |
| 6,180,059 | B1 | 1/2001 | Divino, Jr. et al. | 6,911,014 B2 | 6/2005 | Wentling et al. |
| 6,190,349 | B1 | 2/2001 | Ash et al. | 6,913,601 B2 | 7/2005 | St. Goar et al. |
| 6,190,371 | B1 | 2/2001 | Maginot et al. | 6,916,313 B2 | 7/2005 | Cunningham |
| 6,193,685 | B1 | 2/2001 | Goodin | 6,921,396 B1 | 7/2005 | Wilson et al. |
| 6,196,996 | B1 | 3/2001 | Teirstein | 6,921,411 B2 | 7/2005 | Yock |
| 6,206,849 | B1 | 3/2001 | Martin et al. | 6,934,142 B2 | 8/2005 | Grosse et al. |
| 6,210,365 | B1 | 4/2001 | Afzal | 6,966,886 B2 | 11/2005 | Appling |
| 6,210,380 | B1 | 4/2001 | Mauch | 6,969,381 B2 | 11/2005 | Voorhees |
| 6,217,527 | B1 | 4/2001 | Selmon et al. | 6,991,625 B1 * | 1/2006 | Gately et al. ................ 604/523 |
| 6,224,622 | B1 | 5/2001 | Kotzev | D515,211 S | 2/2006 | Chesnin |
| 6,238,406 | B1 | 5/2001 | Ellis et al. | 6,997,894 B2 | 2/2006 | Caresio |
| 6,264,627 | B1 | 7/2001 | Liska et al. | 7,008,395 B1 | 3/2006 | Loggie |
| 6,273,879 | B1 | 8/2001 | Keith et al. | 7,011,645 B2 | 3/2006 | McGuckin, Jr. et al. |
| 6,280,423 | B1 | 8/2001 | Davey et al. | 7,018,384 B2 | 3/2006 | Skakoon |
| 6,287,326 | B1 | 9/2001 | Pecor | 7,029,467 B2 | 4/2006 | Currier et al. |
| 6,293,927 | B1 | 9/2001 | McGuckin, Jr. | 7,066,914 B2 * | 6/2006 | Andersen ................ 604/270 |
| 6,293,958 | B1 | 9/2001 | Berry et al. | 7,066,925 B2 * | 6/2006 | Gately et al. ................ 604/523 |
| 6,296,631 | B2 | 10/2001 | Chow | 7,074,213 B2 | 7/2006 | McGuckin, Jr. et al. |
| 6,299,631 | B1 | 10/2001 | Shalaby | 7,077,829 B2 | 7/2006 | McGuckin, Jr. et al. |
| 6,322,551 | B1 | 11/2001 | Brugger | 7,087,053 B2 | 8/2006 | Vanney |
| 6,328,730 | B1 | 12/2001 | Harkrider, Jr. | 7,090,654 B2 * | 8/2006 | Lotito et al. ................ 604/43 |
| 6,342,120 | B1 | 1/2002 | Basta | 7,108,674 B2 | 9/2006 | Quinn |
| 6,361,529 | B1 | 3/2002 | Goodin et al. | D530,420 S | 10/2006 | Chesnin |
| 6,383,172 | B1 | 5/2002 | Barbut | 7,128,734 B1 | 10/2006 | Wilson et al. |
| 6,394,141 | B2 | 5/2002 | Wages et al. | 7,130,700 B2 | 10/2006 | Gardeski et al. |
| 6,394,142 | B1 | 5/2002 | Woelfel et al. | 7,141,035 B2 | 11/2006 | Haggstrom |
| 6,409,700 | B1 | 6/2002 | Siegel, Jr. et al. | RE39,451 E | 12/2006 | Kuhle |
| 6,413,228 | B1 | 7/2002 | Hung et al. | 7,182,746 B2 | 2/2007 | Haarala et al. |
| 6,428,513 | B1 | 8/2002 | Abrahamson | 7,300,430 B2 | 11/2007 | Wilson et al. |
| 6,443,922 | B1 | 9/2002 | Roberts et al. | 7,322,953 B2 | 1/2008 | Redinger |
| 6,450,988 | B1 | 9/2002 | Bradshaw | 7,347,852 B2 | 3/2008 | Hobbs et al. |
| 6,453,185 | B1 | 9/2002 | O'Keefe | 7,381,204 B2 | 6/2008 | Wilson et al. |
| 6,454,997 | B1 | 9/2002 | Divino, Jr. et al. | 7,393,339 B2 | 7/2008 | Zawacki et al. |
| 6,463,335 | B1 | 10/2002 | Munch et al. | 7,422,571 B2 | 9/2008 | Schweikert et al. |
| 6,475,207 | B1 | 11/2002 | Maginot et al. | 7,465,286 B2 | 12/2008 | Patterson et al. |
| 6,475,209 | B1 | 11/2002 | Larson et al. | 7,485,107 B2 | 2/2009 | DiFiore et al. |
| 6,478,789 | B1 | 11/2002 | Spehalski et al. | 7,569,029 B2 | 8/2009 | Clark |
| 6,482,169 | B1 * | 11/2002 | Kuhle ................ 604/6.16 | 7,575,563 B2 | 8/2009 | Appling |
| 6,533,763 | B1 | 3/2003 | Schneiter | 7,798,999 B2 | 9/2010 | Bailey et al. |
| 6,565,594 | B1 | 5/2003 | Herweck et al. | 8,066,660 B2 * | 11/2011 | Gregersen et al. ................ 604/29 |
| 6,576,001 | B2 | 6/2003 | Werneth et al. | 8,092,415 B2 * | 1/2012 | Moehle et al. ................ 604/6.16 |
| 6,582,459 | B1 | 6/2003 | Lau et al. | 2001/0041857 A1 | 11/2001 | Sansoucy |

| | | |
|---|---|---|
| 2001/0041873 A1 | 11/2001 | Dopper et al. |
| 2002/0013569 A1 | 1/2002 | Sterman et al. |
| 2002/0026156 A1 | 2/2002 | Quinn |
| 2002/0086047 A1 | 7/2002 | Mueller et al. |
| 2002/0087108 A1 | 7/2002 | Maginot et al. |
| 2002/0087145 A1 | 7/2002 | Ehwald et al. |
| 2002/0091362 A1 | 7/2002 | Maginot et al. |
| 2002/0091430 A1 | 7/2002 | Dobak et al. |
| 2002/0099326 A1 | 7/2002 | Wilson et al. |
| 2002/0099327 A1 | 7/2002 | Wilson et al. |
| 2002/0107506 A1 | 8/2002 | McGuckin et al. |
| 2002/0138031 A1 | 9/2002 | Ross |
| 2002/0169490 A1 | 11/2002 | Noda et al. |
| 2002/0177904 A1 | 11/2002 | Huxel et al. |
| 2003/0023198 A1 | 1/2003 | Twardowski |
| 2003/0088213 A1 | 5/2003 | Schweikert et al. |
| 2003/0093027 A1 | 5/2003 | McGuckin et al. |
| 2003/0097091 A1 | 5/2003 | Hobbs et al. |
| 2003/0144623 A1 | 7/2003 | Heath et al. |
| 2003/0149395 A1* | 8/2003 | Zawacki ............... 604/40 |
| 2003/0153898 A1 | 8/2003 | Schon et al. |
| 2003/0187411 A1 | 10/2003 | Constantz |
| 2003/0204179 A1 | 10/2003 | Davey et al. |
| 2004/0054321 A1 | 3/2004 | Schon et al. |
| 2004/0059314 A1 | 3/2004 | Schon et al. |
| 2004/0064086 A1 | 4/2004 | Gottlieb et al. |
| 2004/0065333 A1 | 4/2004 | Wilson et al. |
| 2004/0075198 A1 | 4/2004 | Schweikert et al. |
| 2004/0087892 A1 | 5/2004 | Cunningham |
| 2004/0092863 A1 | 5/2004 | Raulerson et al. |
| 2004/0097863 A1 | 5/2004 | Appling |
| 2004/0097903 A1 | 5/2004 | Raulerson |
| 2004/0122418 A1 | 6/2004 | Voorhees |
| 2004/0147903 A1 | 7/2004 | Latini |
| 2004/0167463 A1* | 8/2004 | Zawacki et al. ............... 604/43 |
| 2004/0171997 A1 | 9/2004 | Wilson et al. |
| 2004/0172003 A1 | 9/2004 | Wilson et al. |
| 2004/0176739 A1 | 9/2004 | Stephens et al. |
| 2004/0193102 A1* | 9/2004 | Haggstrom ............... 604/43 |
| 2004/0210180 A1 | 10/2004 | Altman |
| 2004/0210187 A1 | 10/2004 | Zawacki |
| 2004/0210237 A1 | 10/2004 | Ross et al. |
| 2004/0220550 A1 | 11/2004 | Schryver |
| 2004/0230204 A1 | 11/2004 | Wortley et al. |
| 2004/0243095 A1 | 12/2004 | Nimkar et al. |
| 2004/0249337 A1 | 12/2004 | DiFiore |
| 2005/0003322 A1 | 1/2005 | Logan et al. |
| 2005/0004504 A1 | 1/2005 | Frye et al. |
| 2005/0013341 A1 | 1/2005 | Baghai |
| 2005/0025641 A1 | 2/2005 | Shibata et al. |
| 2005/0027282 A1 | 2/2005 | Schweikert et al. |
| 2005/0027289 A1 | 2/2005 | Castellano et al. |
| 2005/0033222 A1 | 2/2005 | Haggstrom et al. |
| 2005/0054989 A1 | 3/2005 | McGuckin et al. |
| 2005/0055012 A1 | 3/2005 | Trerotola |
| 2005/0059925 A1 | 3/2005 | Maginot et al. |
| 2005/0070842 A1* | 3/2005 | Lotito et al. ............... 604/43 |
| 2005/0080398 A1 | 4/2005 | Markel et al. |
| 2005/0085765 A1 | 4/2005 | Voorhees |
| 2005/0096585 A1* | 5/2005 | Schon et al. ............... 604/43 |
| 2005/0113904 A1 | 5/2005 | Shank et al. |
| 2005/0131341 A1 | 6/2005 | McGuckin et al. |
| 2005/0171469 A1 | 8/2005 | Cunningham |
| 2005/0187535 A1 | 8/2005 | Wilson et al. |
| 2005/0228339 A1 | 10/2005 | Clark |
| 2005/0245900 A1 | 11/2005 | Ash |
| 2005/0256461 A1 | 11/2005 | DiFiore et al. |
| 2005/0261663 A1 | 11/2005 | Patterson et al. |
| 2005/0267400 A1* | 12/2005 | Haarala et al. ............... 604/43 |
| 2005/0277862 A1 | 12/2005 | Anand |
| 2005/0288623 A1* | 12/2005 | Hjalmarsson ............... 604/43 |
| 2005/0288706 A1 | 12/2005 | Widomski et al. |
| 2006/0004316 A1* | 1/2006 | Difiore et al. ............... 604/6.16 |
| 2006/0004325 A1 | 1/2006 | Hamatake et al. |
| 2006/0009783 A1 | 1/2006 | Rome et al. |
| 2006/0015072 A1 | 1/2006 | Raulerson |
| 2006/0015130 A1 | 1/2006 | Voorhees et al. |
| 2006/0030827 A1 | 2/2006 | Raulerson et al. |
| 2006/0047267 A1 | 3/2006 | Gately et al. |
| 2006/0047268 A1 | 3/2006 | Stephens |
| 2006/0058775 A1 | 3/2006 | Stevens et al. |
| 2006/0064072 A1 | 3/2006 | Gately et al. |
| 2006/0095062 A1 | 5/2006 | Stephens |
| 2006/0100572 A1 | 5/2006 | DiMatteo et al. |
| 2006/0161100 A1 | 7/2006 | Hamboly |
| 2006/0184142 A1 | 8/2006 | Schon et al. |
| 2006/0189922 A1 | 8/2006 | Amarasinghe et al. |
| 2006/0206094 A1 | 9/2006 | Chesnin et al. |
| 2006/0251612 A1 | 11/2006 | Kotzev et al. |
| 2006/0253063 A1 | 11/2006 | Schweikert |
| 2006/0271012 A1 | 11/2006 | Canaud et al. |
| 2007/0005003 A1 | 1/2007 | Patterson et al. |
| 2007/0066964 A1 | 3/2007 | Atkins |
| 2007/0078478 A1 | 4/2007 | Atkins et al. |
| 2007/0106206 A1 | 5/2007 | Appling |
| 2007/0129704 A1 | 6/2007 | O'Mahony et al. |
| 2007/0167925 A1 | 7/2007 | Jacqmein |
| 2007/0225661 A1 | 9/2007 | Ash et al. |
| 2007/0225682 A1 | 9/2007 | Ash et al. |
| 2007/0282274 A1 | 12/2007 | Chesnin |
| 2008/0021417 A1 | 1/2008 | Zawacki et al. |
| 2008/0039774 A1 | 2/2008 | Zawacki et al. |
| 2008/0082079 A1* | 4/2008 | Braga et al. ............... 604/523 |
| 2008/0082080 A1* | 4/2008 | Braga ............... 604/523 |
| 2008/0097409 A1 | 4/2008 | Stephens |
| 2008/0214980 A1 | 9/2008 | Anand |
| 2008/0214992 A1 | 9/2008 | Haarala et al. |
| 2009/0118661 A1 | 5/2009 | Moehle et al. |
| 2009/0118701 A1 | 5/2009 | Nimkar et al. |
| 2009/0118707 A1 | 5/2009 | Schweikert et al. |
| 2009/0204052 A1 | 8/2009 | Nimkar et al. |
| 2009/0204079 A1 | 8/2009 | Nimkar et al. |
| 2009/0205189 A1 | 8/2009 | Nimkar et al. |
| 2009/0209940 A1 | 8/2009 | Nimkar et al. |
| 2010/0331780 A1* | 12/2010 | Bellisario et al. ............... 604/164.05 |
| 2011/0020418 A1 | 1/2011 | Bosley, Jr. et al. |
| 2012/0059304 A1 | 3/2012 | Gregersen et al. |
| 2012/0089070 A1 | 4/2012 | Moehle et al. |

FOREIGN PATENT DOCUMENTS

| | | |
|---|---|---|
| CA | 1150122 | 7/1983 |
| CA | 2474351 A1 | 8/2003 |
| DE | 8815869 U1 | 2/1989 |
| DE | 9108132 U1 | 9/1991 |
| DE | 102005051211 A1 | 5/2007 |
| EP | 0030854 A2 | 6/1981 |
| EP | 0132344 A2 | 1/1985 |
| EP | 0301854 | 2/1989 |
| EP | 0332366 A2 | 9/1989 |
| EP | 0386408 A1 | 9/1990 |
| EP | 0453234 A1 | 10/1991 |
| EP | 0476796 A1 | 3/1992 |
| EP | 0495263 A1 | 7/1992 |
| EP | 0711574 A1 | 5/1996 |
| EP | 1471966 A1 | 11/2004 |
| EP | 1599247 A2 | 11/2005 |
| GB | 1503469 | 3/1978 |
| JP | 56-136569 A | 10/1981 |
| JP | 8-510935 T | 11/1996 |
| JP | 2001137350 | 5/2001 |
| MX | 249060 | 9/2007 |
| RU | 45923 A | 11/2004 |
| SU | 459237 A1 | 2/1975 |
| WO | 9108132 A1 | 6/1991 |
| WO | 9316741 A1 | 9/1993 |
| WO | 9316752 A1 | 9/1993 |
| WO | 9709086 A1 | 3/1997 |
| WO | 9717102 | 5/1997 |
| WO | 9722374 A1 | 6/1997 |
| WO | 9737699 | 10/1997 |
| WO | 9904844 A1 | 2/1999 |
| WO | 0023137 A1 | 4/2000 |
| WO | 02058776 A2 | 8/2002 |
| WO | 02083223 A1 | 10/2002 |
| WO | 03030960 A2 | 4/2003 |
| WO | 03033049 A2 | 4/2003 |
| WO | 03066148 A1 | 8/2003 |
| WO | 2004075962 A2 | 9/2004 |

| | | |
|---|---|---|
| WO | 2004096334 | 11/2004 |
| WO | 2004112876 | 12/2004 |
| WO | 2005016432 | 2/2005 |
| WO | 2005018712 A2 | 3/2005 |
| WO | 2005023336 A2 | 3/2005 |
| WO | 2005077449 | 8/2005 |
| WO | 2006034877 | 4/2006 |
| WO | 2009051967 A1 | 4/2009 |

OTHER PUBLICATIONS

Campbell, et al., Radiological Insertion of Long-term Venous Access Devices, Seminars in Interventional Radiology, 1994, vol. II, No. 4, pp. 366-375.
Declaration of Gregory S. Haas (Plaintiff's Exhibit 88 in Haas Deposition), Mar. 13, 2003, *Thierry Pourchez and Bard Access Systems, Inc. v. Diatek, Inc. and Arrow International, Inc.*, Civil Action No. 03-CV-0972 (S.D.N.Y.).
Defendant's Exhibits DX78-DX114, *Thierry Pourchez and Bard Access Systems, Inc. v. Diatek, Inc. and Arrow International, Inc.*, Civil Action No. 03-CV-0972 (S.D.N.Y.).
Defendants' Reponses and Objections to Plaintiffs' Second Set of Interrogatories (Excerpt), *Thierry Pourchez and Bard Access Systems, Inc. v. Diatek, Inc. and Arrow International, Inc.*, Civil Action No. 03-CV-0972 (S.D.N.Y.).
Delmore et al., "Experience with the Groshong Long-Term Central Venous Catheter", Gynecologic Oncology 34, 216-218 (1989).
Difiore, "Central Venous Dialysis Catheter Evaluatio in Swine", Journal of Vascular Access Devices, Fall 2000.
Donaldson, et al., Peripherally Inserted Central Venous Catheters: US-guided Vascular Access in Pediatric Patients1, Radiology, 1995, vol. 197, pp. 542-544.
Dunea, et. al., A Survey of Permanent Double Lumen Catheters in Hemodialysis Patients. ASAIO Transac. 1991; 37: M276-7.
Dupont et al, "Long-Term Development of Permcath Quinton Catheter" [French] Néphrologie 15: 105-10 (1994) (with English summary).
Gallichio, et al., Placement of a Double Lumen Silastic Catheter for Hemodialysis Access Through The Cephalic Vein, Journal of the American College of Surgeons, 1994, vol. 179, pp. 171-172.
Gravenstein, et al., In Vitro Evaluation of Relative Perforating Potential of Central Venous Catheters: Comparison of Materials, Selected Models, Number of Lumens, and Angles of Incidence to Simulated Membrane, Journal of Clinical Monitoring, 1991, vol. 7, pp. 1-6.
Haindl, H., Technical complications of port-catheter systems, Reg. Cancer Treat, 1989, 2:238-242.
Haire, et al., Thrombotic Complications of Subclavian Apheresis catheters in Cancer Patients: Prevention With Heparin Infusion, Journal of Clinical Apheresis, 1990, vol. 5, pp. 188-191.
Hull, et al., The Groshong Catheter: Initial Experience and Early Results of Imaging-guided Placement1, Radiology, 1992, vol. 185, pp. 803-807.
Ignotus, et al., Review of Radiological Insertion of Indwelling Central Venous Catheters, Minimally Invasive Therapy, 1992, 1:373-388.
Jones, et al., Efficacy of the Supraclavicular Route for Temporary Hemodialysis Access, Southern Medical Journal, 1992, vol. 85, No. 7, pp. 725-726.
JP App. No. 2003-565569 filed Feb. 7, 2003, Translated Decision of Refusal mailed Dec. 24, 2009.
JP App. No. 2003-565569 filed Feb. 7, 2003, Translated Official Action mailed May 28, 2009.
JP App. No. 2003-565569 filed Feb. 7, 2003, Translated Official Action mailed Nov. 7, 2008.
Kapoian et al. Dialysis as Treatment of End-Stage Renal Disease, Chapter 5: Dialysis Access and Recirculation.
Kapoian, et al., Dialysis Access and Recirculation, Chapter 5, pp. 5.2-5.14.
Kaupke, et al., Perforation of the Superior Vena Cava by a Subclavian Hemodialysis Catheter: early detection by angiography, The International Journal of Artificial Organs, 1992, vol. 15, No. 11, pp. 666-668.
Kelber, et al., Factors Affecting Delivery of High-Efficiency Dialysis Using Temporary Vascular Access, American Journal of Kidney Diseases, 1993, vol. 22, No. 1, pp. 24-29.
Lumsden, et al., Hemodialysis Access in the Pediatric Patient Population, The American Journal of Surgery, 1994, vol. 168, pp. 197.
Lund, "Percutaneous Translumbar Inferior Vena Cava Cannulation and other Alternative Vascular Access Techniques" in Venous Interventional Radiology with Clinical Perspectives, Savader et al, eds. pp. 251-261 (date unknown).
Lund, et al., Percutaneous Translumbar Inferior Vena Cava Cannulation for Hemodialysis, American Journal of Kidney Diseases, 1995, vol. 25, No. 5, pp. 732-737.
Maki, D., Pathogenesis, Prevention, and Management of Infections Due to Intravascular Devices Used for Infusion Therapy, in Infections Associated with Indwelling Medical Devices, Bisno et al, eds, American Society for Microbiology, 1989, pp. 161-177.
Malviya et al., "Vascular Access in Gynecological Cancer Using the Groshong Right Atrial Catheter", Gynecological Oncology 33, 313-316 (1989).
Mauro, et al., Radiologic Placement of Long-term Central Venous Catheters: A Review, JVIR, 1993, vol. 4, No. 1, pp. 127-137.
McGee, et al., Accurate placement of central venous catheters: A prospective, randomized, multicenter trial, Critical Care Medicine, 1993, vol. 21, No. 8, pp. 1118-1123.
Medcomp® Brochure, "Ash Split Cath• XL", Dec. 2001, PN 2291.
Medcomp® Brochure, "Ash Split Cath•", Guidewire Weave Insertion Technique, Jan. 2002, PN 2296.
Medcomp® Brochure, "Ash Split Cath•", Jul. 2001, PN 2114.
Medcomp® Brochure, "Ash Split Cath•", Nov. 1997, PN 2050.
Medcomp® Brochure, "Ash Split Cath® II ", Aug. 2002, PN 2334.
Medcomp® Brochure, "Magna• High Flow Catheter", Mar. 2002, PN 2321.
Moss, et al., Use of a Silicone Catheter With a Dacron Cuff for Dialysis Short-Term Vascular Access, American Journal of Kidney Diseases, 1988, vol. XII, No. 6, pp. 492-498.
Northsea, C., Using Urakinase to Restore Patency in Double Lumen Catheters, ANNA Journal 1994, vol. 21, No. 5, pp. 261-273.
Parsa, et al., Establishment of Intravenous Lines for Long-term Intravenous Therapy and Monitoring, Surgical Clinics of N. Am. 1985, vol. 65, No. 4, pp. 835-865.
Parsa, et al., Vascular Access Techniques, Monitoring, pp. 122-145 (date unknown).
Pasquale, et al., Groshong® Versus Hickman® Catheters, Surgery, Gynecology & Obstetrics, 1992, vol. 174, pp. 408-410.
Passaro, et al., Long-term Silastic Catheters and Chest Pain, Journal of Parenteral and Enteral Nutrition, 1994, vol. 18, No. 3, pp. 240-242.
Patel et al., "Sheathless Technique of Ash Split-Cath Insertion", 12 JVIR 376-78 (Mar. 2001).
Arrow Cannon II Plus Brochure, 2006.
*Arrow International, Inc. et al v. Spire Biomedical, Inc.*, U.S. Dist Ct Dist MA CA No. 06-CV-11564-DPW, Declaration of Dr. Karim Valji.
*Arrow International, Inc. et al v. Spire Biomedical, Inc.*, U.S. Dist Ct Dist MA CA No. 06-CV-11564-DPW, Declaration of Kenneth Todd Cassidy.
*Arrow International, Inc. et al v. Spire Biomedical, Inc.*, U.S. Dist Ct Dist MA CA No. 06-CV-11564-DPW, Declaration of Rebecca R. Eisenberg in Opposition to Defendant's Motion for Partial Summary Judgment of Invalidity.
*Arrow International, Inc. et al v. Spire Biomedical, Inc.*, U.S. Dist Ct Dist MA CA No. 06-CV-11564-DPW, Memorandum of Law in Support of Defendant's Motion for Summary Judgment on Invalidity [Redacted Pursuant to Jun. 10, 2008 Order on Motion to Seal].
*Arrow International, Inc. et al v. Spire Biomedical, Inc.*, U.S. Dist Ct Dist MA CA No. 06-CV-11564-DPW, Memorandum of Law in Support of Defendant's Motion for Summary Judgment on Invalidity Exhibit A.
*Arrow International, Inc. et al v. Spire Biomedical, Inc.*, U.S. Dist Ct Dist MA CA No. 06-CV-11564-DPW, Plaintiff's Memorandum in Opposition to Defendant's Motion for Summary Judgement on Non-Infringement (Jul. 17, 2008).
*Arrow International, Inc. et al. v. Spire Biomedical, Inc.*, U.S. Dist. Ct. Dist. MA CA No. 06-CV-11564-DPW, Defendant's Omnibus Statement of Material Facts in Support of its Motions for Summary Judgment [Redacted Pursuant to Jun. 10, 2008 Order on Motion to Seal].

Bard Access Systems Hickman®, Leonard®, and Broviac® Central Venous Catheters (Long Term), Instructions for Use, 31 pages, 1999.
Bard Access Systems Hickman®, Leonard®, and Broviac® Central Venous Catheters, Nursing Procedural Manual, 52 pages, Jun. 1994.
Bard Davol® Hickman® Round Dual Lumen Catheters for Central Venous Access Informational Brochure, 2 pages, 1994.
Bard Hickman® Catheters Informational Brochure, 3 pages, 1994.
Believed to be an unpublished sketch of a conception by Dr. John Frusha; date of sketch believed to be Jun. 24, 1997.
Canaud, B et al, Permenant Twin Catheter: A Vascular Access Option of Choice for Haemodialysis in Elderly Patients, pp. 82-88, vol. 17 No. 7, 1994.
Claim Construction Order of Federal District Court dated May 9, 2003 in *Thierry Pourchez and Bard Access Systems, Inc.* v. *Diatek, Inc. and Arrow International, Inc.* litigation (S.D. N.Y. 03 Civ.0972).
Claim Construction Order of Federal District Court dated Oct. 31, 2006 in *Arrow Int'l. Inc.and Arrow Int'l. Investment Corp.* v. *Spire Biomedical, Inc.* litigation (D. Mass. Civil Action No. 06-CV-11564).
Decision of Federal District Court dated Jul. 7, 2009 granting Summary Judgement of Invalidity in *Arrow Int'l. Inc.and Arrow Int'l. Investment Corp.* v. *Spire Biomedical, Inc.* litigation (D. Mass. Civil Action No. 06-CV-11564).
TYCO Healthcare, Mahurkar Dual Lumen Catheters, Informational Brochure, 2 pages, 2004.
TYCO Healthcare, Mahurkar QPlus High Flow Acute Care Catheter, Informational Brochure, 2 pages, 2004.
TYCO Healthcare, Tal Palindrome™ Dual Lumen Catheters Order Information, Features and Benefits, Frequently Asked Questions, printed from http://www.kendallvasculartherapy.com/VascularTherapy, 6 pages, on Mar. 1, 2007.
U.S. Appl. No. 10/445,731, filed May 27, 2003, Non-Final Office Action dated Apr. 13, 2007.
U.S. Appl. No. 10/445,731, filed May 27, 2003, Non-Final Office Action dated Dec. 12, 2008.
U.S. Appl. No. 10/445,731, filed May 27, 2003, Non-Final Office Action dated May 30, 2008.
U.S. Appl. No. 10/874,298, filed Jun. 9, 2004, Advisory Action dated Feb. 19, 2009.
U.S. Appl. No. 10/874,298, filed Jun. 9, 2004, Final Office Action dated Jul. 15, 2008.
U.S. Appl. No. 10/874,298, filed Jun. 9, 2004, Final Office Action dated Jul. 7, 2010.
U.S. Appl. No. 10/874,298, filed Jun. 9, 2004, Non-Final Office Action dated Aug. 18, 2011.
U.S. Appl. No. 10/874,298, filed Jun. 9, 2004, Non-Final Office Action dated Dec. 30, 2009.
U.S. Appl. No. 10/874,298, filed Jun. 9, 2004, Non-Final Office Action dated Feb. 2, 2011.
U.S. Appl. No. 10/874,298, filed Jun. 9, 2004, Non-Final Office Action dated Jul. 23, 2009.
U.S. Appl. No. 10/874,298, filed Jun. 9, 2004, Non-Final Office Action dated May 23, 2006.
U.S. Appl. No. 10/874,298, filed Jun. 9, 2004, Non-Final Office Action dated May 24, 2007.
U.S. Appl. No. 11/859,106, filed Sep. 21, 2007, Non-Final Office Action dated Mar. 30, 2011.
U.S. Appl. No. 12/048,871, filed Mar. 14, 2008, Final Office Action dated Jan. 20, 2011.
U.S. Appl. No. 12/048,871, filed Mar. 14, 2008, Non-Final Office Action dated Jan. 7, 2010.
U.S. Appl. No. 12/048,871, filed Mar. 14, 2008, Non-Final Office Action dated Jul. 7, 2010.
U.S. Appl. No. 12/048,871, filed Mar. 14, 2008, Non-Final Office Action dated May 12, 2009.
U.S. Appl. No. 12/244,514, filed Oct. 2, 2008, Final Office Action dated Jul. 11, 2011.
U.S. Appl. No. 12/244,514, filed Oct. 2, 2008, Non-Final Office Action dated Jan. 19, 2011.
U.S. Appl. No. 12/244,544, filed Oct. 2, 2008, Final Office Action dated Jul. 11, 2011.
U.S. Appl. No. 12/244,544, filed Oct. 2, 2008, Non-Final Office Action dated Dec. 22, 2010.
U.S. Appl. No. 12/244,554, filed Oct. 2, 2008, Final Office Action dated Dec. 27, 2010.
U.S. Appl. No. 12/244,554, filed Oct. 2, 2008, Non-Final Office Action dated Jul. 6, 2010.
U.S. Appl. No. 12/253,870, filed Oct. 17, 2008, Non-Final Office Action dated Jan. 21, 2011.
U.S. Appl. No. 12/253,870, filed Oct. 17, 2008, Notice of Allowance dated Aug. 19, 2011.
U.S. Appl. No. 12/262,820, filed Oct. 31, 2008, Non-Final Office Action dated Feb. 18, 2011.
U.S. Appl. No. 12/263,141, filed Oct. 31, 2008, Advisory Action dated Aug. 17, 2011.
U.S. Appl. No. 12/263,141, filed Oct. 31, 2008, Final Office Action dated May 26, 2011.
U.S. Appl. No. 12/263,141, filed Oct. 31, 2008, Non-Final Office Action dated Jan. 5, 2011.
Dupont et al, Long-term development of Permacath Quinton catheters used as a vascular access route for extra-renal detoxification; Nephrologie, vol. 15, pp. 105-110, 1994.
EP 04712925.9 filed Feb. 19, 2004 Office Action dated Nov. 7, 2008.
EP 08839196.6 filed Oct. 2, 2008 Search Opinion dated Jul. 12, 2011.
EP 08839196.6 filed Oct. 2, 2008 Search Report dated Jul. 12, 2011.
Instructions for Use (Copyright Dated 1990) for Polycath Polyurethane Central Venous Catheter; believed to have been packaged with product and sold in the United States before Jan. 4, 2000 and with related marketing materials.
Instructions for Use (Copyright Dated 1992) for FloLock Single Lumen Bi-directional Valved Catheter; believed to have been packaged with product and sold in the United States before Jan. 2000.
Instructions for Use (not dated) for Infuse-a-Cath Polyurethane Central Venous Catheter; believed to have been packaged with product and sold in the United States before Jan. 2000.
Instructions for Use for Diatek Cannon Catheter Product First Sold in the United States in Sep. 2001.
Moss et al, Use of Silicone Dual-Lumen Catheter with a Dacron Cuff as a Long Term Vascular Access for Hemodialysis Patients, Amer J Kidney Diseases, vol. XVI, No. 3, pp. 211-215, Sep. 1990.
Myers, R.D. et al, New Double-lumen Polyethylene Cannula for Push-pull Perfusion of Brain Tissue in Vivo, Journal of Neuroscience Methods, pp. 205-218, vol. 12, 1985.
OriGen, OriGen Biomedical Dual Lumen Catheter, from <http://origen.neticatheter.html>, downloaded May 13, 2009, 4 pages (reprinted for submission on Jul. 21, 2011).
PCT/US2008/078551 filed Oct. 2, 2008 International Preliminary Report on Patentability dated Apr. 20, 2010.
PCT/US2008/078551 filed Oct. 2, 2008 Search Report dated Mar. 13, 2009.
PCT/US2008/078551 filed Oct. 2, 2008 Written Opinion dated Mar. 13, 2009.
PCT/US2008/078560 filed Oct. 2, 2008 Preliminary Report on Patentability dated Aug. 26, 2010.
PCT/US2008/078560 filed Oct. 2, 2008 Search Report dated Mar. 16, 2009.
PCT/US2008/078560 filed Oct. 2, 2008 Written Opinion dated Mar. 16, 2009.
PCT/US2008/078566 filed Oct. 2, 2008 International Preliminary Report on Patentability dated Apr. 20, 2010.
PCT/US2008/078566 filed Oct. 2, 2008 Search Report dated Mar. 19, 2009.
PCT/US2008/078566 filed Oct. 2, 2008 Written Opinion dated Mar. 19, 2009.
PCT/US2008/078571 filed Oct. 2, 2008 Preliminary Report on Patentability dated Aug. 26, 2010.
PCT/US2008/078571 filed Oct. 2, 2008 Search Report dated Mar. 20, 2009.
PCT/US2008/078571 filed Oct. 2, 2008 Written Opinion dated Mar. 20, 2009.
PCT/US2008/080463 filed Oct. 20, 2008 Search Report dated Mar. 16, 2009.
PCT/US2008/082106 International Preliminary Report on Patentability dated May 4, 2010.
Raaf Dual Lumen Right Atrial Catheters Brochure—Quinton Instrument Co., 6 pages, 1993.

Tal, Michael G, Comparison of Recirculation Percentage of the Palindrome Catheter and Standard Hemodialysis Catheters in a Swine Model, J Vasc Interv Radiol, pp. 1237-1240, vol. 16, No. 9, 2005.

The Groshong™ Peripherally Inserted Central Venous Catheter Brochure—Cath-tech®, 4 pages, 1988.

Twardowski, et al., Side Holes at the Tip of Chronic Hemodialysis Catheters are Harmful, The Journal of Vascular Access 2001; 2: 8 16.

Bander, et al., Central Venous Angioaccess for Hemodialysis and Its Complications, Seminars in Dialysis, 1992, vol. 5, No. 2, pp. 121-128.

Baranowski, L., Central Venous Access Devices, Journal of Intravenous Nursing, 1993, vol. 16, No. 3, pp. 167-194.

Berkoben, et al., Maintenance of Permanent Hemodialysis Vascular Access Patency, ANNA Journal, 1995, vol. 22, No. 1, pp. 17-24.

Bolz, et al., Catheter Malfunction and Thrombus Formation on Double-Lumen Hemodialysis Catheters: An Intravascular Ultrasonographic Study, American Journal of Kidney Diseases, 1995, vol. 25, No. 4, pp. 597-602.

Bour, et al., Experience With the Double Lumen Silastic® Catheter for Hemoaccess, Surgery, Gynecology & Obstetrics, 1990, vol. 171, pp. 33-39.

Paulsen, et al., Use of Tissue Plasminogen Activator for Reopening of Clotted Dialysis Catheters, Nephron, 1993, vol. 64, pp. 468-470.

PCT/US2003/003751 filed Feb. 7, 2003 Preliminary Examination Report dated May 5, 2004.

PCT/US2003/003751 filed Feb. 7, 2003 Search Report dated Jul. 3, 2003.

PCT/US2004/005102 filed Feb. 19, 2004 Preliminary Report Patenability dated Aug. 29, 2005.

PCT/US2004/005102 filed Feb. 19, 2004 Search Report dated Dec. 27, 2004.

PCT/US2004/005102 filed Feb. 19, 2004 Written Opinion dated Aug. 21, 2005.

PCT/US2008/080463 filed Oct. 20, 2008 Preliminary Report on Patentability dated Apr. 27, 2010.

Swartz, et al., Successful Use of Cuffed Central Venous Hemodialysis Catheters Inserted Percutaneously, J. Am. Soc. Nephrol., 1994, 4:1719-1725.

Tesio, et al., Double Catheterization of the Internal Jugular Vein for Hemodialysis: Indications, Techniques, and Clinical Results, Artificial Organs, 1994, vol. 18, No. 4, pp. 301-304.

Transcript of Videotaped Deposition of Gregory Haas (Excerpt), Sep. 23, 2003, *Thierry Pourchez and Bard Access Systems, Inc.* v. *Diatek, Inc. and Arrow International, Inc.*, Civil Action No. 03-CV-0972 (S.D.N.Y.).

Transcript of Videotaped Deposition of Thierry Pourchez, vol. 1, Oct. 16, 2003, *Thierry Pourchez and Bard Access Systems, Inc.* v. *Diatek, Inc. and Arrow International, Inc.*, Civil Action No. 03-CV-0972 (S.D.N.Y.).

Transcript of Videotaped Deposition of Thierry Pourchez, vol. 2, Oct. 17, 2003, *Thierry Pourchez and Bard Access Systems, Inc.* v. *Diatek, Inc. and Arrow International, Inc.*, Civil Action No. 03-CV-0972 (S.D.N.Y.).

Treiman, et al., Chronic Venous Access in Patients with Cancer, Cancer, 1993, vol. 72, No. 3, pp. 760-765.

Twardowski et al. "Side Holes at the Tip of Chronic Hemodialysis Catehters are Harmful," The Journal of Vascular Access 2001; 2:8-16.

Twardowski et al., "Blood Recirculation in Intravenous Catheters for Hemodialysis" J. Am. Soc. Nephrol. 3:1978-81 (1993).

Uldall, P., Subclavian Cannulation Is No Longer Necessary or Justified in Patients with End-Stage Renal Failure, Seminars in Dialysis, 1994, vol. 7, No. 3, pp. 161-164.

U.S. Appl. No. 11/859,106, filed Sep. 21, 2007, Final Office Action dated Sep. 1, 2009.

U.S. Appl. No. 11/859,106, filed Sep. 21, 2007, Non-Final Office Action dated Jun. 25, 2008.

U.S. Appl. No. 10/842,586, filed May 10, 2004, Advisory Action dated Oct. 9, 2008.

U.S. Appl. No. 10/842,586, filed May 10, 2004, Final Office Action dated May 25, 2010.

U.S. Appl. No. 10/842,586, filed May 10, 2004, Final Office Action dated Jul. 29, 2008.

U.S. Appl. No. 10/842,586, filed May 10, 2004, Non-Final Office Action dated Jan. 7, 2008.

U.S. Appl. No. 10/842,586, filed May 10, 2004, Non-Final Office Action dated Jun. 16, 2009.

U.S. Appl. No. 10/842,586, filed May 10, 2004, Non-Final Office Action dated Nov. 13, 2008.

U.S. Appl. No. 10/842,586, filed May 10, 2004, Non-Final Office Action dated Nov. 23, 2009.

Wechsler, et al., Thrombosis and Infection Caused by Thoracic Venous Catheters: Pathogenesis and Imagings Findings, AJR, 1993; 160:467-471.

Weitzel, et al., Successful Use of Indwelling Cuffed Femoral Vein Catheters in Ambulatory Hemodialysis Patients, American Journal of Kidney Diseases, 1993, vol. 22, No. 3, pp. 426-429.

*Arrow International, Inc. et al* v. *Spire Biomedical, Inc.*, U.S. Dist Ct Dist MA CA No. 06-CV-11564-DPW, Declaration of Dr. Karim Valji (Jul. 17, 2008).

*Arrow International, Inc. et al* v. *Spire Biomedical, Inc.*, U.S. Dist Ct Dist MA CA No. 06-CV-11564-DPW, Declaration of Kenneth Todd Cassidy (Jul. 16, 2008).

*Arrow International, Inc. et al* v. *Spire Biomedical, Inc.*, U.S. Dist Ct Dist MA CA No. 06-CV-11564-DPW, Declaration of Rebecca R. Eisenberg in Opposition to Defendant's Motion for Partial Summary Judgment of Invalidity (Jun. 8, 2009).

*Arrow International, Inc. et al* v. *Spire Biomedical, Inc.*, U.S. Dist Ct Dist MA CA No. 06-CV-11564-DPW, Memorandum of Law in Support of Defendant's Motion for Summary Judgment on Invalidity Exhibit A (Jul. 10, 2009).

*Arrow International, Inc. et al.* v. *Spire Biomedical, Inc.*, U.S. Dist. Ct. Dist. MA CA No. 06-CV-11564-DPW, Defendant's Omnibus Statement of Material Facts in Support of its Motions for Summary Judgment (Jun. 10, 2008) [Redacted Pursuant to Jun. 10, 2008 Order on Motion to Seal].

CARDINAL Search Report for 60168/85 (Feb. 25, 2009).

Defendant's Exhibits DX78-DX114, *Thierry Pourchez and Bard Access Systems, Inc.* v. *Diatek, Inc. and Arrow International, Inc.*, Civil Action No. 03-CV-0972 (S.D.N.Y.), 2003.

Defendants' Reponses and Objections to Plaintiffs' Second Set of Interrogatories (Excerpt), *Thierry Pourchez and Bard Access Systems, Inc.* v. *Diatek, Inc. and Arrow International, Inc.*, Civil Action No. 03-CV-0972 (S.D.N.Y.) (Oct. 8, 2003).

Dialysis Vascular Access, SchonXL® Temporary Dialysis (AngioDynamics Inc.) brochure, Nov. 1998.

Dialysis Vascular Access, Technological Innovations Improving Flow (AngioDynamics Inc.) Brochure, 4 pages, Nov. 1998.

EP 08872340.8 filed Oct. 2, 2008 Extended European Search Report and an Opinion dated Apr. 19, 2012.

Kapoian et al. Dialysis as Treatment of End-Stage Renal Disease, Chapter 5: Dialysis Access and Recirculation, 1999.

Lund, "Percutaneous Translumbar Inferior Vena Cava Cannulation and other Alternative Vascular Access Techniques" in Venous Interventional Radiology with Clinical Perspectives, Savader et al, eds. pp. 251-261, Apr. 10, 2000.

Mark Spector Search Report for 141-PC-06-71 (Feb. 1, 2007).

MEDCOMP, For Access via the Internal Jugular Vein . . . The Medcomp TESIO Catheter is the Solution: The Short and Long Term Solution to Subclavian Venin Stenosis and Difficult Access Problems, Brochure, 4 pages, 1991.

Memorandum: Preliminary Clearance Analysis of Power Trialysis Catheter (Mar. 2, 2009).

Parsa, et al., Vascular Access Techniques, Textbook of Critical Care, W.B. Saunders, Philadelphia, PA (1989), pp. 122-127.

Picture of Device believed to be partial sample of a product believed to have been sold in the United States with Polycath and/or Infuse-a-Cath Instructions for Use, 1 page, 2011.

PRC 200880121183.5 filed Oct. 2, 2008 First Office Action dated Mar. 28, 2012.

Rawn, et al., The Hemodialysis Access, Chapter 9, pp. 9.1-9.11, available at <<http://msl1.mit.edu/ESD10/kidneys/HndbkPDF/Chap09.pdf>>, last accessed Jun. 4, 2012.

Schwab, et al., Vascular Access: Case Oriented Discussions of Selected Critical Issues: Hemodialysis Catheters for Permanent Use, 1999.

U.S. Appl. No. 12/244,514, filed Oct. 2, 2008, Non-Final Office Action dated Jan. 17, 2012.
U.S. Appl. No. 12/262,820, filed Oct. 31, 2008, Notice of Allowance dated Sep. 28, 2011.
US Patent File History USPN 5,403,291 (Abrahamson), Apr. 4, 1995.
US Patent File History USPN 5,489,278 (Abrahamson), Feb. 6, 1996.
US Patent File History USPN 5,685,867 (Twardowski et al.), Nov. 11, 1997.

\* cited by examiner

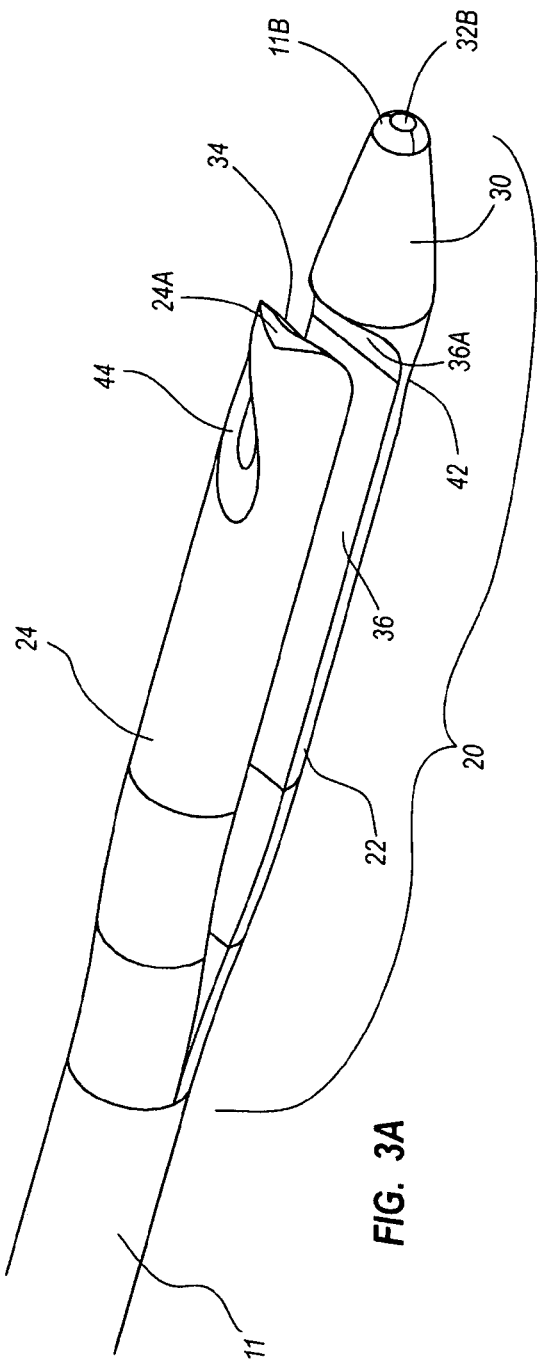
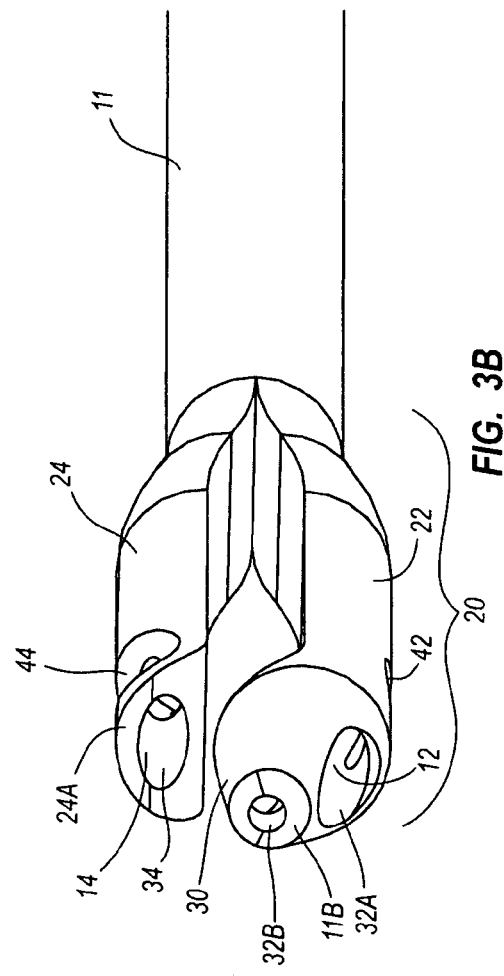
FIG. 3A
FIG. 3B

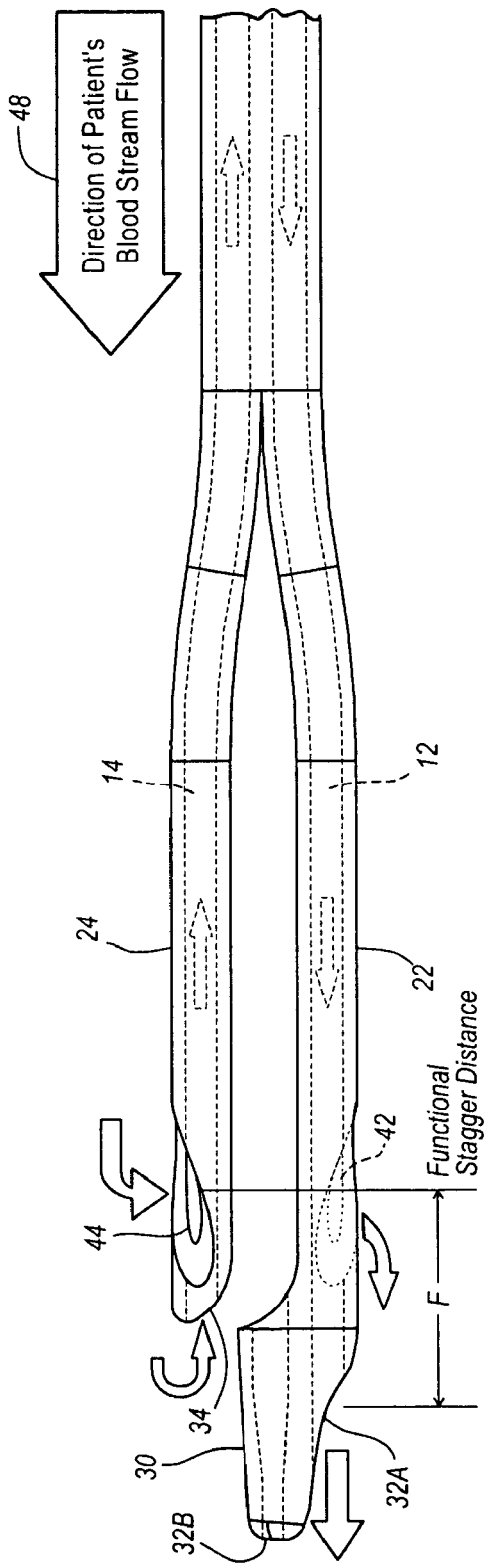
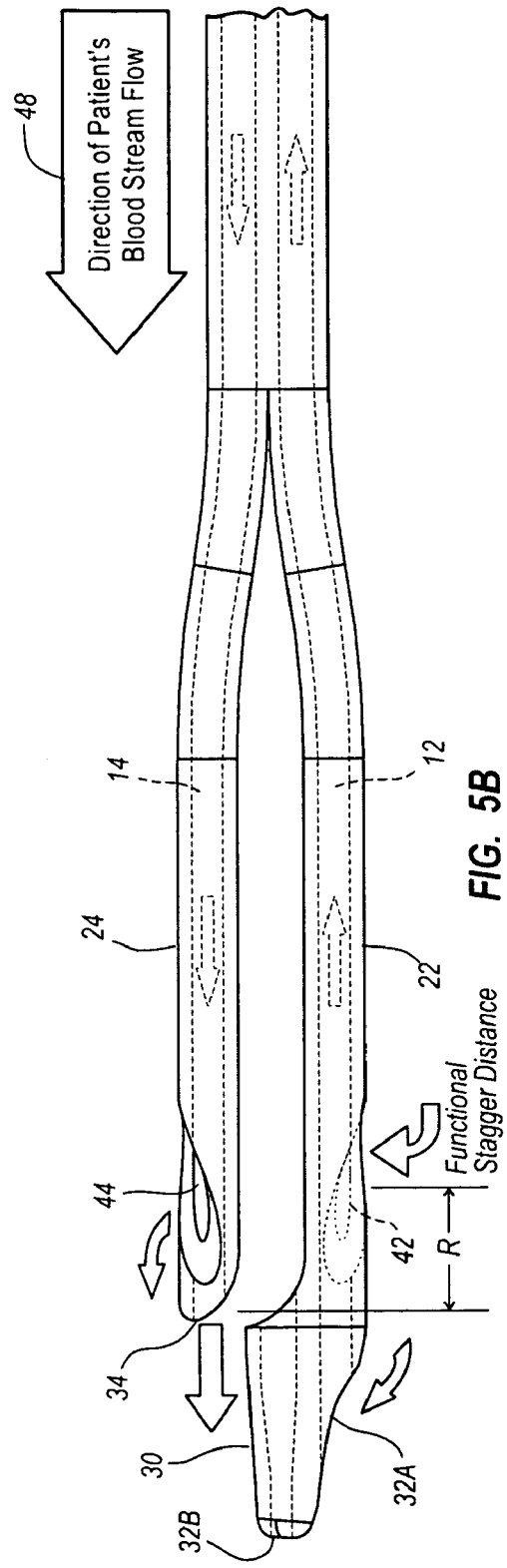
FIG. 5A
FIG. 5B

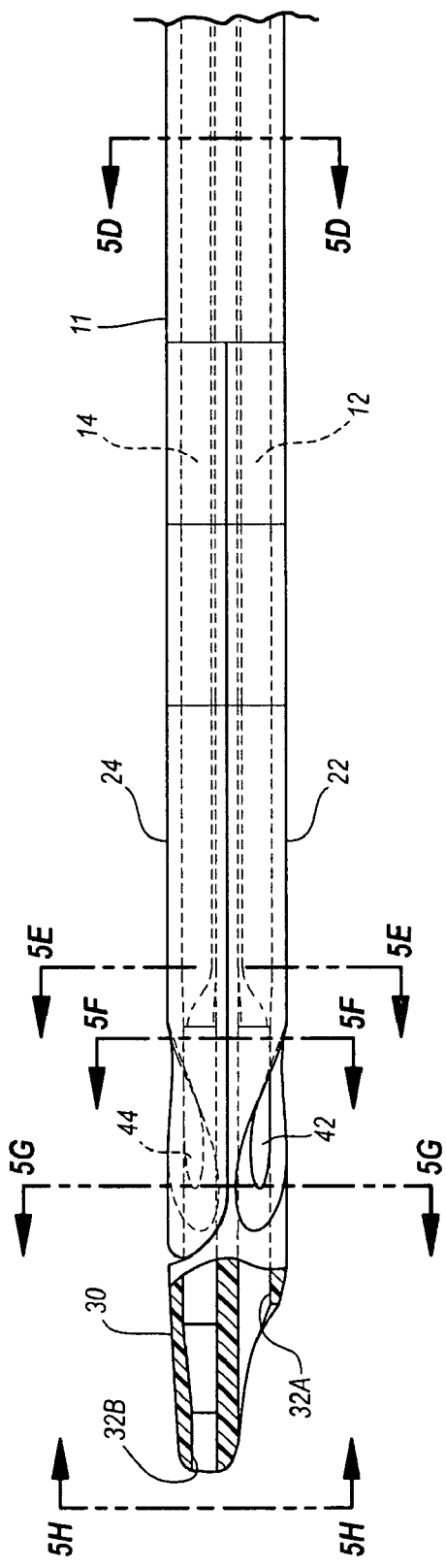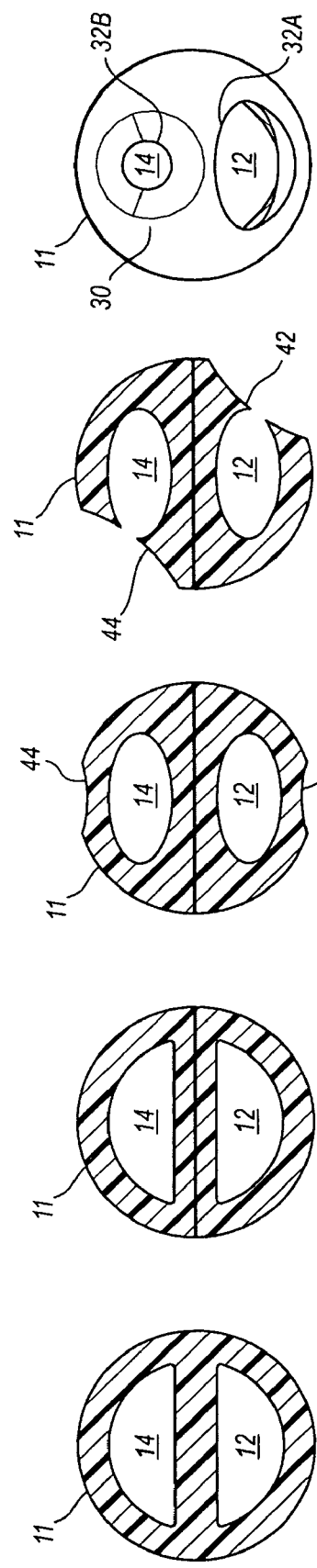

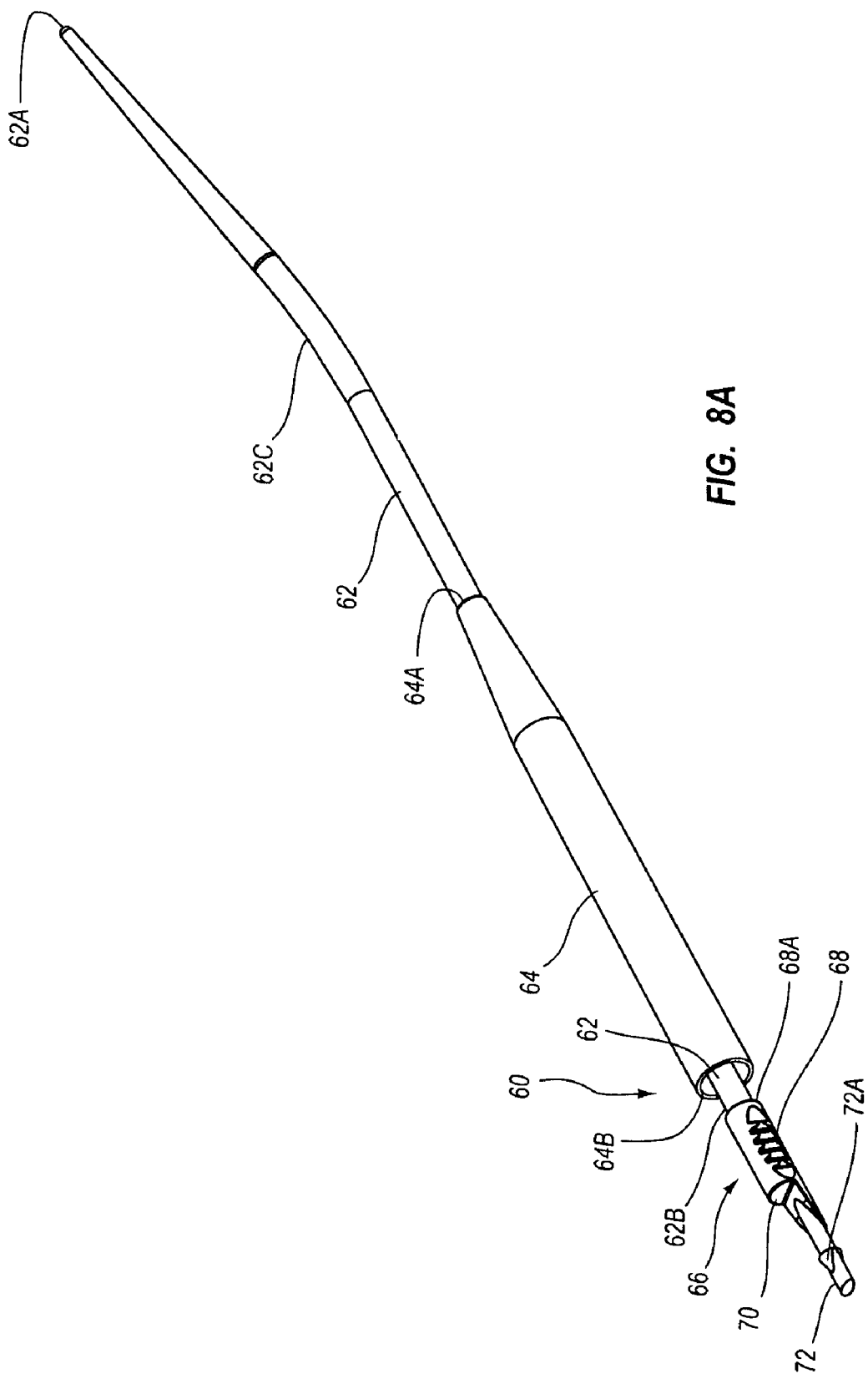

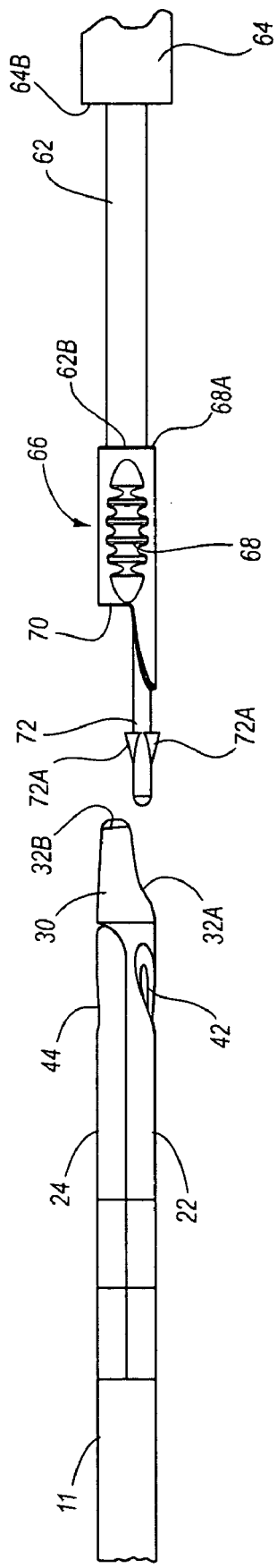
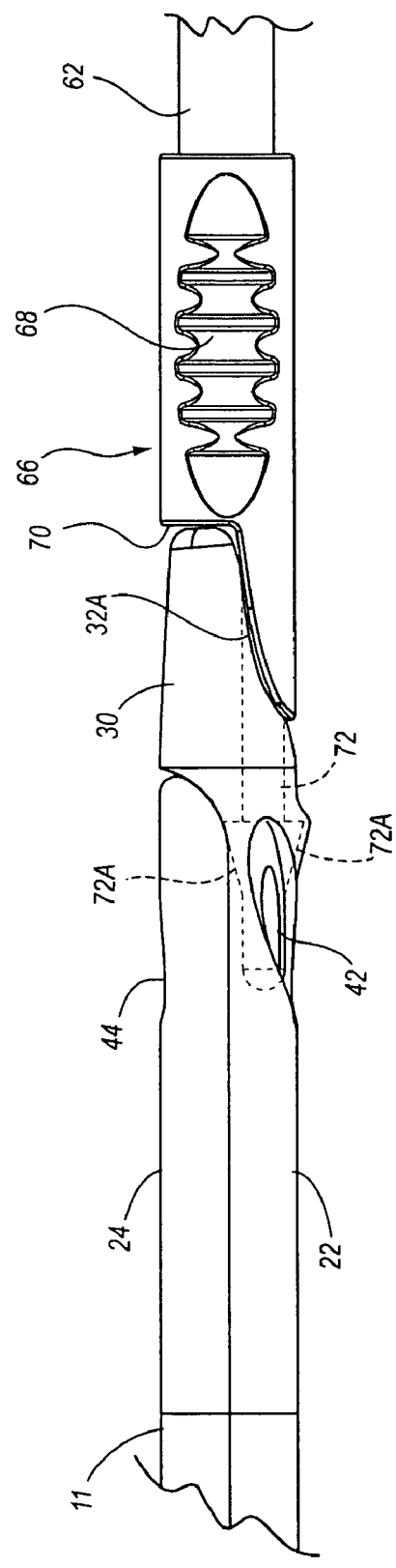
FIG. 9A
FIG. 9B

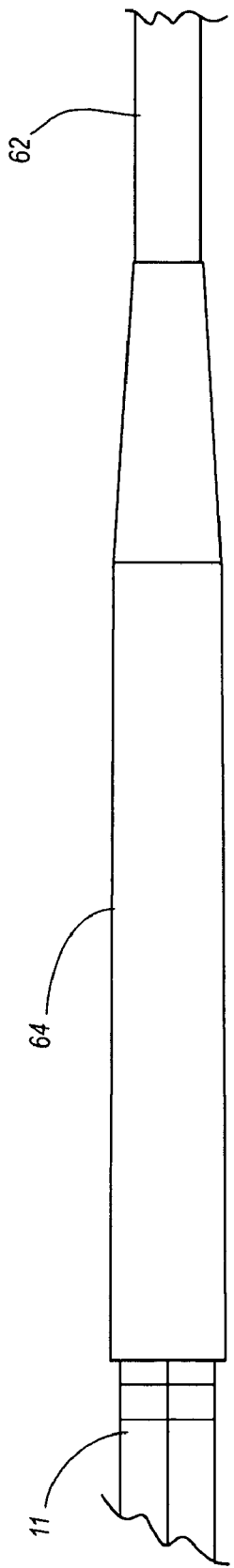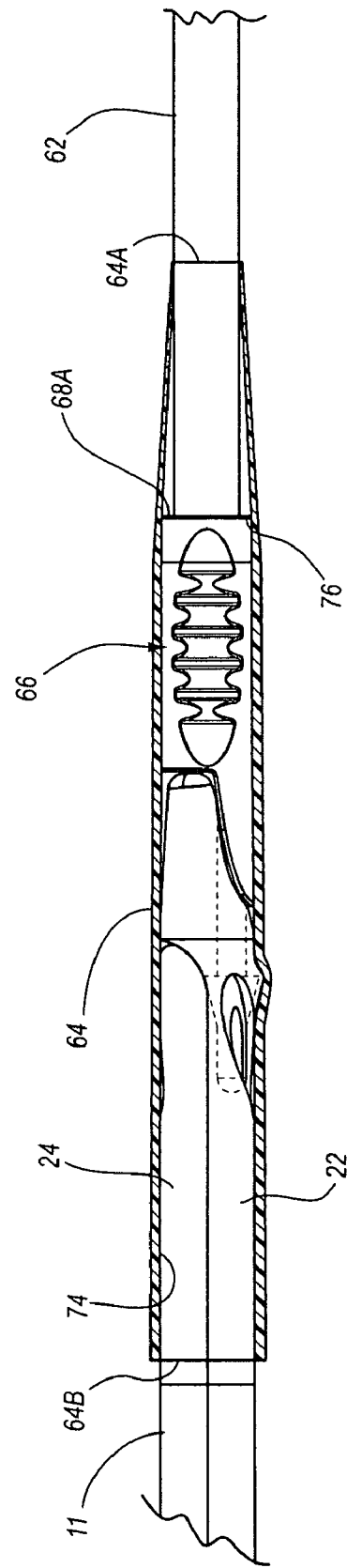
FIG. 9C
FIG. 9D

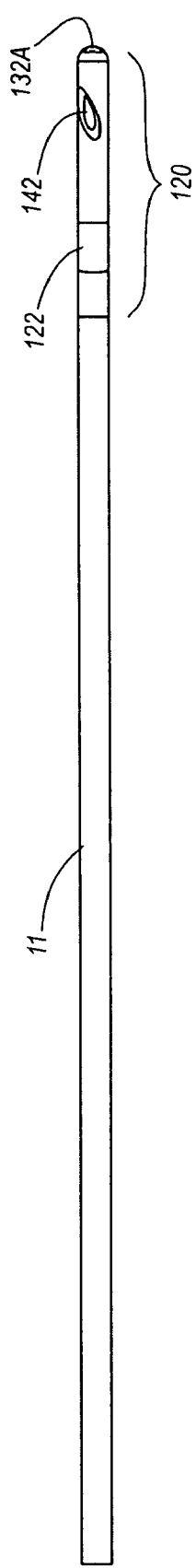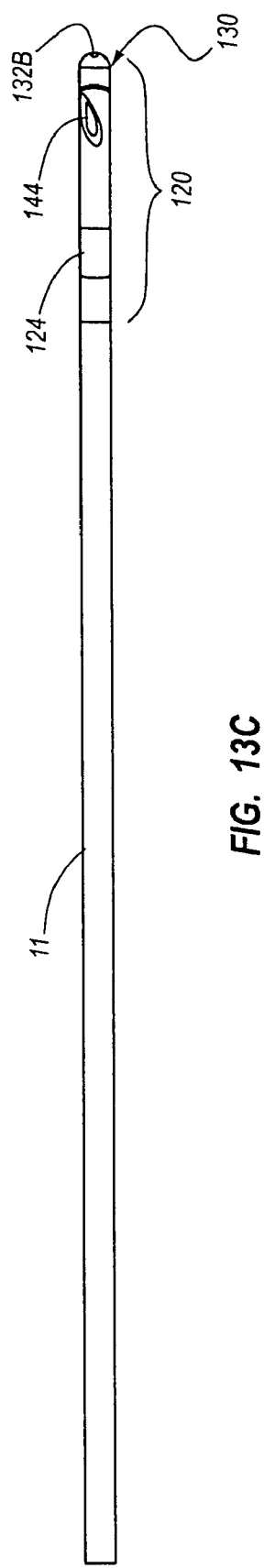
FIG. 13B
FIG. 13C

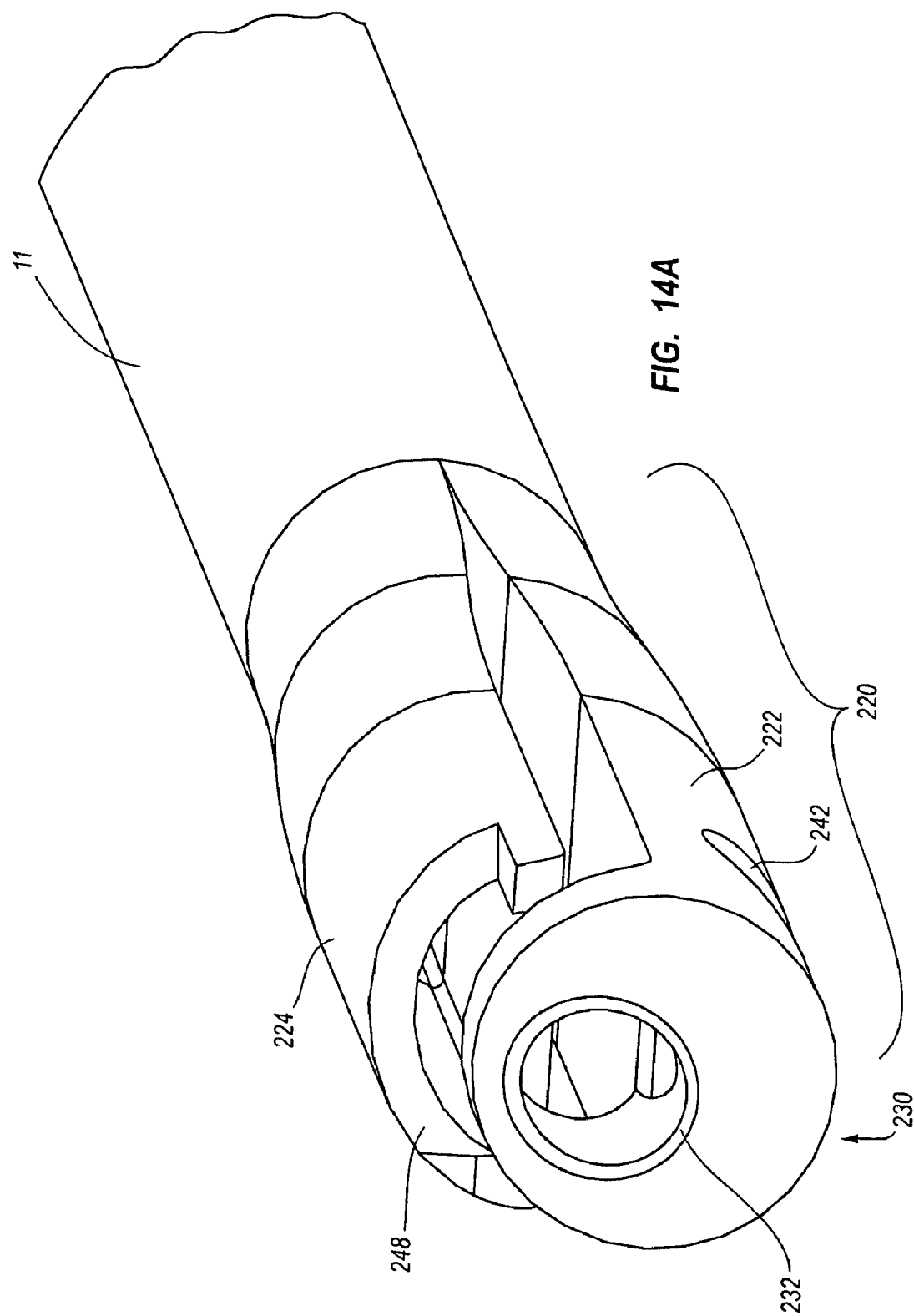

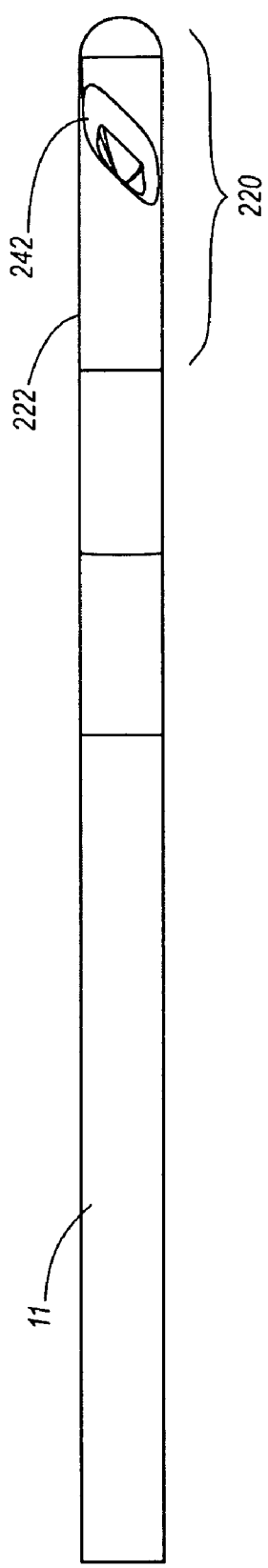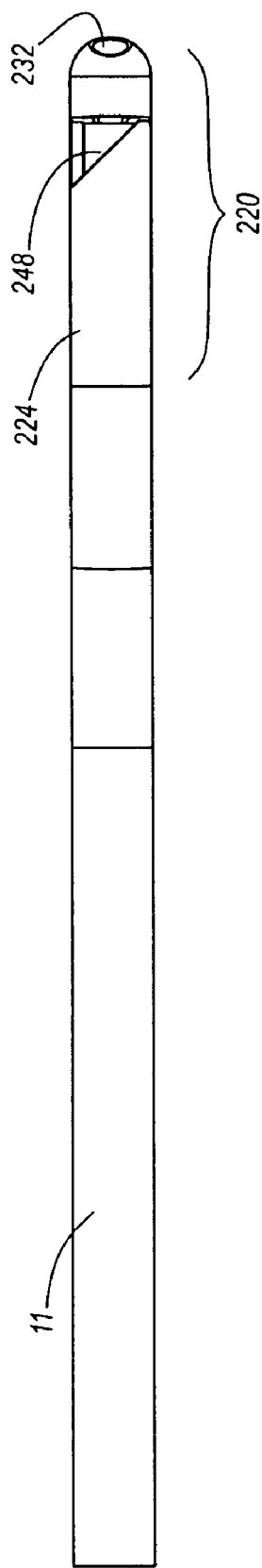
FIG. 14B
FIG. 14C

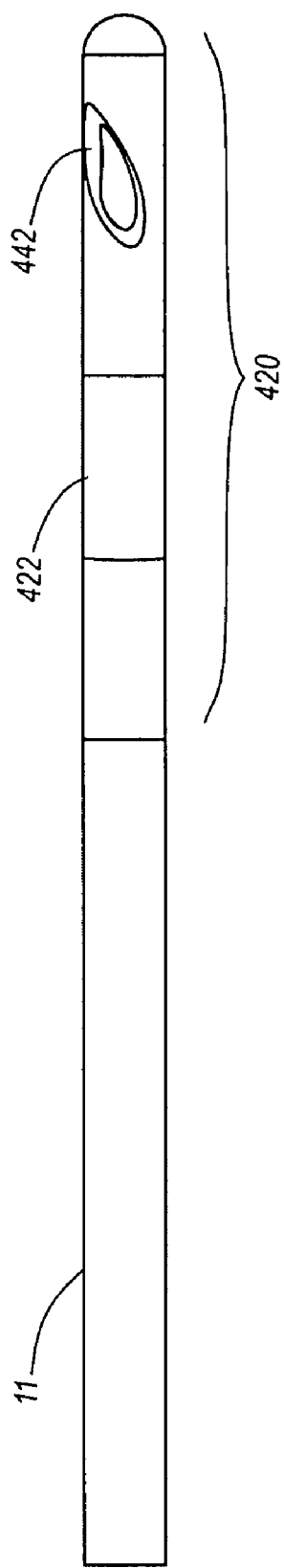
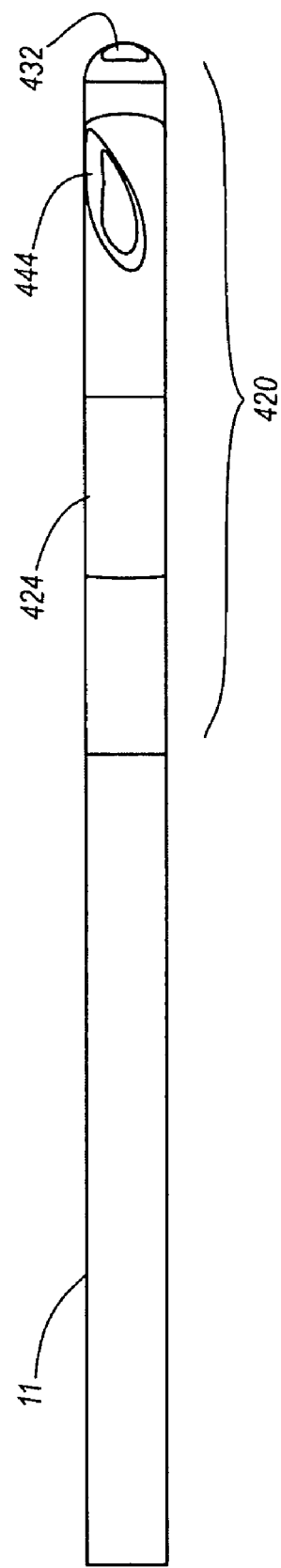
FIG. 16B
FIG. 16C

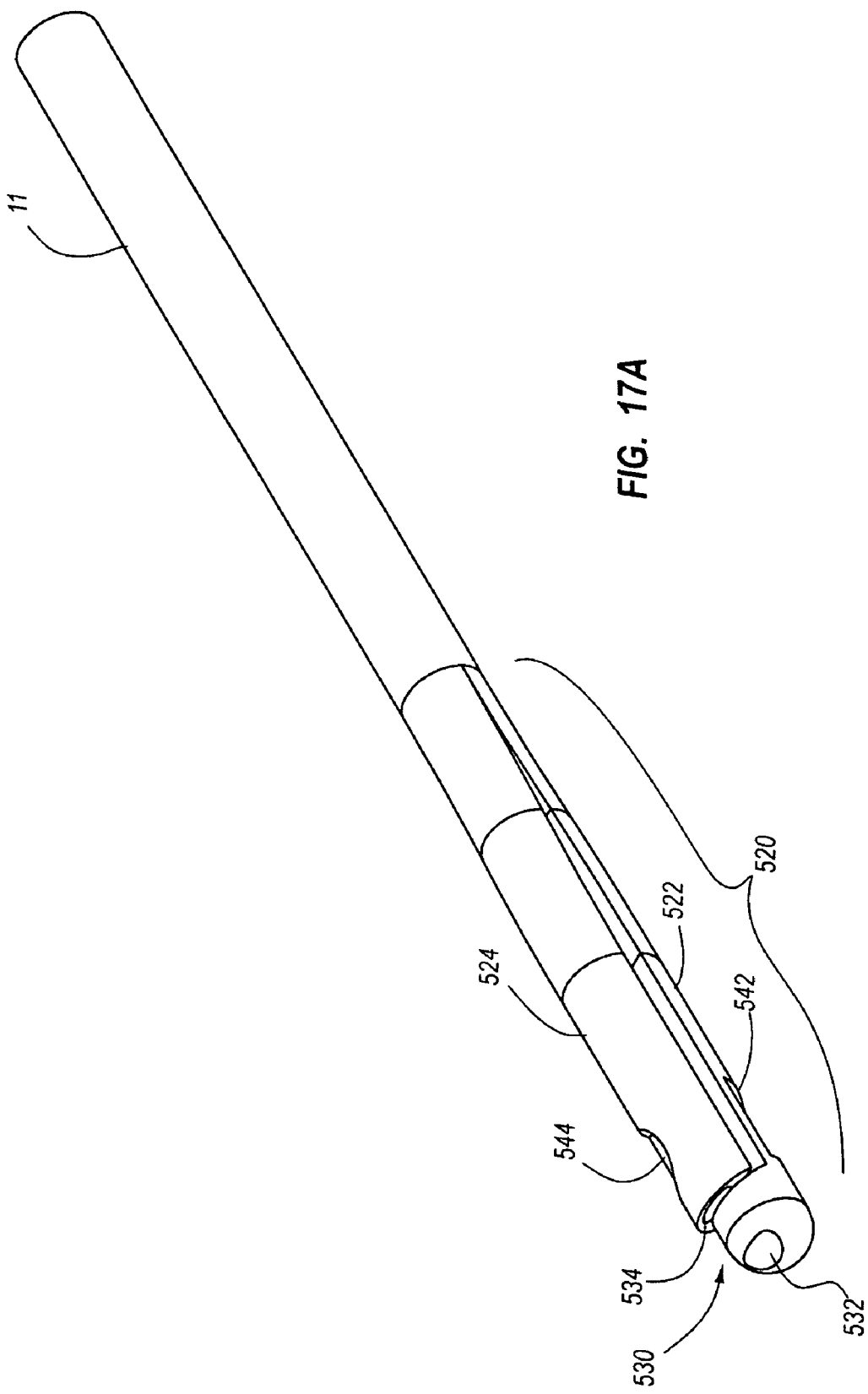

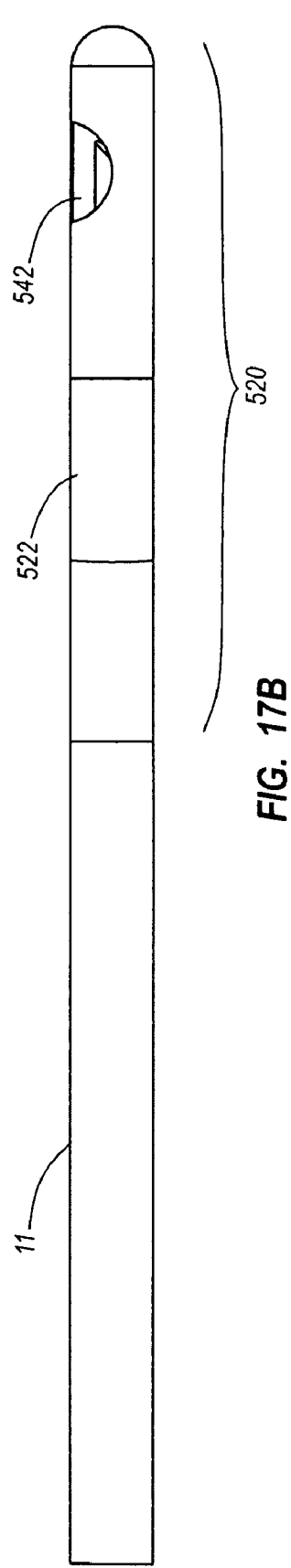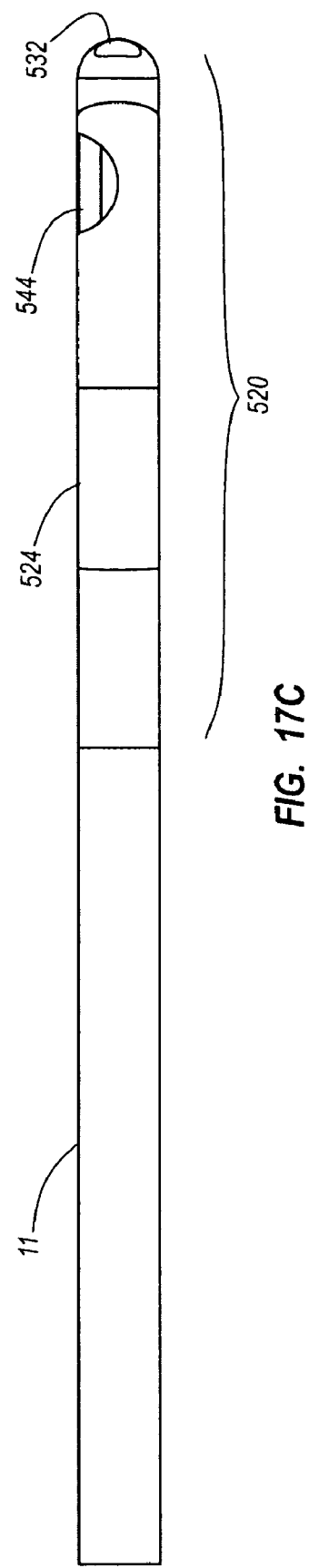

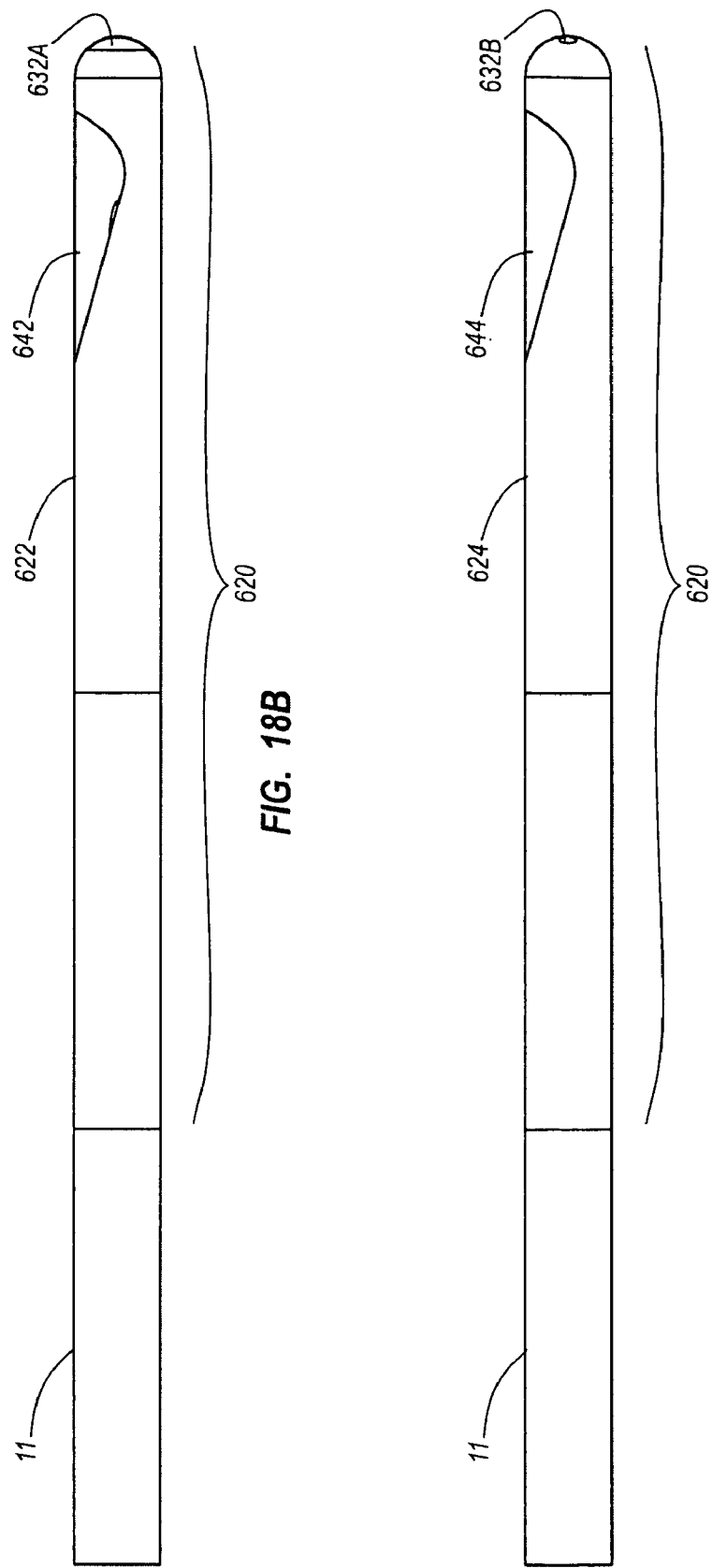

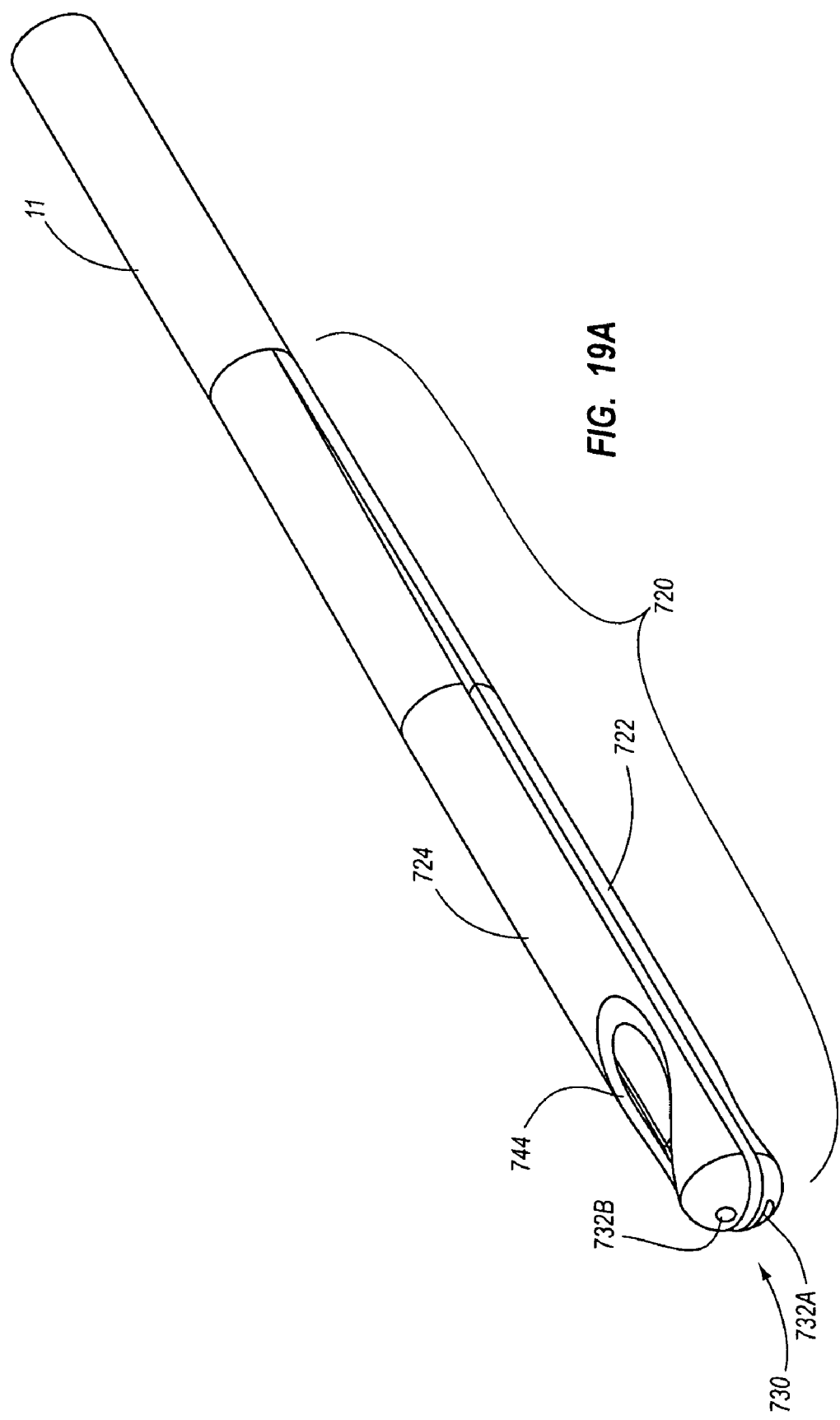

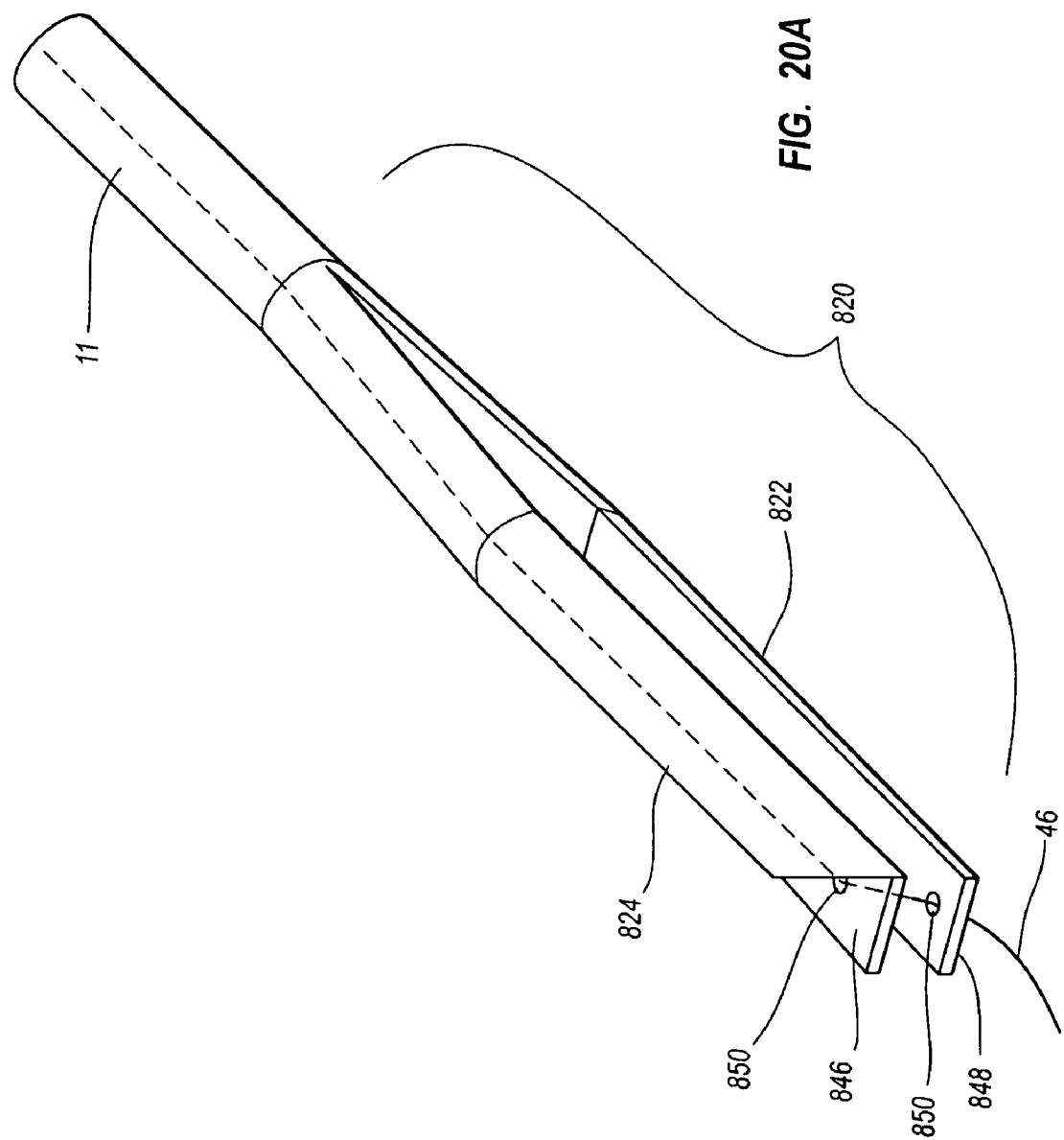

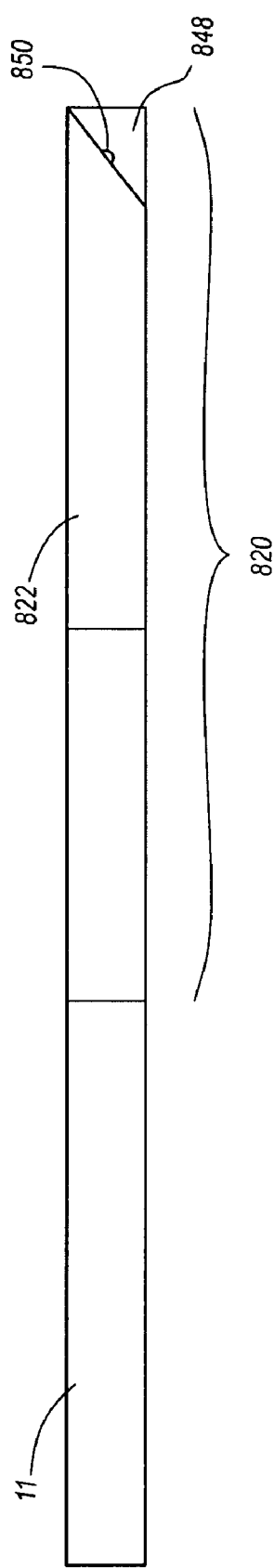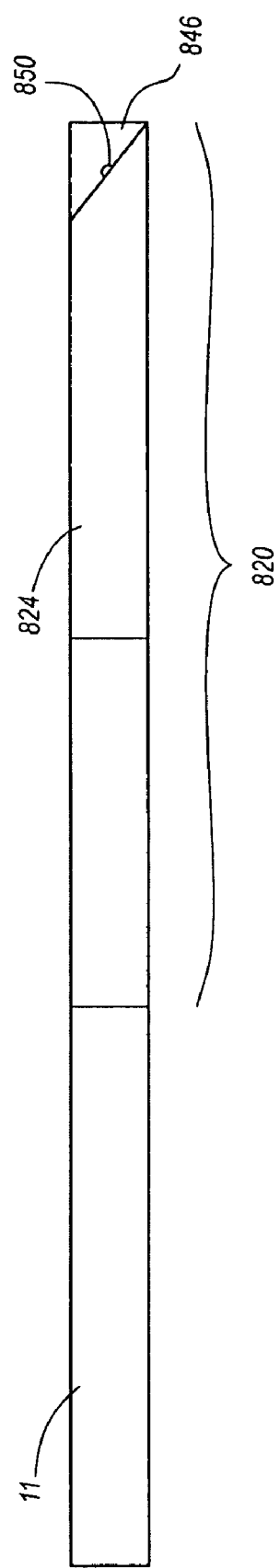
FIG. 20B
FIG. 20C

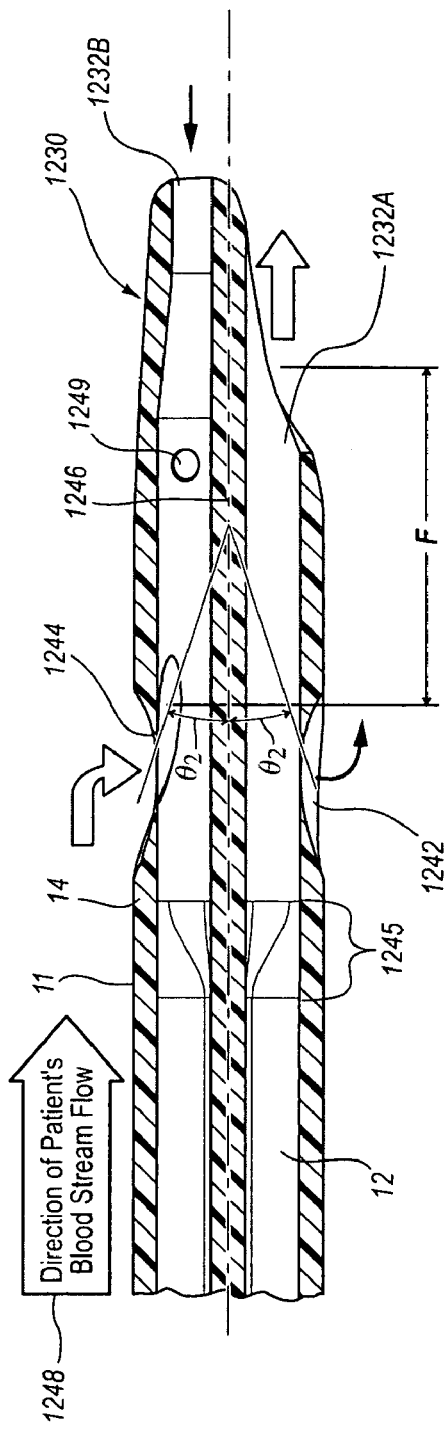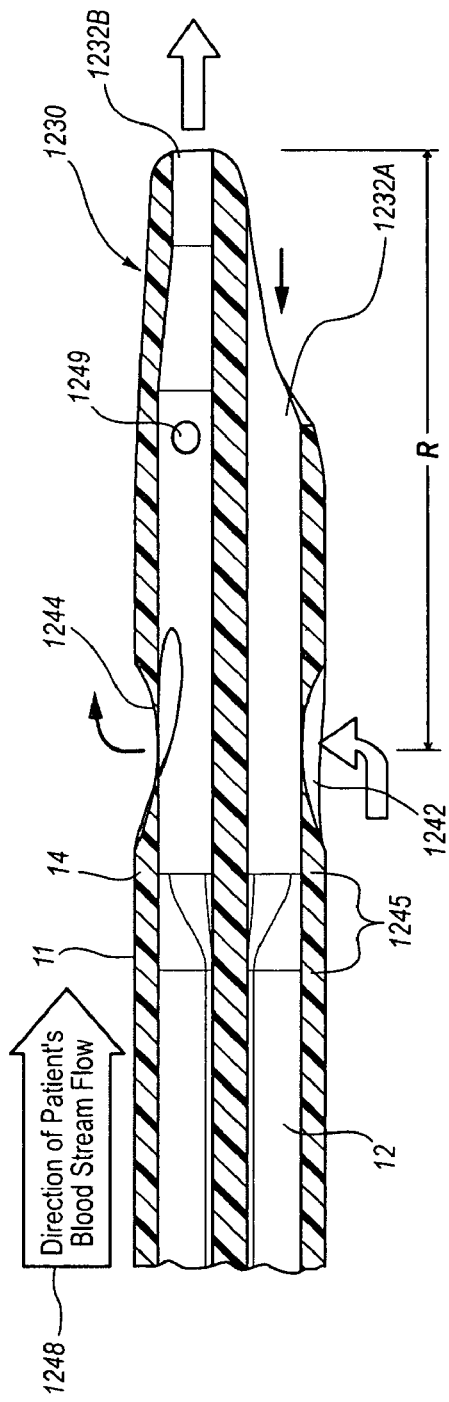
FIG. 25A
FIG. 25B

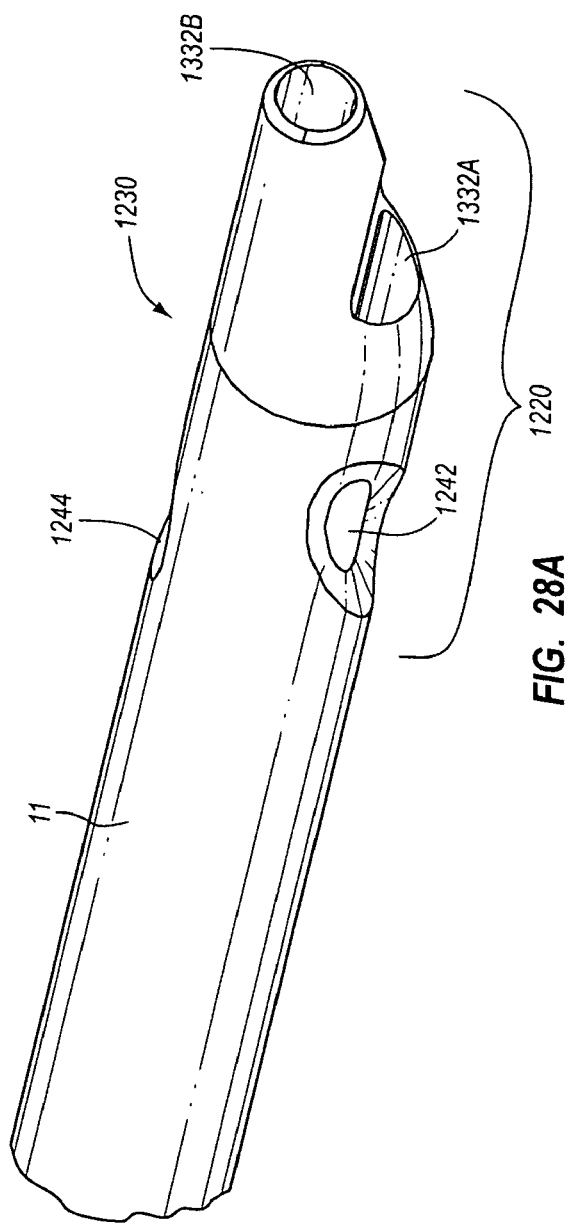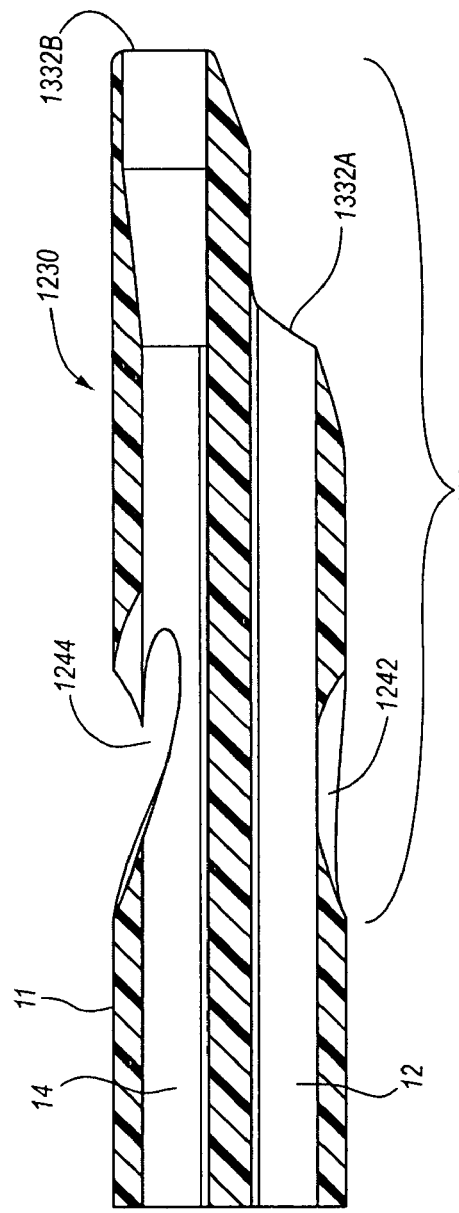
FIG. 28A
FIG. 28B

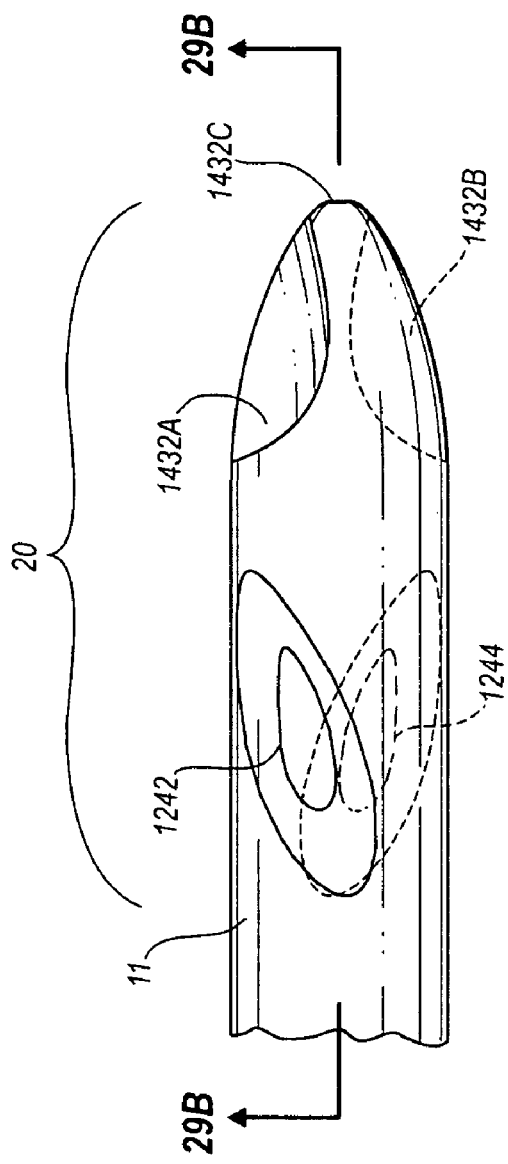
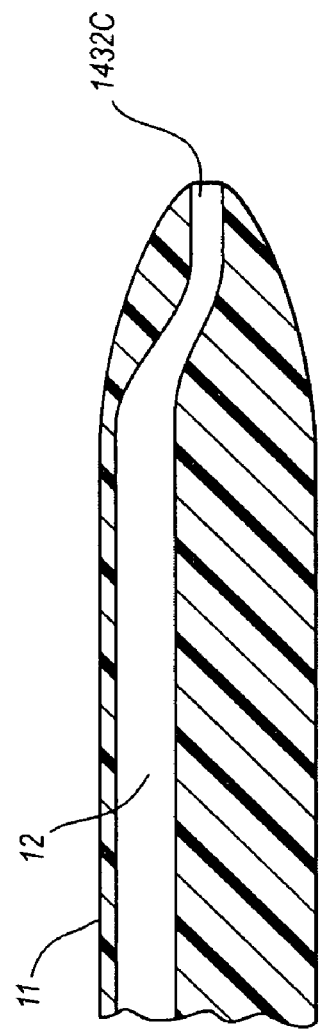
FIG. 29A
FIG. 29B

SOLID-BODY CATHETER INCLUDING LATERAL DISTAL OPENINGS

CROSS-REFERENCE TO RELATED APPLICATIONS

This application is a continuation-in-part of U.S. application Ser. No. 12/253,870, filed Oct. 17, 2008, now U.S. Pat. No. 8,066,660, and entitled "Split-Tip Catheter Including Lateral distal Openings," which claims the benefit of the following U.S. Provisional patent applications: Application No. 60/983,032, filed Oct. 26, 2007, and entitled "Over-The-Wire Split Tip Catheter;" Application No. 61/036,848, filed Mar. 14, 2008, and entitled "Split-Tip Catheter Having Lateral Distal Openings;" and Application No. 61/085,748, filed Aug. 1, 2008, and entitled "Subcutaneous Tunneling Device." Each of the afore-referenced applications is incorporated herein by reference in its entirety.

BRIEF SUMMARY

Briefly summarized, embodiments of the present invention are directed to a split-tip catheter for placement within the vasculature of a patient. The catheter is configured for use in hemodialysis treatments, though the principles of the present invention may be extended to other catheters employed in other uses in addition to hemodialysis.

In one embodiment, the split-tip catheter includes a catheter body that defines a first lumen and a second lumen. The catheter body further comprises a split distal region, including a venous segment that defines a distal portion of the first lumen and an arterial segment that defines a distal portion of the second lumen. The venous segment includes a recess extending proximally of a nose portion, and a lateral opening in fluid communication with the first lumen.

The arterial segment is separate from the venous segment in the split distal region and is removably seatable in the recess provided by the venous segment such that it "nests" therein. This nesting of the arterial segment with the venous segment provides a columnar profile for the split distal region during its advancement into and through the patient's vasculature, enabling the distal region to advance as a monolithic structure and thus easing its advancement through tortuous paths and past pathway obstacles. The segments are maintained in their nested state via a guidewire that is passed through both segments and is removable after the catheter has been suitably placed. Similar to the venous segment, the arterial segment also includes a lateral opening in fluid communication with the second lumen.

An example of a split-tip catheter that can include aspects of embodiments of the present invention is disclosed in U.S. Pat. No. 6,001,079, entitled "Multilumen Catheter, Particularly for Hemodialysis," which is incorporated herein by reference in its entirety.

In one embodiment, the distal region of the catheter is un-split, but includes symmetrically opposed lateral openings, as well as distal openings, in communication with the first and second lumens. The lateral and distal openings of the first and second lumens in the distal region provide a functional stagger for blood flow in both forward and reverse catheter flow directions. As will be further described, the configuration of the above openings is intended to reduce the likelihood of uptake and recirculation by one lumen of the catheter of treated blood just returned to the vessel via the other lumen, thus increasing catheter efficiency.

These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof that are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIGS. 3A-3D are two perspective views, a side view, and a top view, respectively, of the distal region of the split-tip catheter of FIG. 1;

FIGS. 5A and 5B are side views of the distal region of the split-tip catheter of FIG. 1 showing the flow of blood therethrough in a "forward" direction (FIG. 5A) and a "reverse" direction (FIG. 5B) when the catheter is disposed in a vasculature of a patient;

FIG. 8A is a perspective view of a subcutaneous tunneler configured in accordance with one example embodiment of the present invention;

FIGS. 9A-9D show various steps of the insertion of the subcutaneous tunneler of FIG. 8A in a distal end of a split-tip catheter, such as that shown in FIG. 1;

FIGS. 13A-13C are perspective, bottom, and top views, respectively, of a split-tip catheter including a distal region configured in accordance with one embodiment of the present invention;

FIGS. 14A-14C are perspective, bottom, and top views, respectively, of a split-tip catheter including a distal region configured in accordance with one embodiment;

FIGS. 16A-16C are perspective, bottom, and top views, respectively, of a split-tip catheter including a distal region configured in accordance with one embodiment;

FIGS. 17A-17C are perspective, bottom, and top views, respectively, of a split-tip catheter including a distal region configured in accordance with one embodiment;

FIGS. 18A-18D are perspective, bottom, top, and cross sectional views, respectively, of a split-tip catheter including a distal region configured in accordance with one embodiment;

FIGS. 19A-19D are perspective, bottom, top, and cross sectional views, respectively, of a split-tip catheter including a distal region configured in accordance with one embodiment;

FIGS. 20A-20C are perspective, bottom, and top views, respectively, of a split-tip catheter including a distal region configured in accordance with one embodiment;

FIGS. 25A-25C are various cross sectional views of the distal region of the catheter of FIG. 24A;

FIGS. 28A-28D are various views of a distal region of a catheter body, according to one example embodiment;

FIGS. 29A-29B are various views of a distal region of a catheter body, according to another example embodiment.

DETAILED DESCRIPTION OF SELECTED EMBODIMENTS

Figure 1:
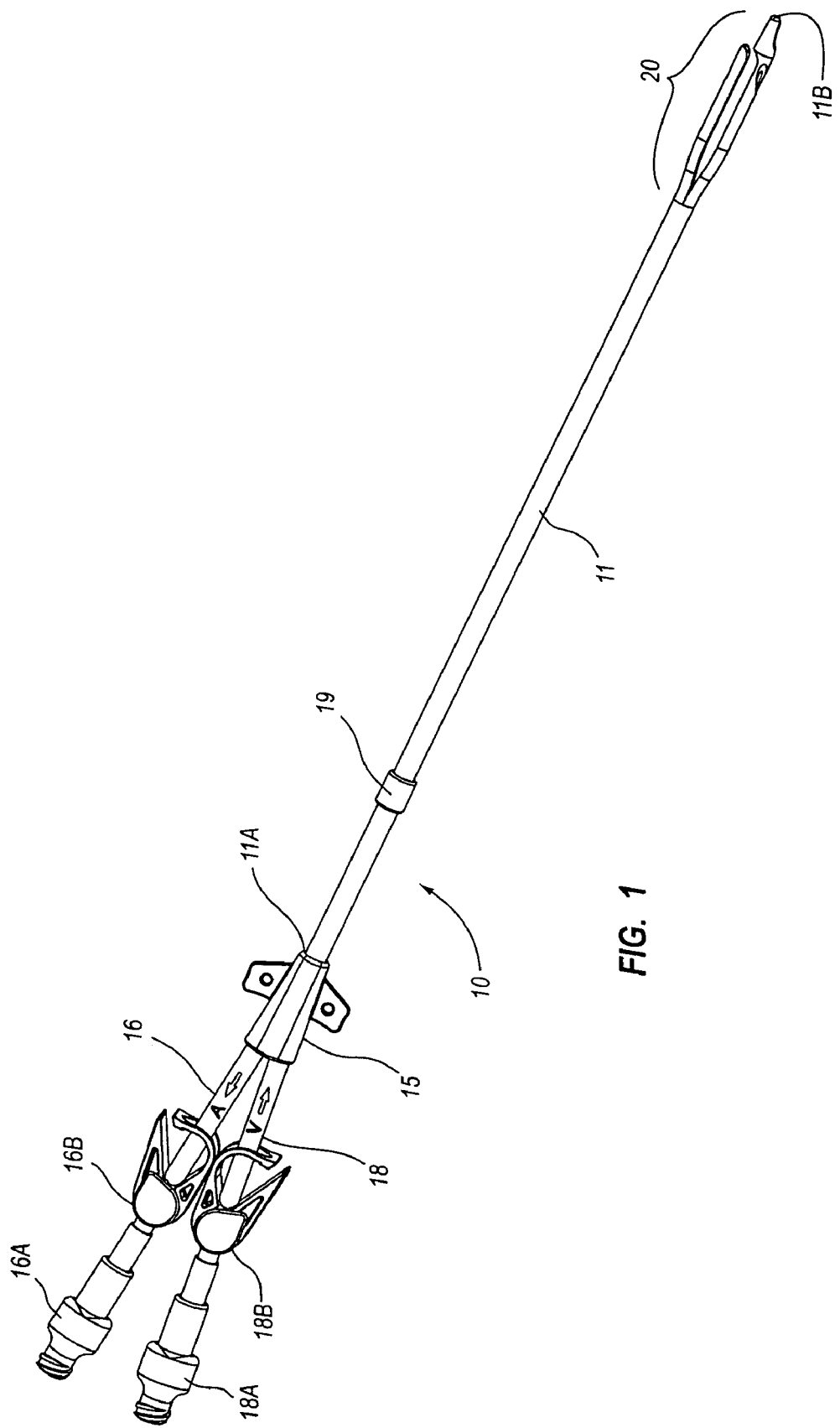
FIG. 1 is a perspective view of a catheter assembly including a split-tip distal region configured in accordance with one example embodiment of the present invention.

Reference will now be made to figures wherein like structures will be provided with like reference designations. It is understood that the drawings are diagrammatic and schematic representations of exemplary embodiments of the invention, and are not limiting of the present invention nor are they necessarily drawn to scale.

FIGS. 1-30 depict various features of embodiments of the present invention, which are generally directed to a split-tip catheter for placement within the vasculature of a patient. The catheter is configured for use in renal replacement therapies such as hemodialysis or blood purification, though the principles of the present invention may be extended to other catheters employed in other uses in addition to these. Such catheters are typically employed in long-term or chronic placement scenarios such as a placement of 30 days or more, though the principles to be described herein can also apply to short and mid-term catheter placements as well.

In accordance with one example embodiment, the split-tip portion of the catheter includes separate venous and arterial segments that are employed for simultaneously infusing and aspirating blood from a vein or other vessel of a patient's vasculature during hemodialysis treatments. The distal ends of the venous and arterial segments can be staggered to reduce the likelihood of recirculation by the arterial segment of treated blood just returned to the vessel by the venous segment, thus increasing catheter efficiency. In addition, both the venous and arterial segments are configured with openings, including laterally disposed openings, to further increase catheter efficiency during hemodialysis.

Embodiments of the split-tip catheter to be described herein further include a nested split-tip configuration, wherein the arterial segment of the catheter seats in a correspondingly shaped recess provided by a portion of the venous segment. When seated in this manner, the arterial segment defines with the venous segment a smooth, cylindrical outer surface, thus enabling the catheter to be introduced into and advanced in the patient's vasculature while avoiding snagging or obstructions that would otherwise cause the catheter to catch or bind therewith. The nested split-tip design further provides a guidewire channel for enabling a guidewire to be passed through both the venous and arterial segments to maintain the two segments in the nested configuration during catheter insertion into the vasculature. Once the catheter is properly positioned, the guidewire may be removed and the venous and arterial segments are free to separate from one another within the vessel, thus providing desired separation therebetween. A subcutaneous tunneler is also provided herein for assistance in subcutaneously tunneling the catheter.

In one embodiment, the distal region is un-split, but includes symmetrically opposed lateral openings, as well as distal openings, in communication with the first and second lumens for providing a functional stagger for blood flow in both forward and reverse catheter flow directions. The lateral and distal openings of the first and second lumens in the distal region provide a functional stagger for blood flow in both forward and reverse catheter flow directions. As with the other embodiments described herein, the configuration of the above openings is intended to reduce the likelihood of fluid recirculation so as to increase catheter efficiency.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Further, the words "including," "has," and "having," as used herein, including the claims, shall have the same meaning as the word "comprising."

Reference is first made to FIG. 1, which depicts various features of a hemodialysis split-tip catheter assembly, generally designated at 10, according to one example embodiment of the present invention. As shown, the catheter 10 includes an elongate catheter body 11 including a proximal end 11A and a distal end 11B. The elongate catheter body 11 defines a first lumen 12 and a second lumen 14 (FIG. 3B) that longitudinally extend from the proximal end 11A to the distal end 11B thereof. The lumens 12 and 14 can have one or more cross sectional shapes along their respective lengths, including round, oval, and D-cross sectional shapes. The catheter body 11 can define more than two lumens, if desired. As shown in FIG. 5B, the first and second lumens 12, 14 are split along a common septum of the catheter body 11. The catheter body 11 can be formed of a variety of suitable materials, including polyurethane, silicone, etc.

A bifurcating hub 15 is included at the catheter body proximal end 11A, providing fluid communication between the first and second lumens 12, 14 and arterial extension leg 16 and venous extension leg 18, respectively. The extension legs 16, 18 each include a luer connector 16A, 18A and a clamp 16B, 18B. So configured, the extension legs 16, 18 provide fluid communication with the first and second lumens 12 and 14 so as to enable the infusion or aspiration of fluids from a vein or other vessel or portion of a patient's vasculature. As such, fluid infusion or aspiration devices, such as a hemodialysis apparatus for example, may be connected to the catheter assembly 10 via the luer connectors 16A, 18A, thus providing intravascular access to the patient. The catheter body 11 further includes a cuff 19 for providing anchoring of the catheter body into body tissue when the catheter assembly is subcutaneously tunneled.

Figure 2:
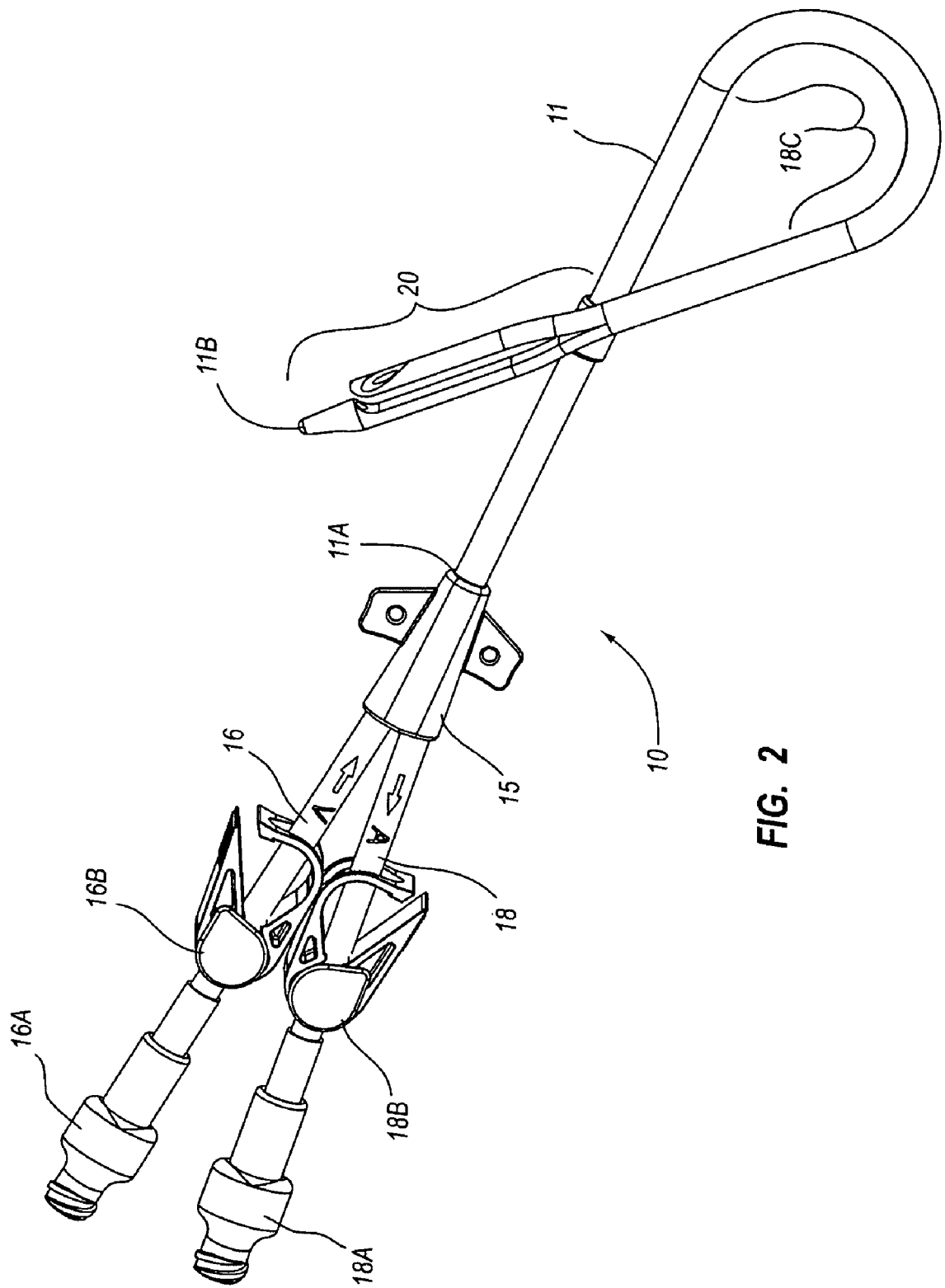
FIG. 2 is a perspective view of a catheter assembly including a split tip distal region and a pre-curved catheter body, according to one embodiment.

Reference is made to FIG. 2, which shows the catheter assembly 10, according to another example embodiment, wherein the catheter body 11 includes a pre-curved portion 18C intermediate the proximal and distal ends 11A, 11B thereof. That is, in an unstressed configuration the catheter assumes the shape shown in FIG. 2. The pre-curved portion 18C enables the exterior proximal portion of the catheter assembly 10 to extend downward against the patient's body once the distal portion of the catheter assembly has been placed in the vasculature.

Both FIGS. 1 and 2 further include a distal tip region, generally designated at 20, that is configured in accordance one example embodiment of the present invention, the details of which are given below. It should be appreciated that the distal tip region to be described below can be included with hemodialysis catheters, such as those shown in FIGS. 1 and 2, or with other catheters, such as central venous catheters, for example.

Figure 3C:
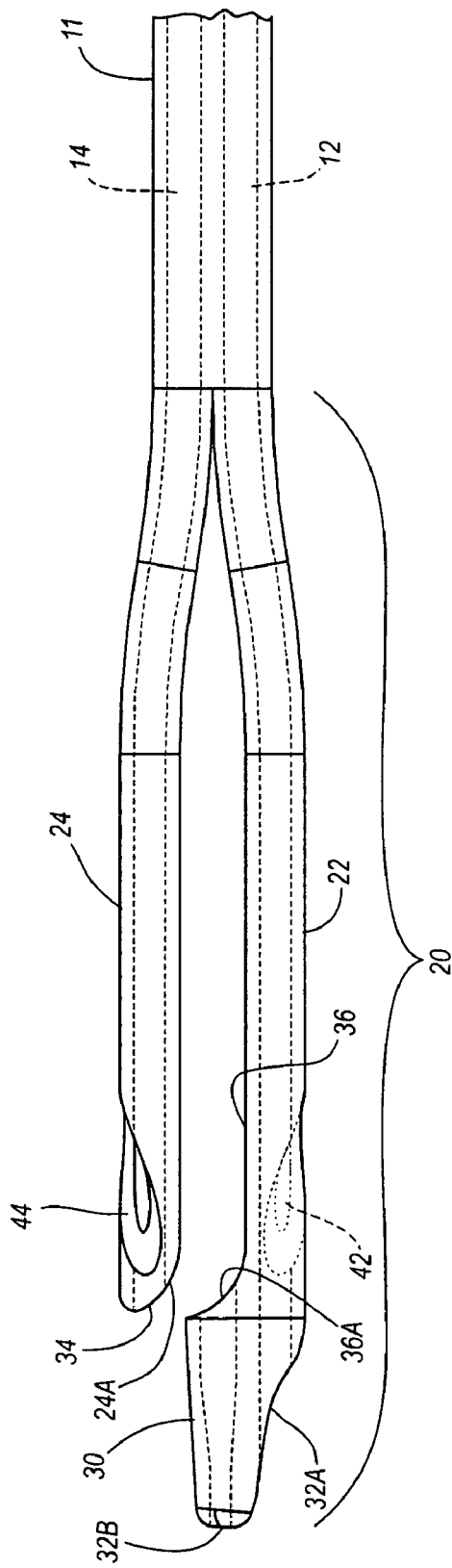

Reference is now made to FIGS. 3A-3D, which depict various details regarding the distal tip region 20 of FIG. 1 as briefly discussed above. The distal tip region 20 generally includes the split-tip distal portion of the catheter assembly 10, including a distal venous segment 22 that defines a distal portion of the first lumen 12, and a distal arterial segment 24 that defines a distal portion of the second lumen 14. As shown in FIG. 3B, the venous and arterial segments 22, 24 are split along a common septum of the catheter body 11 that separates the first lumen 12 from the second lumen 14.

The venous segment 22 includes a nose portion 30 at the distal end thereof. In the present embodiment, the nose portion 30 generally defines a tapered, conical shape, though this shape may be varied, as will be seen further below. The tapered shape of the nose portion 30 reduces insertion forces during placement and minimizes abrasion between the nose portion surface and the walls of the vessel in which the distal region of the catheter is disposed. A venous distal opening 32A is defined on the tapered portion of the nose portion 30 and is in fluid communication with the distal portion of the first lumen 12 defined by the venous segment. A guidewire channel 32B proximally extends from a hole defined at the distal end of the nose portion 30 and is in communication with the second lumen 14 of the arterial segment 24, in the manner described below, to enable selective nesting of the arterial segment with the venous segment 22 during catheter insertion. Of course, these openings, as well as the other catheter openings to be described below, can vary in size and placement from what is explicitly described herein.

The venous segment 22 further defines a recess 36 proximal to the nose portion 30 that is sized to correspond to the shape of an outer surface of the arterial segment 24. The arterial segment 24 can thus be selectively and removably seated, or "nested" in the recess 36, thus providing a smooth, cylindrical outer surface profile for the distal tip region 20 of the catheter body 11 during advancement of the catheter assembly 10 through a subcutaneous tunnel or vasculature path.

In greater detail, and as best seen in FIG. 3C, the recess 36 defines a concavely shaped distal surface 36A that corresponds to the convex shape of a distal surface 24A of the arterial segment 24. Note that an upper portion of the curved distal surface 24A is rounded so as to reduce snagging of the arterial segment 24 during vasculature navigation.

Figure 4A:
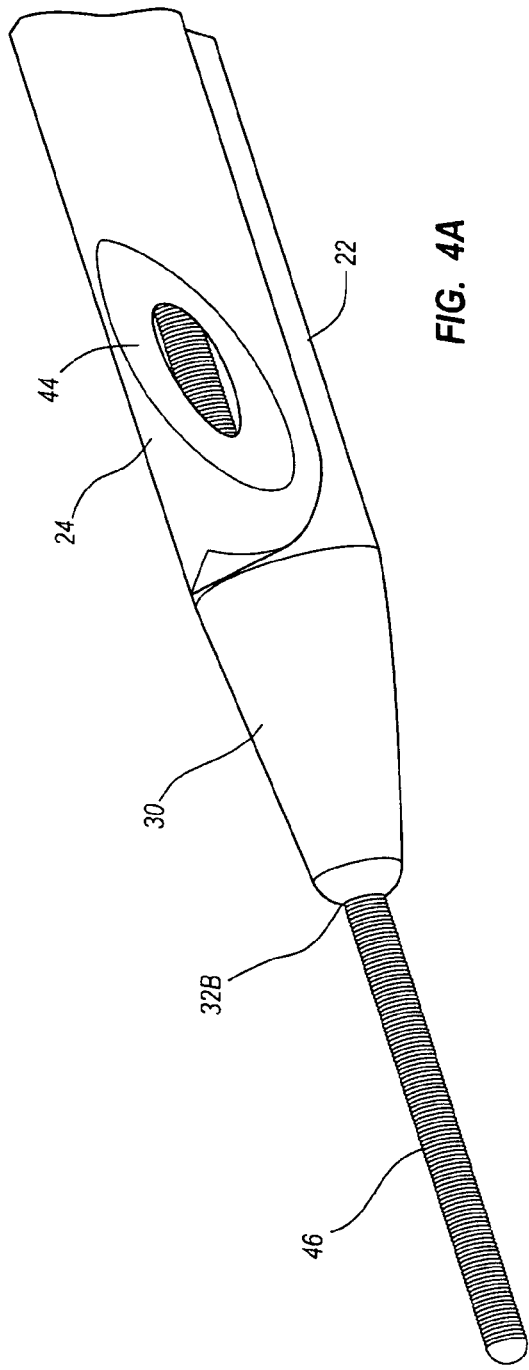
FIGS. 4A and 4B are a perspective and a side view, respectively, of the distal region of the split-tip catheter of FIG. 1, wherein a guidewire is inserted therethrough to maintain a venous segment and arterial segment in a nested configuration.
Figure 4B:
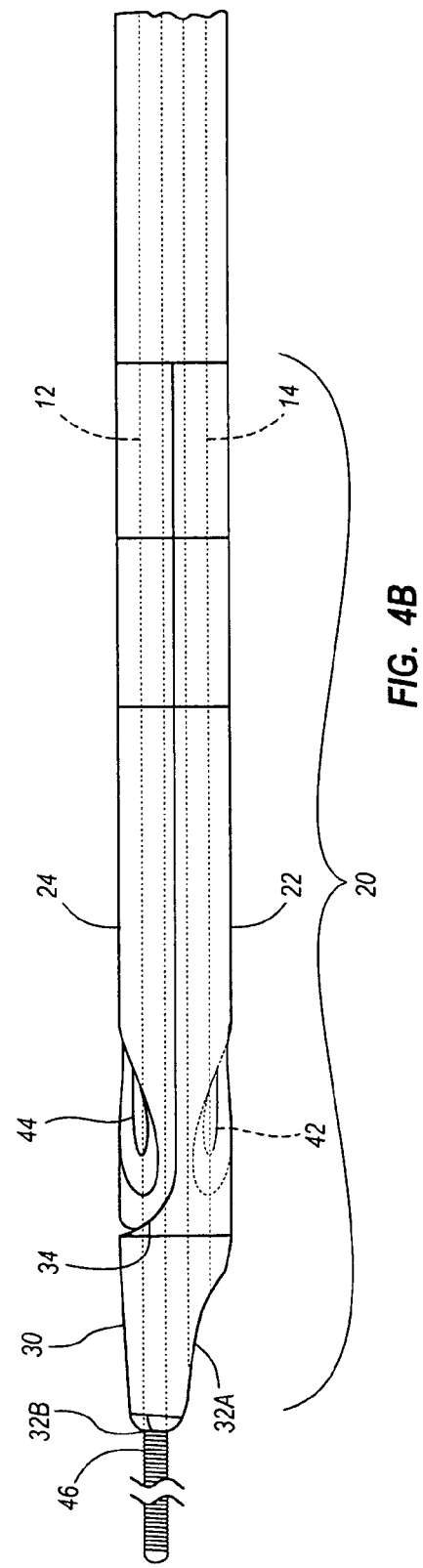

A distal end of the arterial segment 24 includes an arterial distal end opening 34, which is defined on the curved distal end opening surface 24A thereof. The arterial distal end opening 34 is in fluid communication with the distal portion of the arterial lumen 14 defined by the arterial segment 24. In addition, the arterial distal end opening 34 coaxially aligns with the guidewire channel 32B of the venous nose portion 30 when the arterial segment 24 is nested and seated in the recess 36 of the venous segment 22. So positioned, a guidewire 46 can be passed through the guidewire channel 32B of the venous nose portion 30, the arterial distal end opening 34, and the second lumen 14, as shown in FIGS. 4A and 4B, to maintain the arterial segment 24 in a nested configuration in the recess 36 of the venous segment 22. This nested configuration can be achieved in other ways as well, including in one embodiment a bio-dissolvable adhesive that temporarily binds the two segments together until catheter placement within the vasculature is complete, after which the adhesive dissolves to enable the segments to separate.

With the arterial segment 24 nested in the recess 36 behind the venous nose portion 30, the distal tip region 20 of the catheter assembly 10 presents as a low drag, columnar structure with a tapered nose configuration. This configuration aids in guiding the distal tip region 20 through the soft tissues and vasculature of the patient during placement or catheter exchange procedures using over-the-wire techniques for instance. Later, when the catheter assembly 10 is properly positioned, the venous segment 22 and the arterial segment 24 can separate from one another within the vessel, as shown in FIG. 3C for example, as a result of removal of a guidewire used to position the catheter. This separation of the venous and arterial segments 22 and 24 assists in reducing recirculation of treated blood during hemodialysis procedures. Note here that, in another embodiment, the nesting configuration of the distal tip region could be interchanged such that the recess is defined by the arterial lumen and the venous lumen nests therein.

FIGS. 3A-3D further depict the venous segment 22 as including along its length a venous lateral opening 42 defined proximate the nose portion 30. Similarly, the arterial segment 24 includes an arterial lateral opening 44 defined proximate the distal end of the arterial segment 24. The lateral openings 42 and 44 can take various shapes and configurations as will be shown further below, but in the present embodiment the lateral openings are defined by compound-angle cross-drilled cuts through the outer surface of the respective segment 22 or 24 to establish communication with the respective first or second lumens 12, 14. In one embodiment, such cuts are referred to as "skive" cuts.

In one embodiment, the longitudinal axis of each cross cut of the lateral openings 42, 44 defines an angle of about 35 degrees with a longitudinal axis of the respective venous or arterial segment 22, 24, though this angle can vary in one embodiment from about 20 to about 90 degrees. The longitudinal axis of each cross cut of the lateral openings 42, 44 further defines an angle in one embodiment of about 15 degrees with a plane bisecting the first lumen 12 and second lumen 14, i.e., coplanar with the septum separating the first and second lumens proximal of the distal tip region 20, though this angle can vary in one embodiment from about 0 to about 45 degrees. This angular character imparts a lateral directional component to fluid flow out of either lateral opening 42, 44, as represented by the flow arrows in FIG. 3D.

Figure 3D:
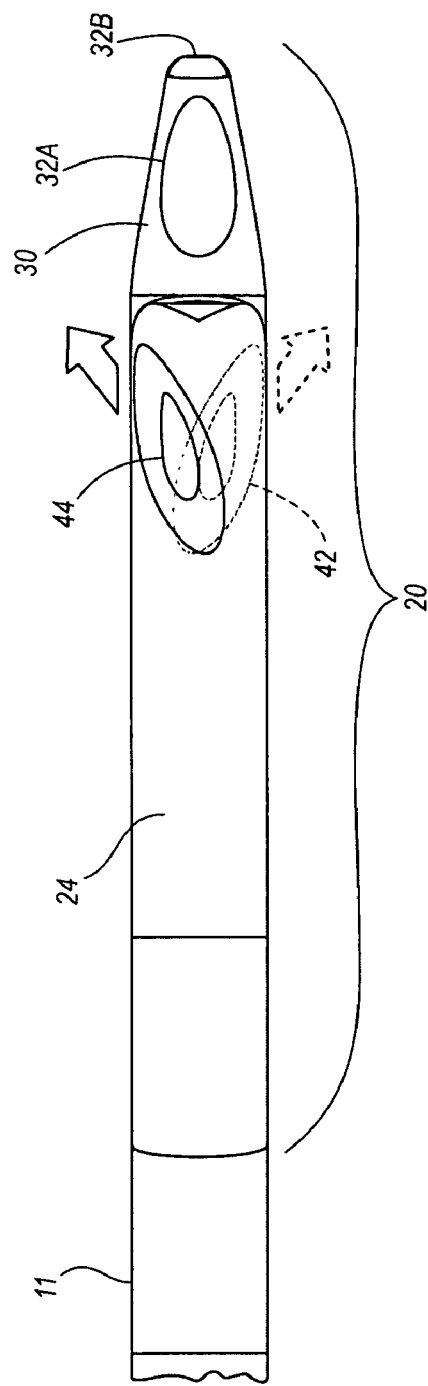

In addition, the longitudinal axes of the lateral openings 42, 44 are symmetrically opposed in direction from one another, as best shown in FIG. 3D, so as to ensure fluid entry and exit from the lateral openings occurs on opposite sides of catheter assembly 10, thus reducing recirculation of already treated blood. Furthermore, this symmetry ensures similar fluid flow characteristics to be realized even when fluid flow through the catheter assembly 10 is reversed. Moreover, the lateral openings 42, 44 extend circumferentially about a portion of the circumference of the respective venous or arterial segment 22 or 24, thus helping to prevent aspiration-related suck-up of the segment against the vessel wall. It is noted that in one embodiment the size of the lateral openings 42, 44 is such that each can accommodate the entirety of fluid flow through their respective first or second lumens 12, 14. Thus, the inclusion of the lateral openings 42, 44 with their corresponding distal openings 32A, 34 provides a redundant system such that any clotting that occurs at one opening will not significantly impact fluid throughput of the respective venous or arterial segment.

It should be appreciated that the labels "venous" and "arterial" as used above in describing the various components of the present split-tip catheter are employed for sake of convenience in describing aspects of embodiments of the present invention. Indeed, though the arterial segment is normally employed in hemodialysis procedures for aspirating blood from the blood vessel in which the catheter is disposed and the venous segment for returning already treated blood to the vessel, this can be reversed such that blood is returned via the arterial segment and aspirated by the venous segment. As such, the present invention should not be considered limited by the use of this and other descriptive terminology herein.

As can be seen in FIGS. 3D and 4B, the nose portion 30 of the venous segment 22 is configured such that it provides a "shadow" for the arterial segment 24 when the arterial segment is brought into contact with the venous segment, such as when it seats in the recess 36 of the venous segment. In other words, the outer diameter of the nose portion 30 is similar to that of the catheter body 11 proximal of the distal tip region 20 such that the arterial segment 24 is "shielded" by the nose portion when nested with the recess 36. This provides for relative ease of catheter insertion, such as when the distal tip region 20 is passed through a valved introducer during initial catheter placement, or through a subcutaneous tunnel in an over-the-guidewire catheter exchange procedure.

In one embodiment, the nose portion 30 is defined via a radiofrequency ("RF") tipping process, wherein a dual lumen catheter is split to define two lumen segments, i.e., the venous and arterial segments, in a distal tip region thereof. The distal portions of the lumen segments are bonded together via RF tipping to define the shape of the nose portion as shown in FIGS. 3A-3D. The distal tip region is then sliced to define the recess 36 and separate the arterial segment from the venous segment. Note that other forming processes may also be employed to define the distal tip region in accordance with other embodiments and as appreciated by one skilled in the art.

Reference is now made to FIGS. 5A and 5B in describing flow characteristics with respect to the split-tip configuration of the distal tip region 20 of the present catheter assembly 10. FIGS. 5A and 5B shows the distal tip region 20 with the arterial segment 24 in its unseated state with respect to the venous segment 22 after the catheter assembly 10 has properly positioned within a vessel of a patient. Arrow 48 shows the direction of bloodflow past the distal tip region 20 within the patient's vessel.

In greater detail, FIG. 5A shows fluid flow through the distal tip region 20 in a "forward" direction, wherein blood is aspirated by the second lumen 14, or "uptake" lumen, for removal from the body and treatment by a hemodialysis apparatus or for some other suitable purpose. Aspirated blood enters the second lumen 14 via both the arterial distal end opening 34 and the arterial lateral opening 44 of the arterial segment 24. However, because the second lumen 14 is under negative pressure during aspiration, the majority of blood aspirated by the second lumen is removed via the arterial lateral opening 44 due to its relatively more proximal position with respect to the pressure differential in the proximate vessel region.

Similarly, blood is infused, or returned, to the vessel by the first lumen 12, or "return" lumen, after treatment by a hemodialysis apparatus or some other suitable purpose. Infused blood exits the first lumen 12 from both the venous distal opening 32A and the venous lateral opening 42 of the venous segment 22. However, because the second lumen 12 is under positive pressure during infusion, the majority of blood returned to the bloodstream by the first lumen exits via the venous distal opening 32A due to its relatively more distal position with respect to the pressure differential in the proximate vessel region. Note that this arrangement produces an effective stagger distance F in the "forward" direction between the primary aspiration site, i.e., the arterial lateral opening 44, and the primary infusion site, i.e., the venous distal opening 32A. This effective stagger distance, together with the lateral orientation of the lateral openings 42, 44 provides for low recirculation of already-treated blood within the vessel, recirculation being defined as already-treated blood that is returned to the bloodstream via the venous lumen being immediately aspirated by the arterial lumen to be retreated. Such recirculation is undesirable as it results in lower treatment efficiency and longer treatment time.

During hemodialysis procedures, it is sometimes necessary to reverse the blood flow through the catheter assembly 10. FIG. 5B shows fluid flow through the distal tip region 20 during such a "reverse" flow situation. In contrast to the forward flow conditions of FIG. 5A, the second lumen 14 in FIG. 5B is employed to infuse blood into the vessel via the arterial lumen 24, while the first lumen 12 aspirates blood from the vessel via the venous lumen 22. In this configuration, the majority of infused blood enters the vessel via the arterial distal opening 34 of the arterial segment 24, while the majority of aspirated blood is removed via the venous lateral opening 42 of the venous segment 22. This arrangement produces an effective stagger distance R in the "reverse" direction between the primary aspiration site, i.e., the venous lateral opening 42, and the primary infusion site, i.e., the arterial distal opening 34. Thus, it is seen that a desired stagger between the primary infusion and aspiration points is achieved regardless of the direction in which the catheter is operating.

Reference is now made to FIGS. 5C-5H. In one embodiment, the proximal portions of the first and second lumens 12, 14 of the catheter body 11 define a "D"-shaped cross sectional shape, as seen in FIGS. 5D and 5E. The first and second lumens 12, 14 each include a loft, or transition region 45, wherein the cross sectional shape of each lumen changes from a "D" shape to an oval shape, which oval shape continues toward the distal end of the distal tip region 20, as seen in FIGS. 5F and 5G. Definition of the transition region 45 and the oval shape of the distal portions of the first and second lumens 12, 14 can be accomplished by one of several suitable methods, including heat forming, molding, extrusion, etc.

Note that the oval shape of the first and second lumens 12, 14 is provided in the region proximate the lateral openings 42, 44. This provides additional stiffness and strength to the catheter body 11 in this region while also maintaining an acceptable inter-luminal thickness for the central septa of the venous and arterial segments 22, 24. In other embodiments, other cross sectional shapes can be defined by the catheter body. Or, in another embodiment the "D"-shaped cross sectional lumens continue distally to the distal end of the catheter body. In yet another embodiment, the first and second lumens define oval cross sectional shapes along most or all of the catheter body length. FIG. 5H shows an end view of the catheter body depicted in FIG. 5C.

Figure 6A:
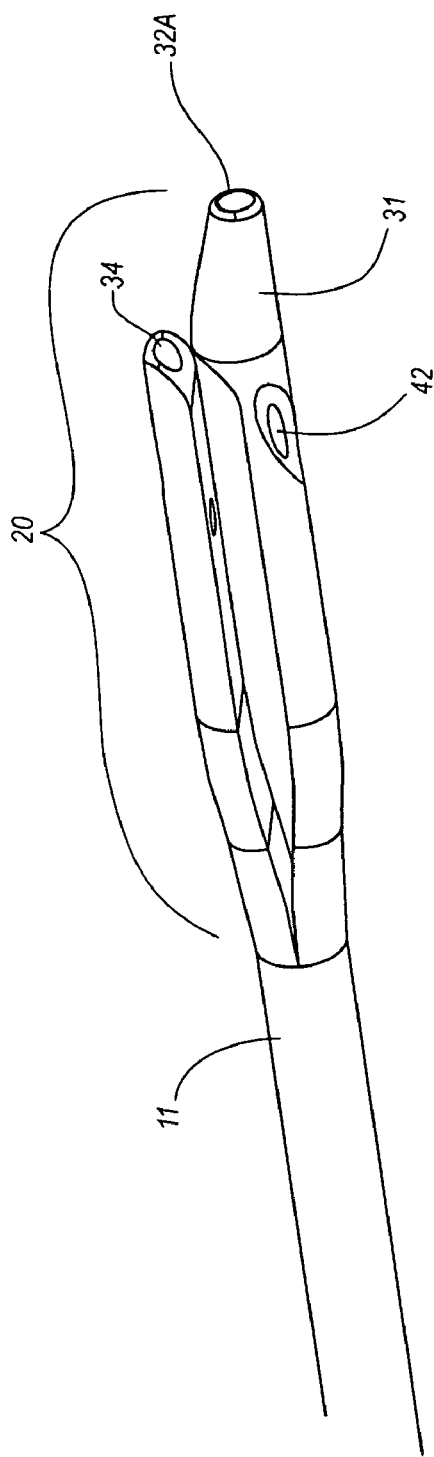
FIGS. 6A and 6B are a perspective and a side view, respectively, of a distal region of a split-tip catheter configured in accordance with one embodiment.
Figure 6B:
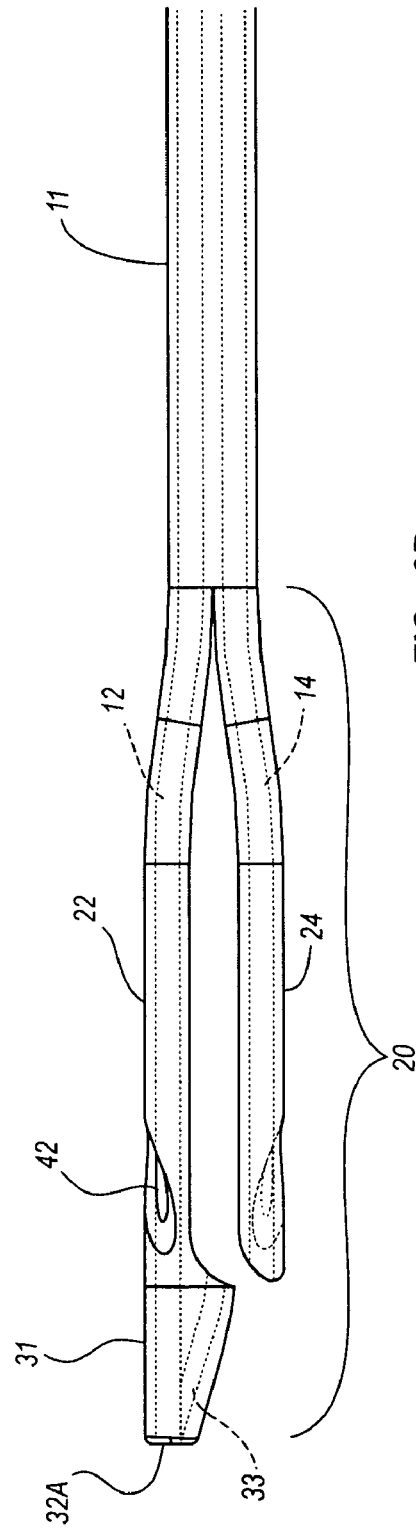

Note that the configuration of the distal tip region 20 can vary according to need or design. FIGS. 6A and 6B show one such variation, wherein a nose portion 31 of the venous segment 22 includes the venous distal opening 32A at the distal end of the nose portion and not along the tapered surface, as in the configuration in FIG. 1. Further, a guidewire channel 33 extends from just inside the venous distal opening 32A and through the nose portion 31 so as to establish communication with the arterial distal opening 34 of the arterial segment 24 when the arterial and venous segment 22 are nested. Thus, these and other variations in the distal tip region are contemplated as falling within the principles of the present invention.

Figure 7:
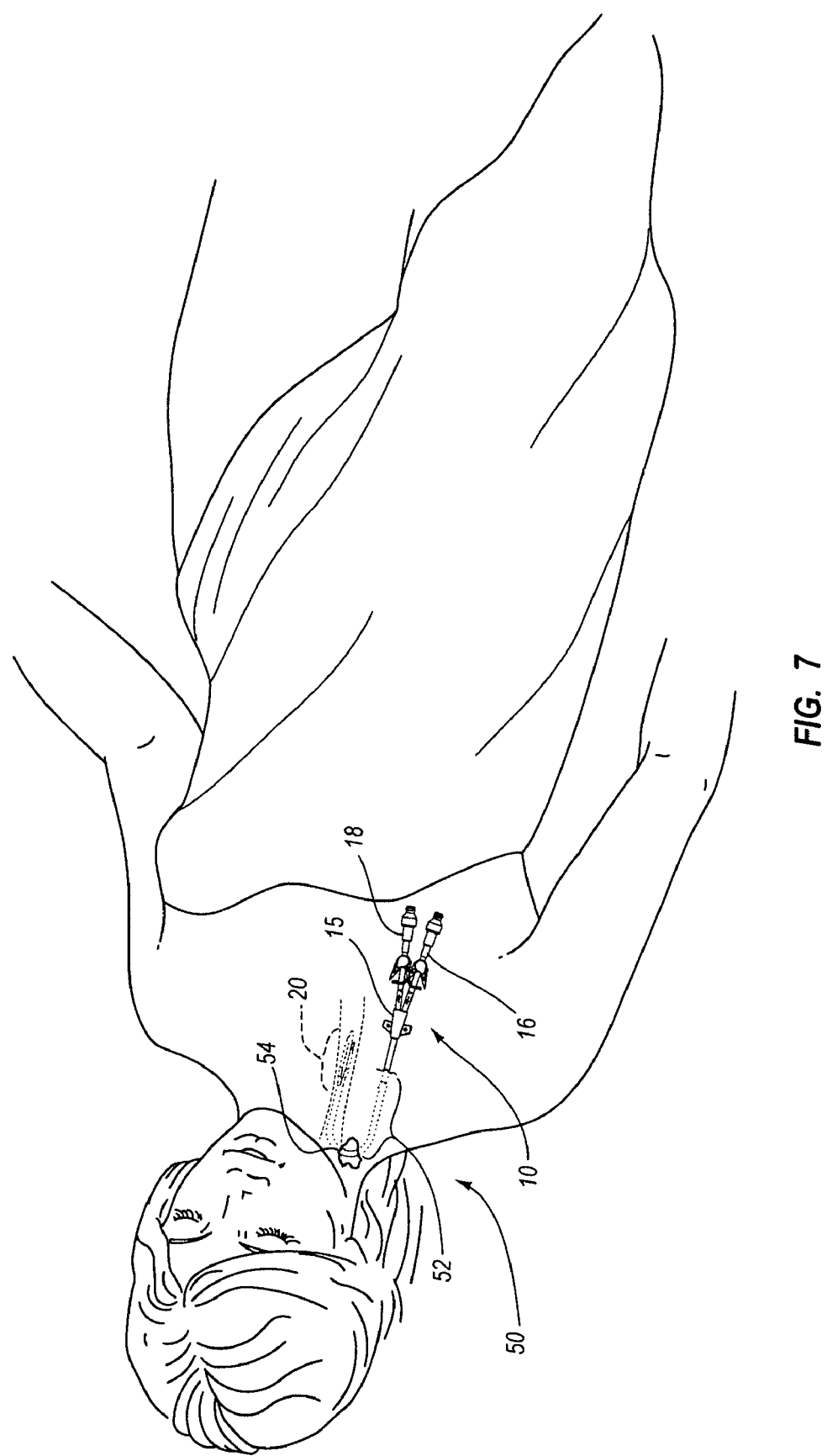
FIG. 7 is a simplified view of the split-tip catheter of FIG. 1 after insertion into a vasculature of a patient.
Figures 8B, 8C, 8D:
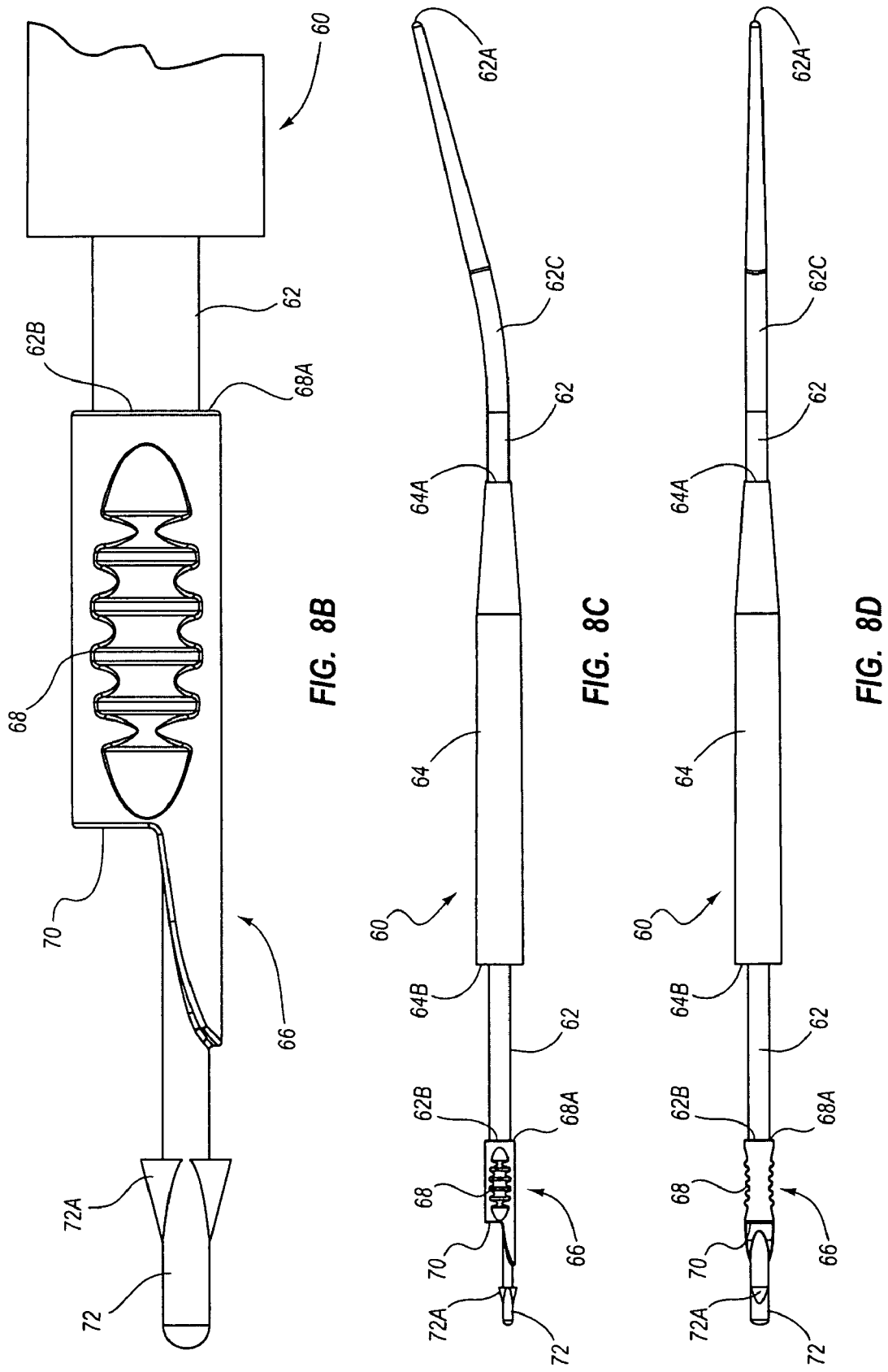
FIG. 8B is a side view of the tunneler shown in FIG. 8A.
FIGS. 8C and 8D are side and top views, respectively, of the tunneler shown in FIG. 8A.

Reference is now made to FIGS. 8A-8D in describing various aspects of a subcutaneous tunneling device ("tunneler"), generally designated at 60, for use in subcutaneously tunneling a portion of the catheter assembly 10 in the body of the patient. FIG. 7 depicts such a tunneled state of the catheter assembly 10, wherein a tunneled region 52 intermediate the proximal and distal ends of the catheter body 11 is disposed underneath the skin of the patient 50. As shown, the proximal portion of the catheter assembly 10, including the hub 15 and extension legs 16 and 18, is exposed proximal the tunneled region 52. Correspondingly, a distal portion of the catheter assembly 10 is shown distal of the tunneled region 52 and inserted through an incision site 54 into the patient's vasculature such that the distal tip region 20 is positioned in a desired location, such as in a lower region of the superior vena cave ("SVC"). The cuff 19 (FIG. 1) is included in the tunneled region 52 of the catheter assembly 10 such that tissue ingrowth into the cuff may be achieved to subcutaneously anchor the catheter to the patient's body and prevent unintended movement of the catheter. The process by which the tunneling configuration shown in FIG. 7 is achieved is referred to as antegrade tunneling.

As shown in FIGS. 8A-8D, the tunneler 60 generally includes shaft 62, a sleeve 64 slidably mounted on the shaft, and a catheter connector 66. Composed of materials including malleable stainless steel or other suitable material, the shaft 62 is used during the tunneling procedure to define the tunnel through which the catheter will be pulled. The shaft 62 tapers down to a first end 62A and includes a second end 62B at which end the catheter connector 64 is attached. The shaft includes a bend 62C, which acts as a slide stop for the sleeve 64.

The sleeve 64 is composed of materials including flexible plastic e.g., polyethylene for instance, and includes a hollow inner bore 74 (FIG. 9D) that slidably receives the shaft 62 therethrough. The inner bore 74 of the sleeve 64 extends between a tapered down first end 64A and a second end 64B that is sized to selectively slide over the catheter connector 66. Thus, the sleeve 64 is selectively slidable from a retracted position, in which the tapered first end 64A stops against the shaft bend 62C, and an extended position, in which the sleeve covers the entirety of the catheter connector 66.

Composed of materials including biocompatible plastic for instance, the catheter connector 66 includes a body defining a gripping portion 68 for enabling a clinician to grasp the tunneler 60, and a stepped end 68A at the point of attachment of the catheter connector with the second end 62B of the shaft 62. A nose stop 70 is included on the catheter connector 66 and is shaped as to correspond with the distal portion of the catheter to which the catheter connector will attach. As will be seen, this enables a clinician to know when the catheter connector has fully engaged the catheter prior to tunneling.

A barbed extension 72 including one or more barbs 72A extends from the catheter connector nose stop 70 and is configured to extend into a lumen of the catheter to which the tunneler 60 will connect so as to provide a retention force therebetween. Note that the barbed extension 72 is offset from a central longitudinal axis of the catheter connector 66, though this configuration may be modified according to the design of the catheter to which the catheter connector is to connect.

Reference is now made to FIGS. 9A-9D in describing the manner of attachment between the tunneler 60 and a distal end of a catheter, such as the catheter assembly 10 shown in FIG. 1. Particularly, FIG. 9A shows the alignment between a distal end of the catheter assembly 10 and the tunneler 60, wherein the barbed extension 72 is axially aligned with the venous distal opening 32A of the venous segment 22 prior to insertion of the barbed extension into the catheter.

FIG. 9B shows the barbed extension 72 fully inserted into the venous distal opening 32A, thus connecting the tunneler 60 with the catheter assembly 10. In this position, the nose portion 30 of the venous segment 22 engages the nose stop 70 of the catheter connector 66, thus enabling the clinician to determine when the connector is fully engaged with the catheter assembly 10. Note that the barb 72A of the barbed extension 72 engages the first lumen 12 via the venous distal opening 32A such that the outer surface of the segment is extended outward in the immediate vicinity of the barb.

As shown in FIG. 9C, once the catheter connector 66 of the tunneler 60 is fully connected to the distal end of the catheter assembly 10, the sleeve 64 is slid forward to cover the entirety of the catheter connector and its engagement with the catheter. As shown in FIG. 9D, the sleeve is slid forward until a shoulder 76 defined in the inner bore 74 abuts the stepped end 68A of the catheter connector. Note that the sleeve inner bore 74 is sized so as to compress the distal portion of the catheter proximate its engagement with the catheter connector 66, thus increasing engagement of the barb 72A with the first lumen 12.

So attached, the tunneler 60 can then be used to define a subcutaneous tunnel in the patient and pull the catheter assembly 10 through the tunnel until properly positioned therein, as shown in FIG. 7. Once the catheter assembly 10 is properly positioned, the sleeve 64 can be slid back to expose the catheter connector 66. The catheter connector 66 can then be pulled so as to remove the barbed extension 72 from the first lumen 12 of the venous segment 22, thus disconnecting the tunneler 60 from the catheter assembly 10.

Note that the catheter connector 66 and its barbed extension 72 are configured to provide a retention force sufficient to enable the catheter assembly 10 to be pulled by the tunneler through the subcutaneous tunnel, but low enough to prevent damaging tensile loads from being imposed on the distal end of the catheter. As such, the catheter connector 66 is configured such that it can pulled out from the engagement with the catheter assembly 10 at a predetermined tensile load that is below the maximum tensile strength of the catheter distal end. Note also that engagement of the tunneler 60 with the catheter assembly 10 as depicted herein is merely exemplary, and it is appreciated that the present tunneler can be employed with catheters having a variety of configurations.

Figure 11:
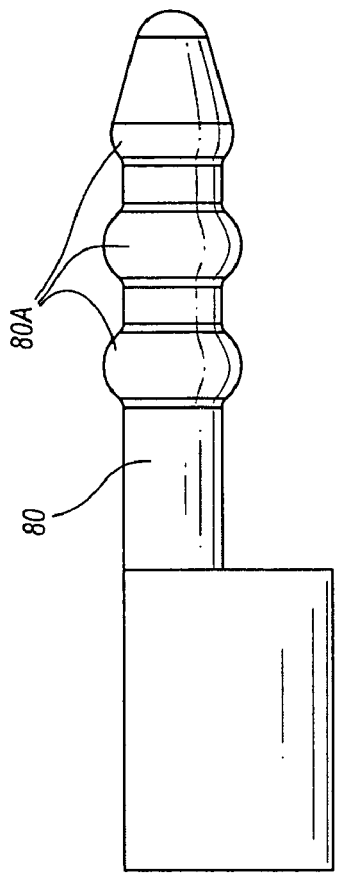
FIGS. 10-12 are side views of barb configurations for the tunneler of FIG. 8A, according to embodiments of the present invention.
Figure 12:
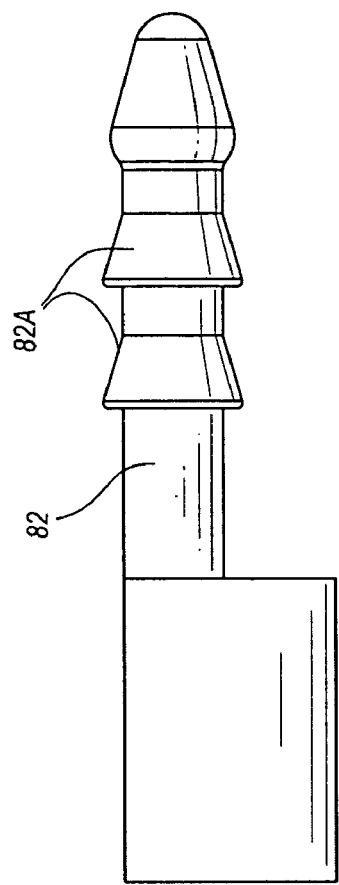
Figure 10:
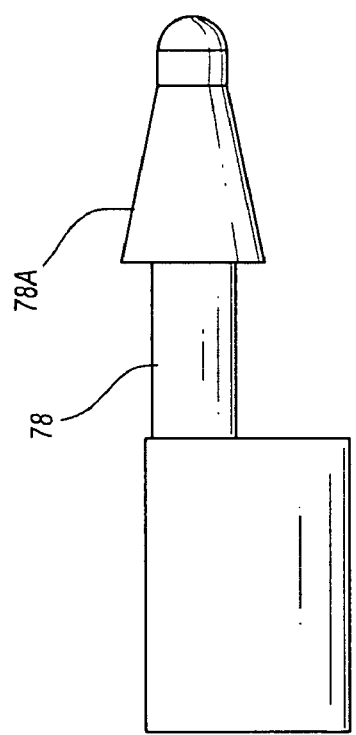

It should be further appreciated that the tunneler configuration can be varied according to need or design. FIGS. 10-12 give examples of alternative barbed extensions 78, 80, and 82, each having a different configuration of barb(s) 78A, 80A, and 82A, respectively. These and other modifications to the tunneler 60 are therefore contemplated as falling within the principles of the present invention. In addition, it is noted that the catheter assembly may be employed in both tunneled and untunneled implementations, if desired.

Reference is now generally made to FIGS. 13A-21C in depicting varying configurations of a split-tip catheter assembly in accordance with additional example embodiments of the present invention. As the embodiments to be described below include elements similar to those described in connection with the catheter assemblies described above in connection with FIGS. 1-5B, only selected elements of the following embodiments will be discussed below.

Figure 13A:
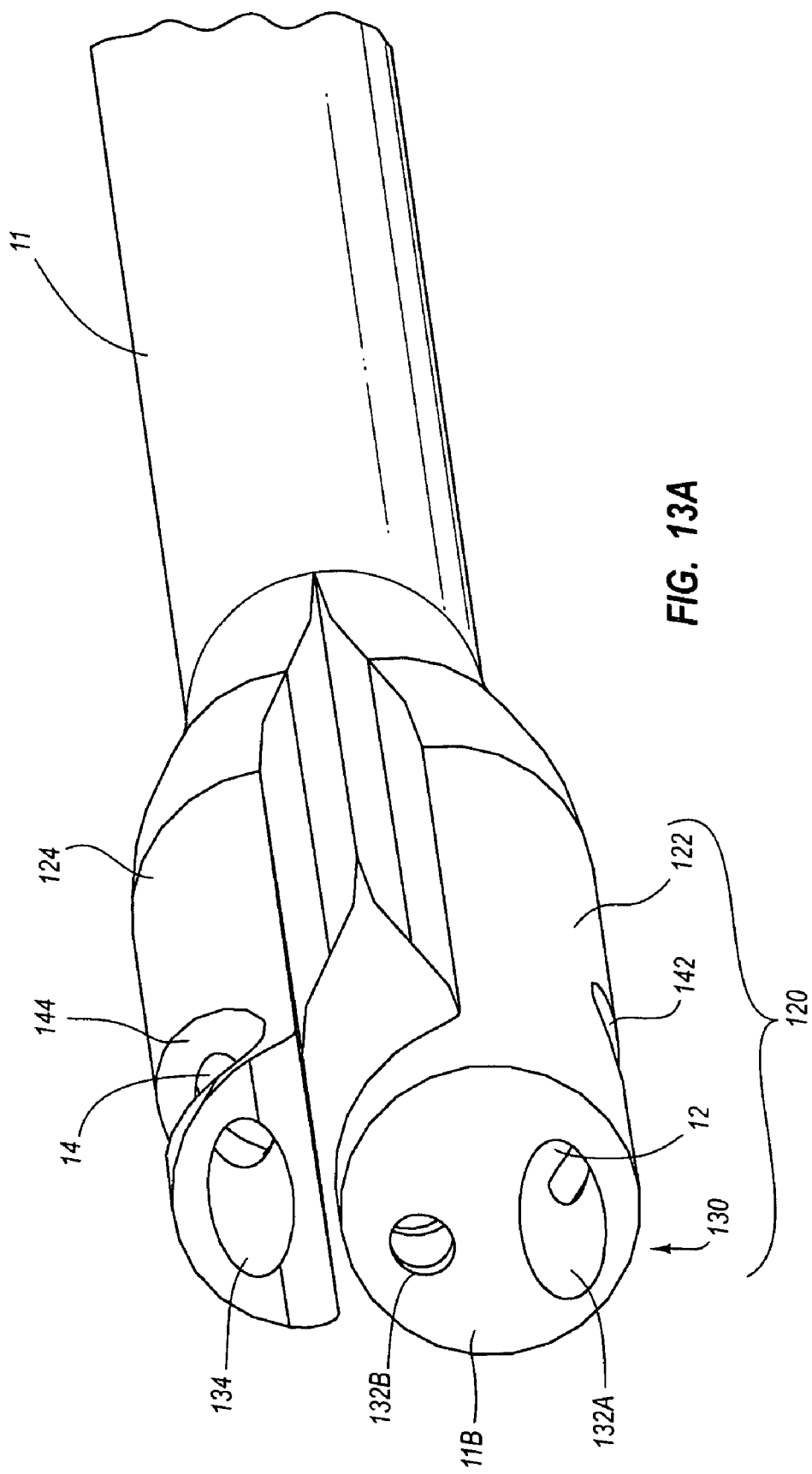

FIGS. 13A-13C depict a distal tip region 120 of a split-tip catheter assembly including a venous segment 122 and an arterial segment 124 that selectively seats, or nests, in a recess defined by the venous segment. A nose portion 130 of the venous segment 122 includes a venous distal opening 132A in fluid communication with a first lumen of the catheter body 11 and a guidewire channel 132B. The arterial segment 124 includes an arterial distal opening 134 in fluid communication with a second lumen of the catheter body 11. The arterial segment 124 is further in communication with the guidewire channel 132B when the arterial segment is nested with the venous segment 122.

The venous segment 122 includes a venous lateral opening 142 proximate the nose portion 130, while the arterial segment 124 includes an arterial lateral opening 144 proximate the distal end thereof. The lateral openings 142 and 144 are cross-cut, or skived in a manner similar to the embodiment shown in FIG. 1 and are in fluid communication with the first and second lumens, respectively, of the catheter body 11. Note that the nose portion 130 of the present embodiment has a rounded shape, in contrast to the tapered nose portion 30 of FIG. 1, though it is appreciated that various nose portion shape configurations are possible.

FIGS. 14A-14C depict a distal tip region 220 of a split-tip catheter assembly including a venous segment 222 and an arterial segment 224 that selectively seats, or nests, in a recess defined by the venous segment. A nose portion 230 of the venous segment 222 includes a nose portion opening 232 that serves as a guidewire channel by virtue of its alignment with an arterial distal opening 234 of the arterial segment 224 when the latter is nested with the venous segment 222. The arterial distal opening 234 is further in fluid communication with a second lumen of the catheter body 11. As such, a guidewire passing through the second lumen, the arterial distal opening 234 and the guidewire channel of the nose portion opening 232 enables the venous and arterial segments 222, 224 to be maintained in a nested configuration during catheter insertion.

The venous segment 222 includes a venous lateral opening 242 proximate the nose portion 230, while the arterial segment 224 includes an arterial opening 248 proximate the distal end thereof. The lateral opening 242 is cross-cut, or skived in a manner similar to the embodiment shown in FIG. 1, while the arterial opening 248 defines a triangular opening. The openings 242, 248 are in fluid communication with the first and second lumens, respectively, of the catheter body 11. The nose portion 230 of the present embodiment has a rounded shape, in contrast to the tapered nose portion 30 of FIG. 1, though it is appreciated that various nose portion shape configurations are possible. Also, it is appreciated that the openings can each define one of a variety of configurations.

Figure 15A:
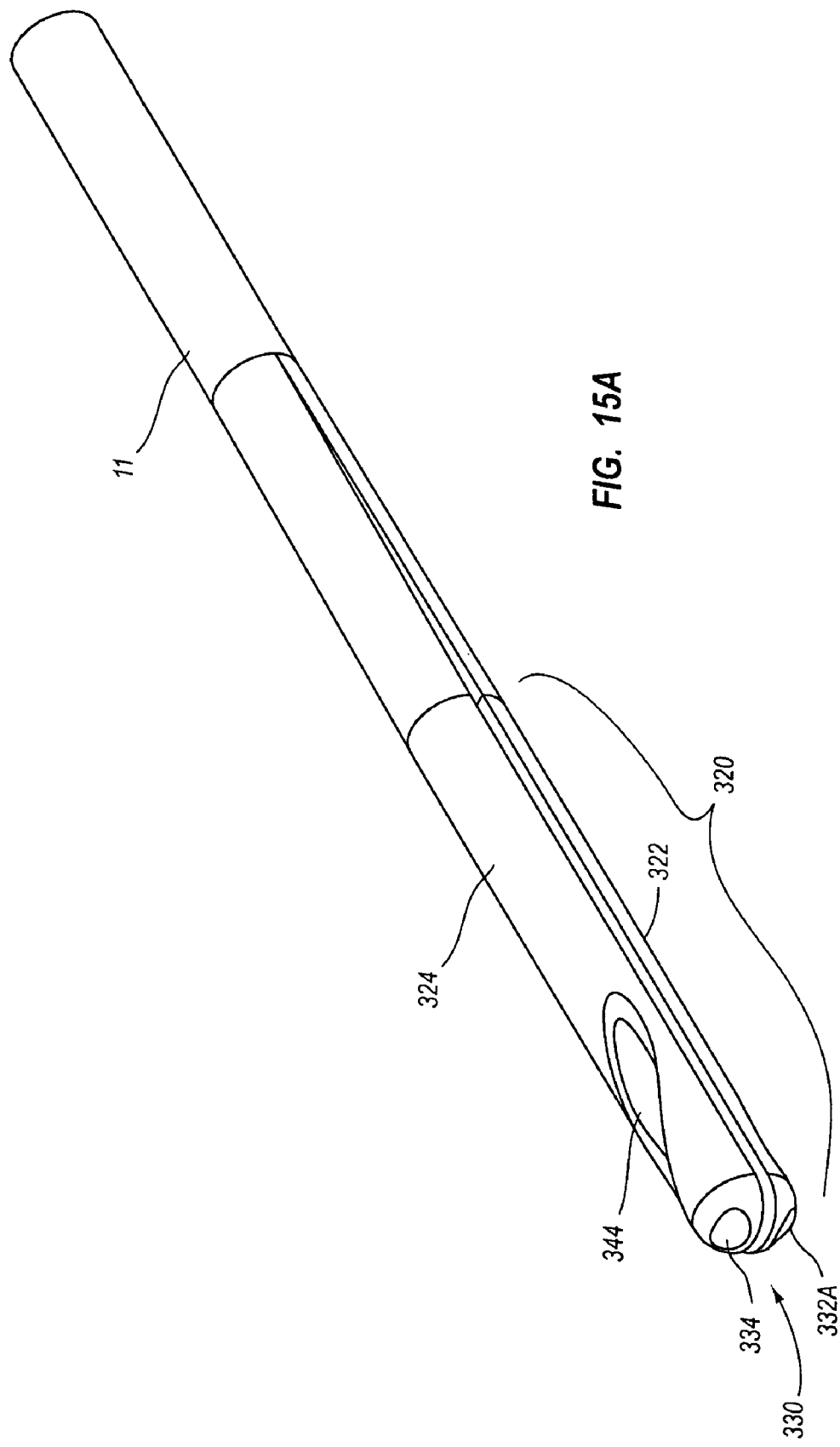
FIGS. 15A-15C are perspective, bottom, and top views, respectively, of a split-tip catheter including a distal region configured in accordance with one embodiment.
Figure 15B:
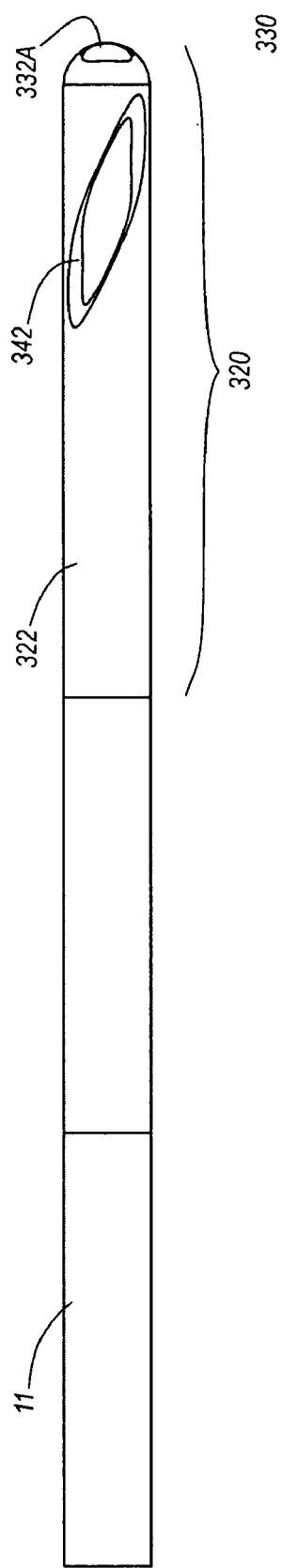
Figure 15C:
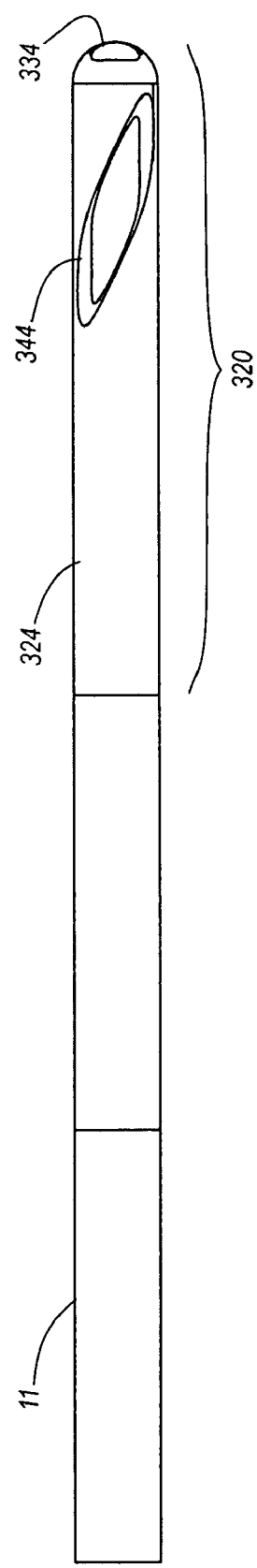

FIGS. 15A-15C depict a distal tip region 320 of a split-tip catheter assembly including a venous segment 322 and an arterial segment 324 that together define a nose portion 330. The venous segment 322 includes a venous distal opening 332A in fluid communication with a first lumen of the catheter body 11. The arterial segment 324 includes an arterial distal opening 334 in fluid communication with a second lumen of the catheter body 11.

The venous segment 322 includes a venous lateral opening 342 proximate the nose portion 330, while the arterial segment 324 includes an arterial lateral opening 344 proximate the distal end thereof. The lateral openings 342, 344 are cross-cut, or skived in a manner similar to the embodiment shown in FIG. 1. The lateral openings 342, 344 are in fluid communication with the first and second lumens, respectively, of the catheter body 11. The distal ends of the venous segment 322 and arterial segment 324 are un-staggered with respect to one another so as to enable both lateral openings to be placed in a single desired location within the patient's vasculature, such as in the SVC for instance.

The nose portion 330 of the present embodiment has a rounded shape, in contrast to the tapered nose portion 30 of FIG. 1, though it is appreciated that various nose portion shape configurations are possible. Also, it is appreciated that the lateral openings can each define one of a variety of configurations.

Figure 16A:
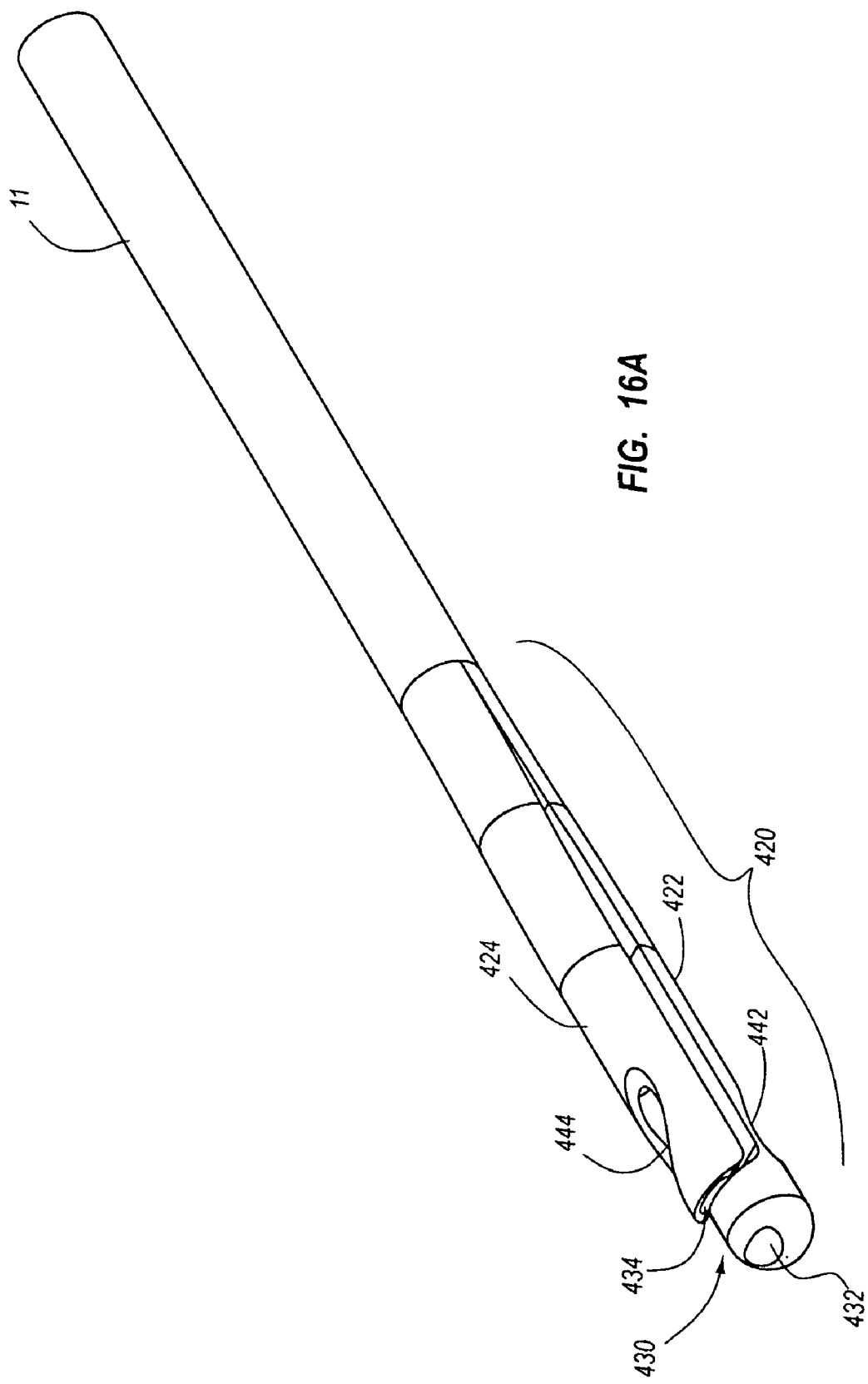

FIGS. 16A-16C depict a distal tip region 420 of a split-tip catheter assembly including a venous segment 422 and an arterial segment 424 that selectively seats, or nests, in a recess defined by the venous segment. A nose portion 430 of the venous segment 422 includes a nose portion opening 432 that serves as a guidewire channel by virtue of its alignment with an arterial distal opening 434 of the arterial segment 424 when the latter is nested with the venous segment 422. The arterial distal opening 434 is further in fluid communication with a second lumen of the catheter body 11. As such, a guidewire passing through the second lumen, the arterial distal opening 434 and the guidewire channel of the nose portion opening 432 enables the venous and arterial segments 422, 424 to be maintained in a nested configuration during catheter insertion.

The venous segment 422 includes a venous lateral opening 442 proximate the nose portion 430, while the arterial segment 424 includes an arterial lateral opening 444 proximate the distal end thereof. The lateral openings 442, 444 are cross-cut, or skived in a manner similar to the embodiment shown in FIG. 1. The lateral openings 442, 444 are in fluid communication with the first and second lumens, respectively, of the catheter body 11. The nose portion 430 of the present embodiment has a rounded shape, in contrast to the tapered nose portion 30 of FIG. 1, though it is appreciated that various nose portion shape configurations are possible. Also, it is appreciated that the lateral openings can each define one of a variety of configurations.

FIGS. 17A-17C depict a distal tip region 520 of a split-tip catheter assembly including a venous segment 522 and an arterial segment 524 that selectively seats, or nests, in a recess defined by the venous segment. A nose portion 530 of the venous segment 522 includes a nose portion opening 532 that serves as a guidewire channel by virtue of its alignment with an arterial distal opening 534 of the arterial segment 524 when the latter is nested with the venous segment 522. The arterial distal opening 534 is further in fluid communication with a second lumen of the catheter body 11. As such, a guidewire passing through the second lumen, the arterial distal opening 534 and the guidewire channel of the nose portion opening 532 enables the venous and arterial segments 522, 524 to be maintained in a nested configuration during catheter insertion.

The venous segment 522 includes a venous lateral opening 542 proximate the nose portion 430, while the arterial segment 524 includes an arterial lateral opening 544 proximate the distal end thereof. The lateral openings 542, 544 are semi-circular in shape, as best seen in FIGS. 17B and 17C. The lateral openings 542, 544 are in fluid communication with the first and second lumens, respectively, of the catheter body 11 and are sized and configured so as to assist in fanning out fluid exiting therefrom. The nose portion 530 of the present embodiment has a rounded shape, in contrast to the tapered nose portion 30 of FIG. 1, though it is appreciated that various nose portion shape configurations are possible. Also, it is appreciated that the lateral openings can each define one of a variety of configurations.

Figure 18A:
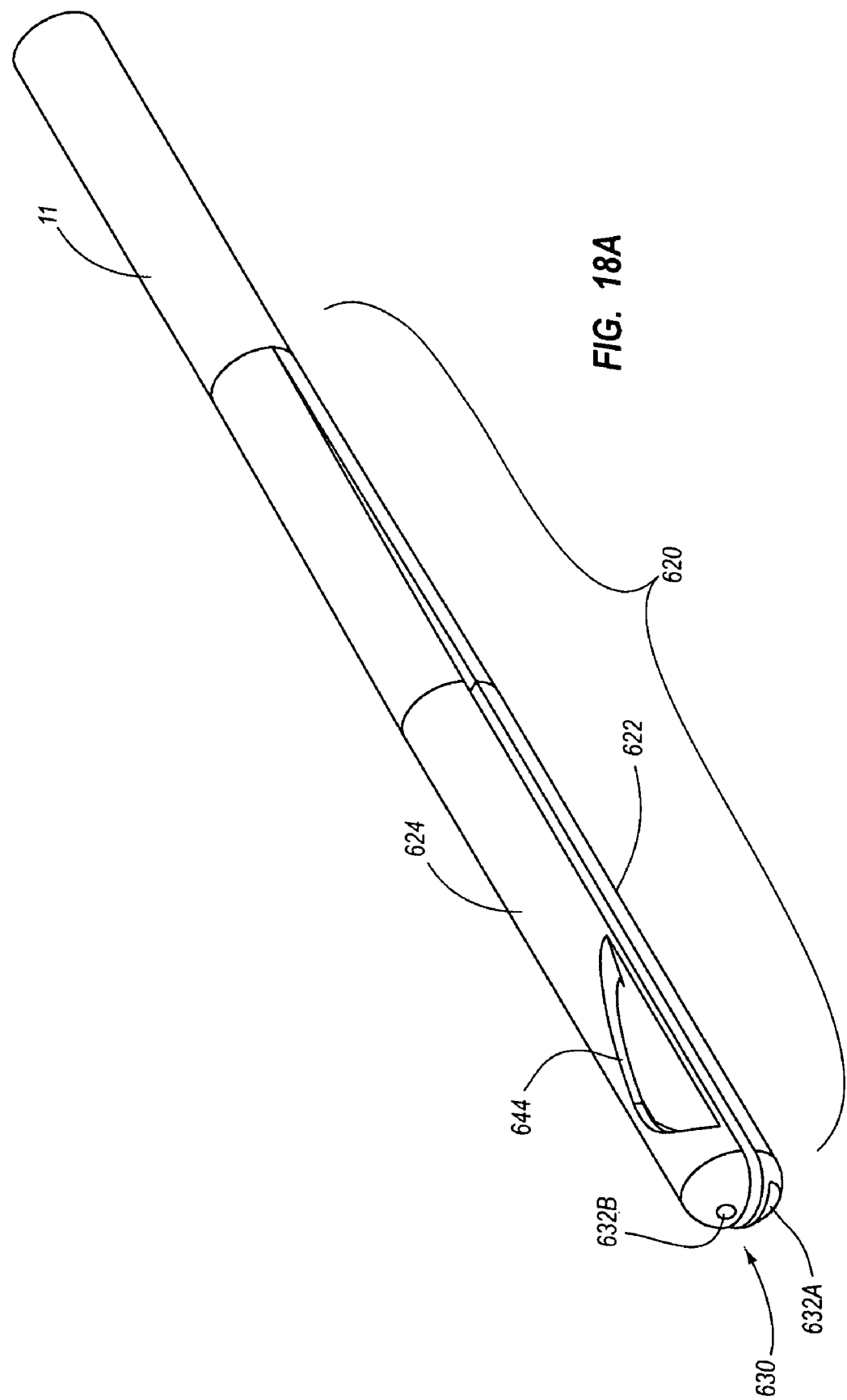
Figure 18D:
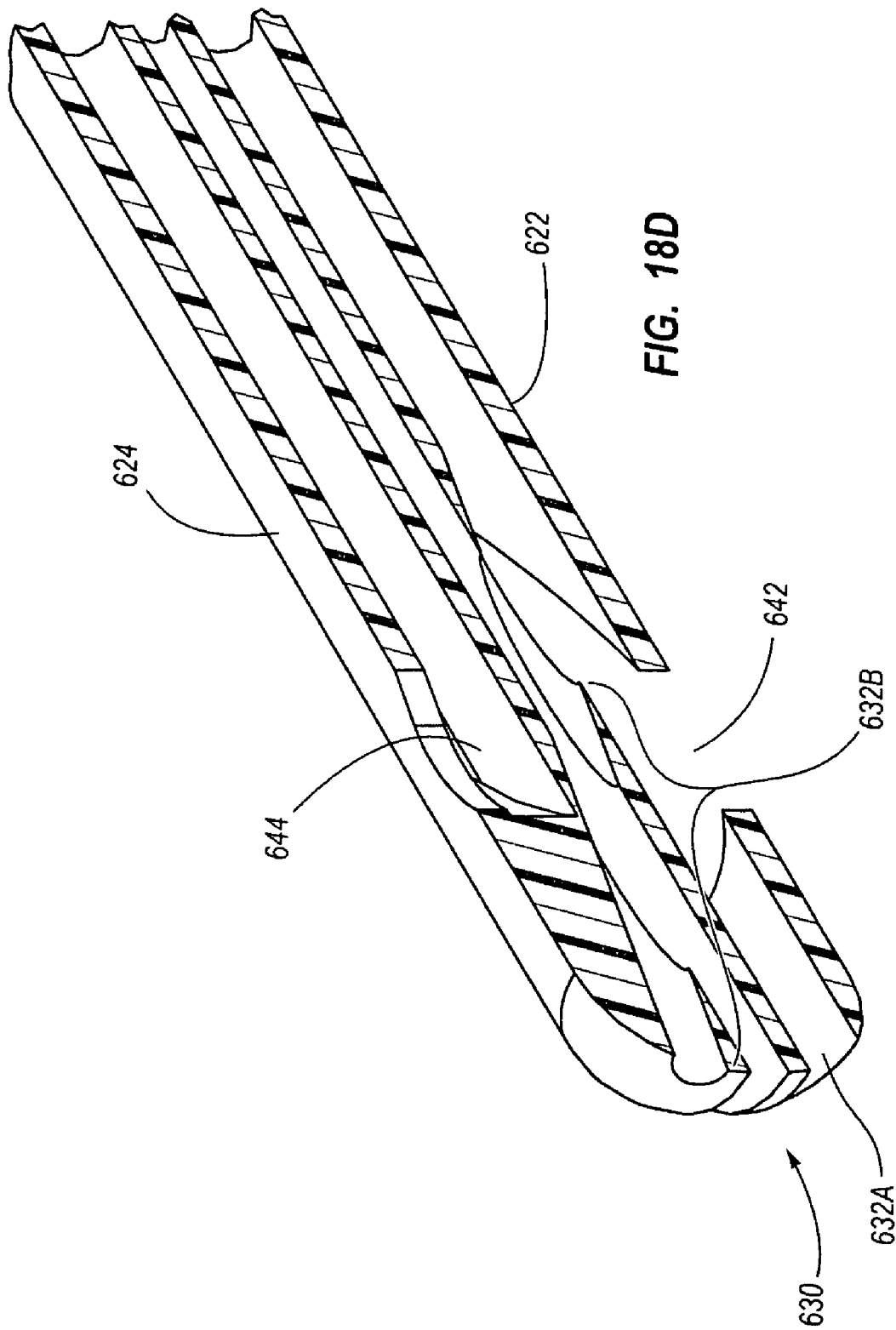

FIGS. 18A-18D depict a distal tip region 620 of a split-tip catheter assembly including a venous segment 622 and an arterial segment 624 that together define a nose portion 630. The venous segment 622 includes a venous distal opening 632A in fluid communication with a first lumen of the catheter body 11. The arterial segment 624 includes a distal opening as part of a guidewire channel 632B. As best seen in FIG. 18D, the guidewire channel 632B is in fluid communication with a second lumen of the catheter body 11, but is angled so as to also communicate with the first lumen defined by the venous segment 622. Thus, the guidewire channel is defined by both the arterial segment 624 and venous segment 622. So configured, a guidewire extending distally from a proximal portion of the first lumen and passing through the portion of the first lumen defined by the venous segment 622, then through the guidewire channel 632B to exit its corresponding opening on the distal end of the arterial segment 624 enables the venous and arterial segments to be maintained in a joined configuration during catheter insertion.

The venous segment 622 includes a venous lateral opening 642 proximate the nose portion 630, while the arterial segment 624 includes an arterial lateral opening 644 proximate the distal end thereof. The lateral openings 642, 644 define a triangular shape and are in fluid communication with the first and second lumens, respectively, of the catheter body 11. The nose portion 630 of the present embodiment has a rounded shape, in contrast to the tapered nose portion 30 of FIG. 1, though it is appreciated that various nose portion shape configurations are possible. Also, it is appreciated that the lateral openings can each define one of a variety of configurations.

Figure 19B:
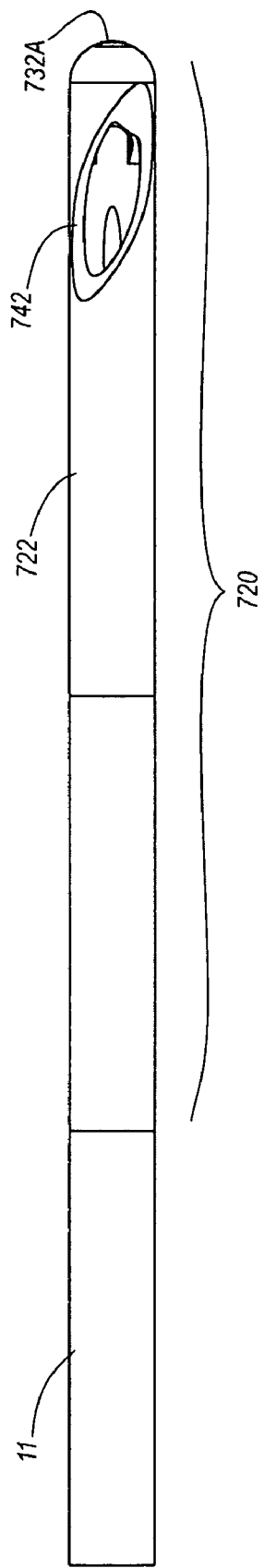
Figure 19C:
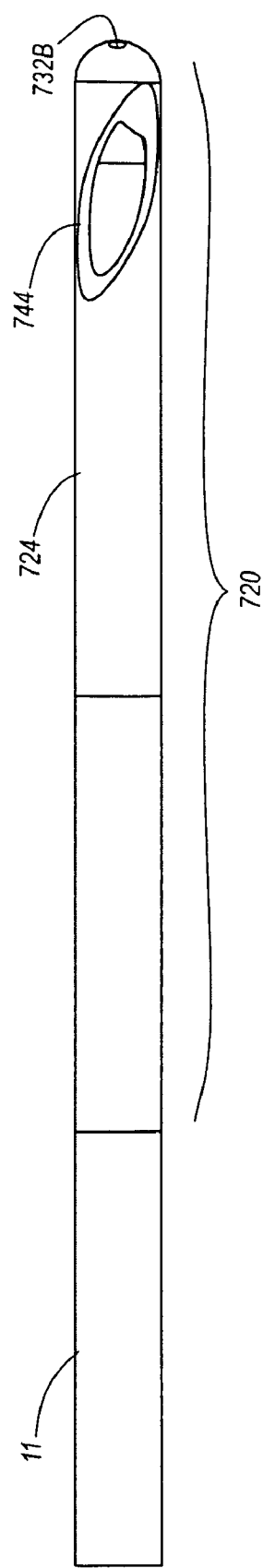
Figure 19D:
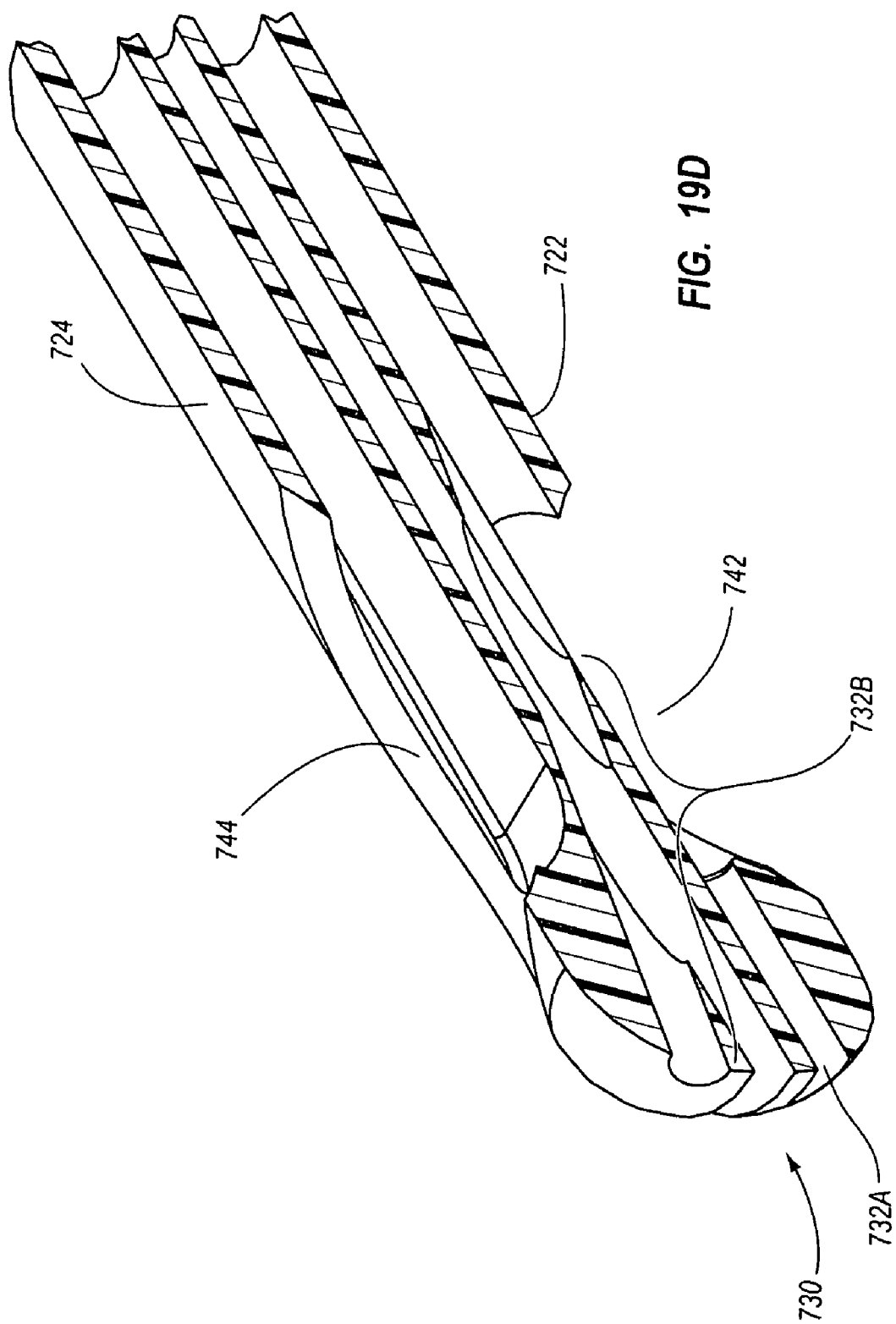

FIGS. 19A-19D depict a distal tip region 720 of a split-tip catheter assembly including a venous segment 722 and an arterial segment 724 that together define a nose portion 730. The venous segment 722 includes a venous distal opening 732A in fluid communication with a first lumen of the catheter body 11. The arterial segment 724 includes a distal opening as part of a guidewire channel 732B. As best seen in FIG. 19D, the guidewire channel 732B is in fluid communication with a second lumen of the catheter body 11, but is angled so as to also communicate with the first lumen defined by the venous segment 722. Thus, the guidewire channel is defined by both the arterial segment 724 and venous segment 722. So configured, a guidewire extending distally from a proximal portion of the first lumen and passing through the portion of the first lumen defined by the venous segment 722, then through the guidewire channel 732B to exit its corresponding opening on the distal end of the arterial segment 724 enables the venous and arterial segments to be maintained in a joined configuration during catheter insertion.

The venous segment 722 includes a venous lateral opening 742 proximate the nose portion 730, while the arterial segment 724 includes an arterial lateral opening 744 proximate the distal end thereof. The lateral openings 742, 744 define a triangular shape and are in fluid communication with the first and second lumens, respectively, of the catheter body 11. The nose portion 730 of the present embodiment has a rounded shape, in contrast to the tapered nose portion 30 of FIG. 1, though it is appreciated that various nose portion shape configurations are possible. Also, it is appreciated that the lateral openings can each define one of a variety of configurations.

FIGS. 20A-20C depict a distal tip region 820 of a split-tip catheter assembly including a venous segment 822 and an arterial segment 824. The venous segment 822 includes a venous opening 848 in fluid communication with a first lumen of the catheter body 11. Similarly, the arterial segment 824 includes an arterial opening 846 in fluid communication with a second lumen of the catheter body 11. The openings 846, 848 are disposed at i.e., coincident with, distal ends of the respective venous and arterial segments 822, 824 and extend proximally therefrom in an angled direction so as to define a triangular opening. Moreover, the venous opening 848 is oppositely disposed as a mirror image of the arterial opening 846 such that each can direct fluid away from the other opening during fluid infusion into the vessel, thus decreasing recirculation and increasing catheter efficiency. Moreover, the openings 846, 848 are sized so as to assist in fanning out fluid exiting therefrom. In addition, the split tip configuration of the distal tip region 820 further separates the venous opening 848 from the arterial opening 846, further improving catheter efficiency. Of course, it is appreciated that the venous and arterial openings of the present embodiment can each define one of a variety of configurations.

Guidewire holes 850 are included on an inward-pointing distal surface of both the venous segment 822 and arterial segment 824 so as to enable the guidewire 46 to be passed therethrough to maintain the two segments in a joined, or contact, configuration during catheter insertion procedures.

Figure 21A:
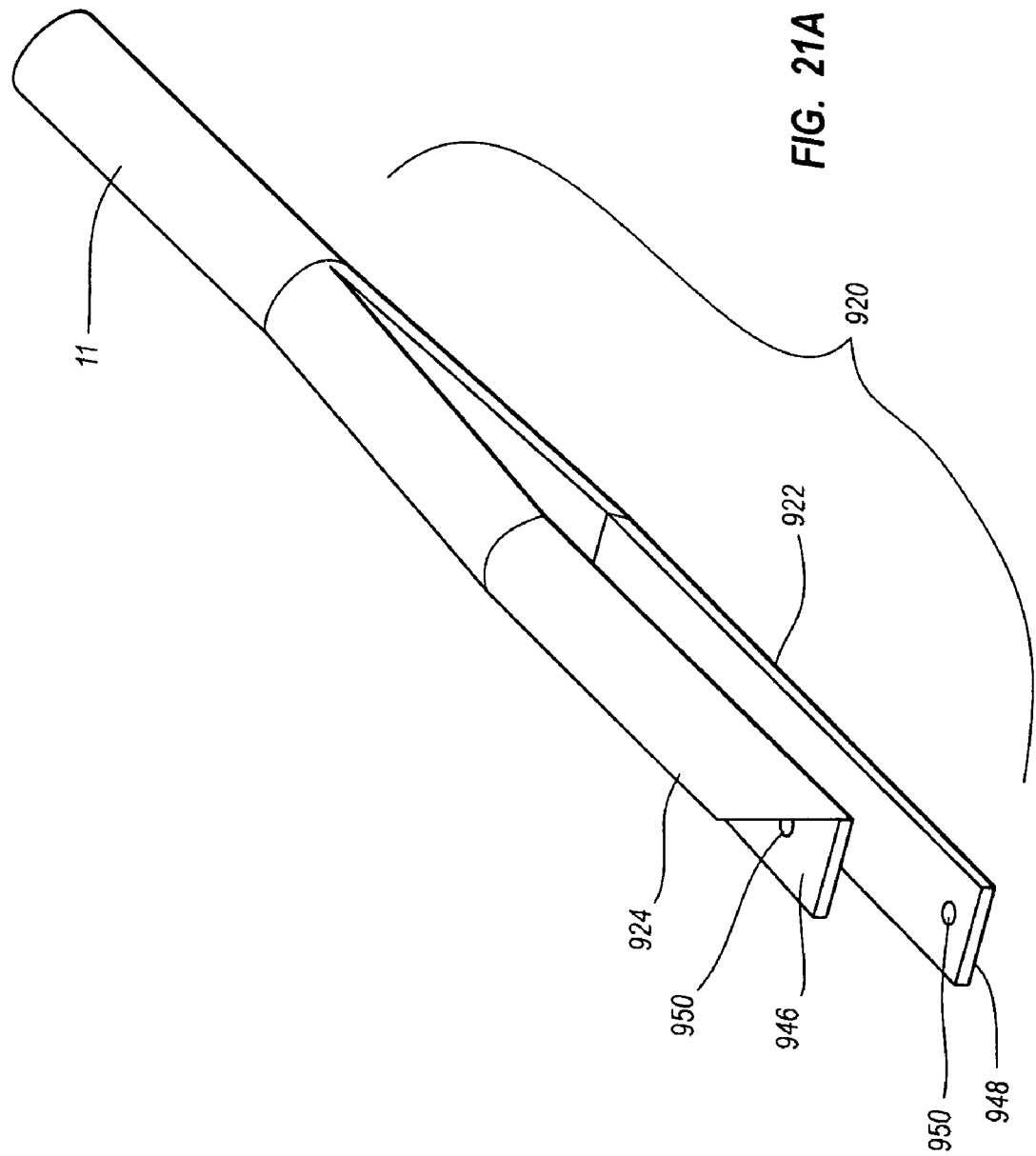
FIGS. 21A-21C are perspective, bottom, and top views, respectively, of a split-tip catheter including a distal region configured in accordance with one embodiment of the present invention.
Figure 21B:
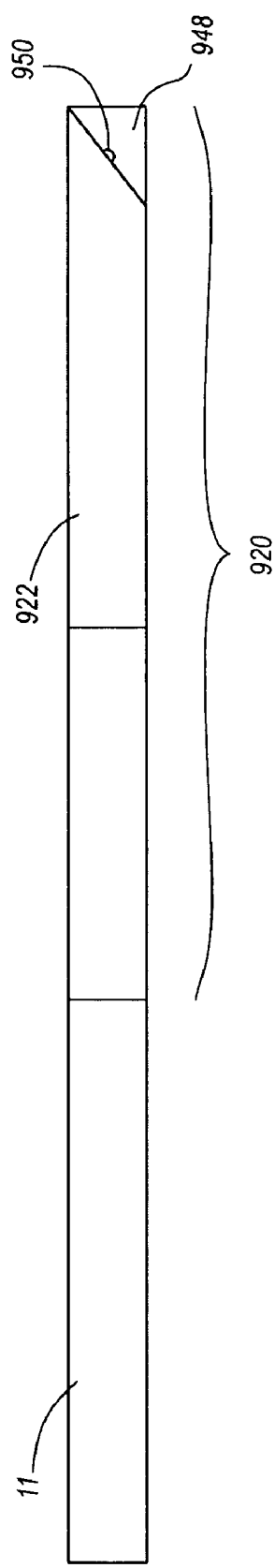
Figure 21C:
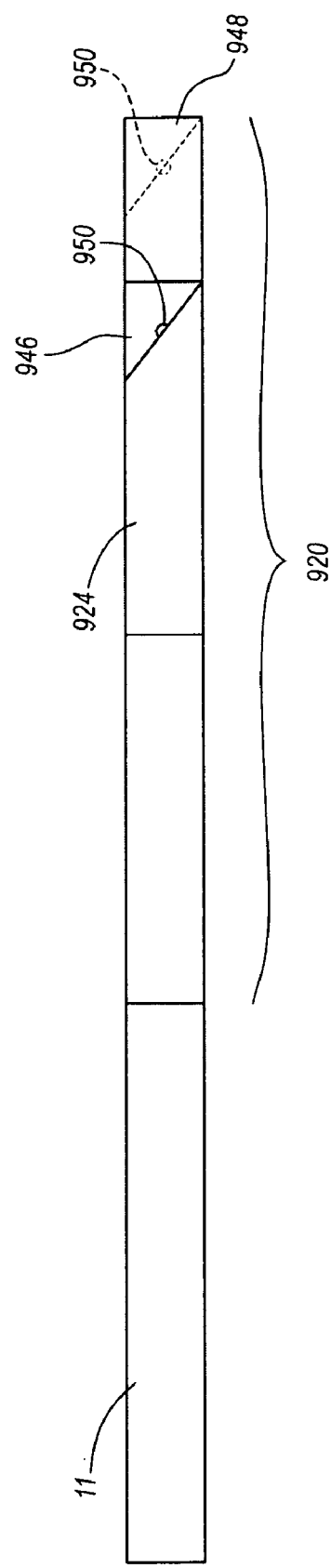

FIGS. 21A-21C depict a distal tip region 920 of a split-tip catheter assembly comprising many elements similar to the embodiment discussed above in connection with FIGS. 20A-20C, including a venous segment 922 defining a venous opening 948, an arterial segment 924 defining an arterial opening 946, and guidewire holes 950. In contrast to the previous embodiment, however, the arterial segment 924 is shortened so as to be staggered proximally with respect to the venous segment 922 to provide further opening separation.

Figure 22A:
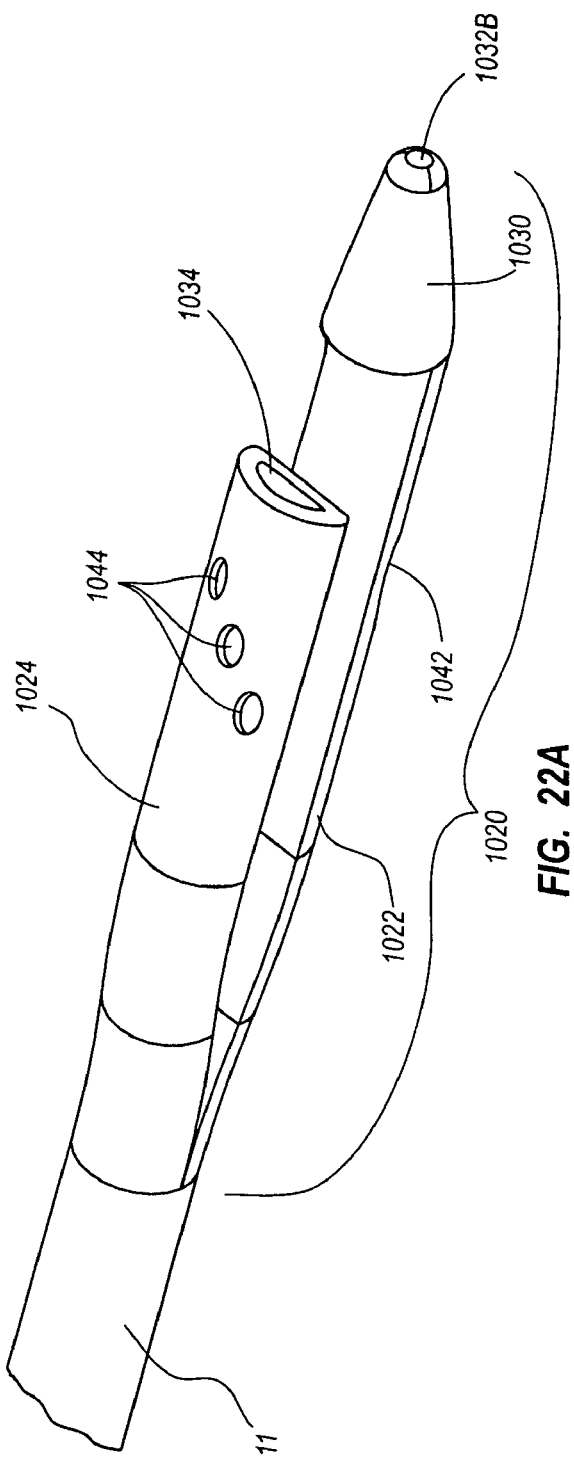
Figure 22B:
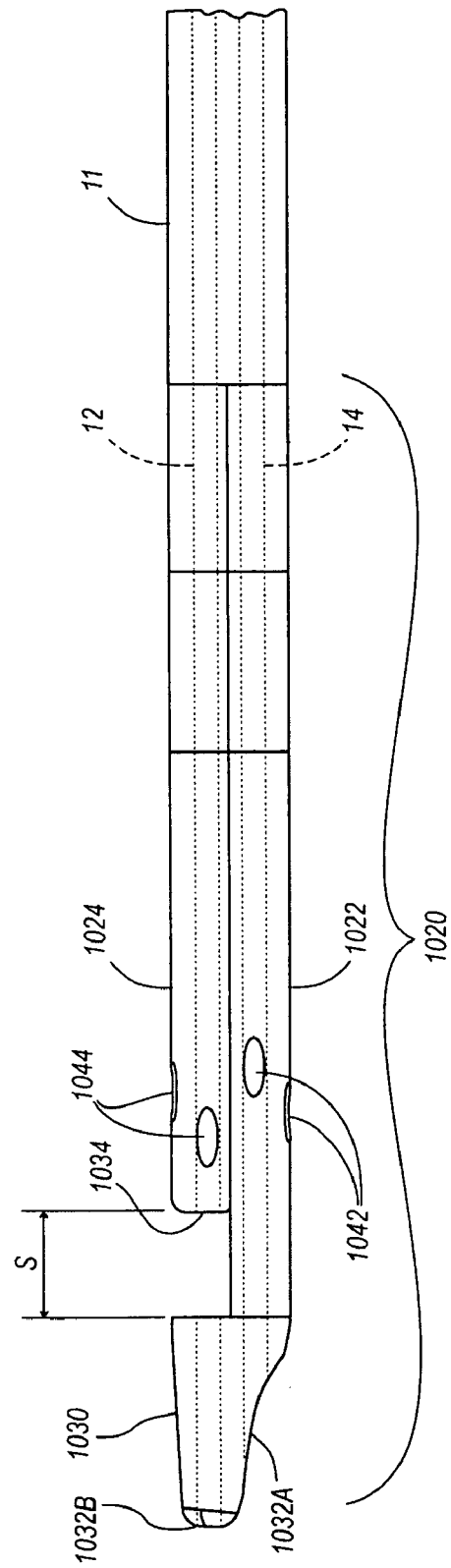

FIGS. 22A-22B depict a distal tip region 1020 of a split-tip catheter assembly according to one embodiment, including a venous segment 1022 and an arterial segment 1024 that selectively seats, or nests, in a recess defined by the venous segment. A nose portion 1030 of the venous segment 1022 includes a venous distal opening 1032A in fluid communication with a first lumen 12 of the catheter body 11 and a guidewire channel 1032B. The arterial segment 1024 includes an arterial distal opening 1034 in fluid communication with a second lumen 14 of the catheter body 11. As shown, a spacing S exists between a proximal end of the nose portion 1030A and a distal end of the arterial segment 1024 whereon is defined the arterial distal opening 1034. Thus, though seated in the recess of the venous segment 1022, the arterial segment 1024 does not occupy the entirety of the recess. A guidewire can span the spacing S between the nose portion 1030 and the arterial distal opening 1034 to maintain the arterial segment 1024 seated in the recess of the venous segment 1022.

The venous segment 1022 includes a plurality of venous lateral openings 1042 proximal to the nose portion 1030, while the arterial segment 1024 also includes a plurality of arterial lateral openings 1044 proximal to the distal end thereof. The lateral openings 1042 and 1044 are in fluid communication with the first and second lumens 12, 14, respectively, of the catheter body 11 and are spaced apart to preclude or lessen vessel wall suck-up.

Figure 23C:
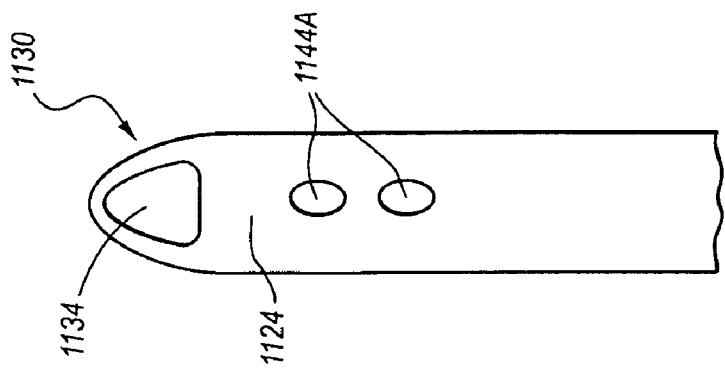
Figure 23B:
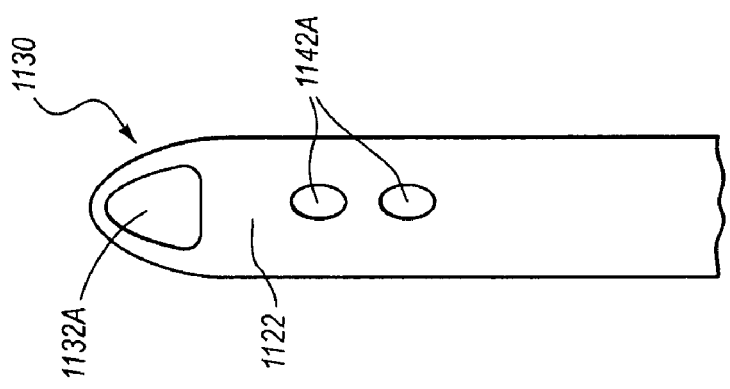
Figure 23A:
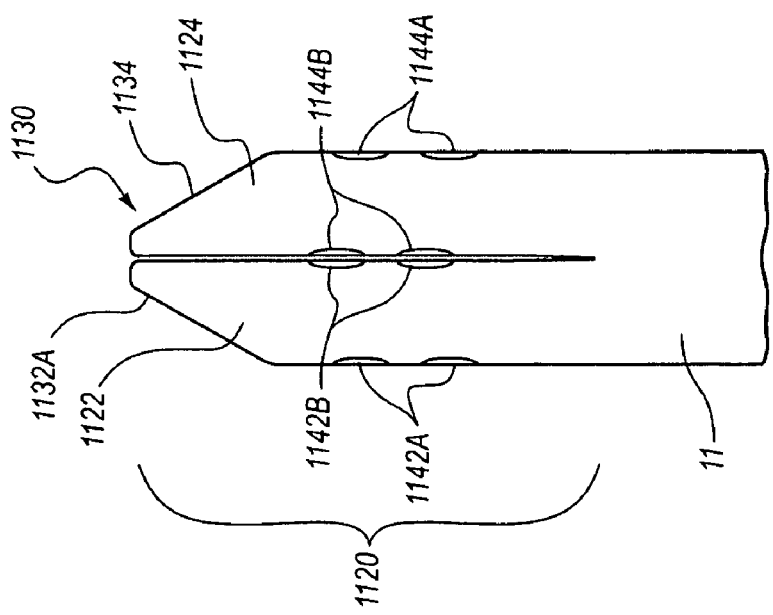

FIGS. 23A-23C depict a distal tip region 1120 of a split-tip catheter assembly including a venous segment 1122 and an arterial segment 1124 that together define a nose portion 1130. The venous segment 1122 includes a venous distal opening 1132A in fluid communication with a first lumen of the catheter body 11. The arterial segment 1124 includes an arterial distal opening 1134 in fluid communication with a second lumen of the catheter body 11. The distal ends of the venous and arterial segments 1122, 1124 are angled so as to define the nose portion 1130 with a tapered shape.

The venous segment 1122 includes a plurality of venous outer lateral openings 1142A and venous inner lateral openings 1142B proximal to the nose portion 1130. Likewise, the arterial segment 1124 includes a plurality of arterial outer lateral openings 1144A and arterial inner lateral openings 1144B proximal to the nose portion 1130. The lateral openings 1142A, B and 1144A, B are in fluid communication with the first and second lumens, respectively, of the catheter body 11 and are spaced apart to preclude or lessen vessel wall suck-up.

The distal ends of the venous segment 1122 and arterial segment 1124 are un-staggered with respect to one another so as to enable both lateral opening sets 1142A, B and 1144A, B to be placed in a single desired location within the patient's vasculature, such as in the SVC for instance. The venous segment 1122 and arterial segment 1124 can be maintained in a contact configuration via the use of a guidewire that extends through the inner lateral openings 1142B, 1144B, for instance.

FIGS. 24A-30 describe distal tip regions of the catheter body 11 configured according to other example embodiments. It should be appreciated that the distal tip regions to be described below can be included with hemodialysis catheters or with other catheters, such as central venous catheters, for example.

Reference is now made to FIGS. 24A-24F, which depict various details regarding a distal tip region, generally designated at 1220, according to one embodiment. The distal tip region 1220 generally includes the distal portion of the catheter assembly 10, including terminal distal portions of the first lumen 12 and second lumen 14. In the discussion below, it is understood that in one embodiment the first lumen 12 is considered a venous lumen for returning treated blood to the vessel and the second lumen 14 is considered the arterial lumen for uptake of blood from the vessel. As already mentioned, however, these duties of the first and second lumens may be reversed. Thus, these designations are merely used herein for purposes of convenience.

The distal portion 1220 includes a nose portion 1230 at the distal end thereof. In the present embodiment, the nose portion 1230 generally defines a tapered, generally conical shape, though it is appreciated that the nose portion may define other circumferentially convergent shapes, including hemispherical or bullet-shapes, frustoconical, and other smooth and/or contoured shapes that converge toward the distal end. The nose portion 1230 is therefore atraumatic, reducing insertion forces during placement and minimizing abrasion between the nose portion surface and the walls of the vessel in which the distal region of the catheter is disposed, thus reducing vascular injury. In contrast to previous embodiments, the distal portion 1220 does not include separate split tip portions, but is a unitary, or solid-body, structure, defining distal portions of the first and second lumens 12, 14 (FIGS. 25A, 25B).

The catheter body 11 defines a venous distal opening 1232A on the tapered surface of the nose portion 1230 so as to be in fluid communication with the distal portion of the first lumen 12. The catheter body 11 further defines an arterial distal opening 1232B at the distal end of the nose portion 1230 so as to be in fluid communication with the second lumen 14. The openings of both the venous and arterial distal openings 1232A, 1232B face in the distal direction for fluid flow purposes as will be described. The second lumen 14 and corresponding arterial distal opening 1232B in the current embodiment can receive a guidewire therethrough for enabling over-the-wire placement of the catheter 10. The first lumen 12 and corresponding venous distal opening 1232A can also be used for receiving a guidewire therethrough, if desired. Of course, the venous and arterial distal opening, as well as the other catheter openings to be described below, can vary in size and placement from what is explicitly described herein.

FIGS. 24A-24F further depict the distal portion 1220 as including along its length a venous lateral opening 1242 and an arterial lateral opening 1244 defined by the catheter body 11 proximate the nose portion 1230. The lateral openings 1242 and 1244 can take various shapes and configurations, but in the present embodiment the lateral openings are defined by compound-angle cross-drilled cuts through the outer surface of the catheter body 11 to establish fluid communication with the respective first or second lumens 12, 14. In one embodiment, such cuts are referred to as "skive" cuts.

Figure 24B:
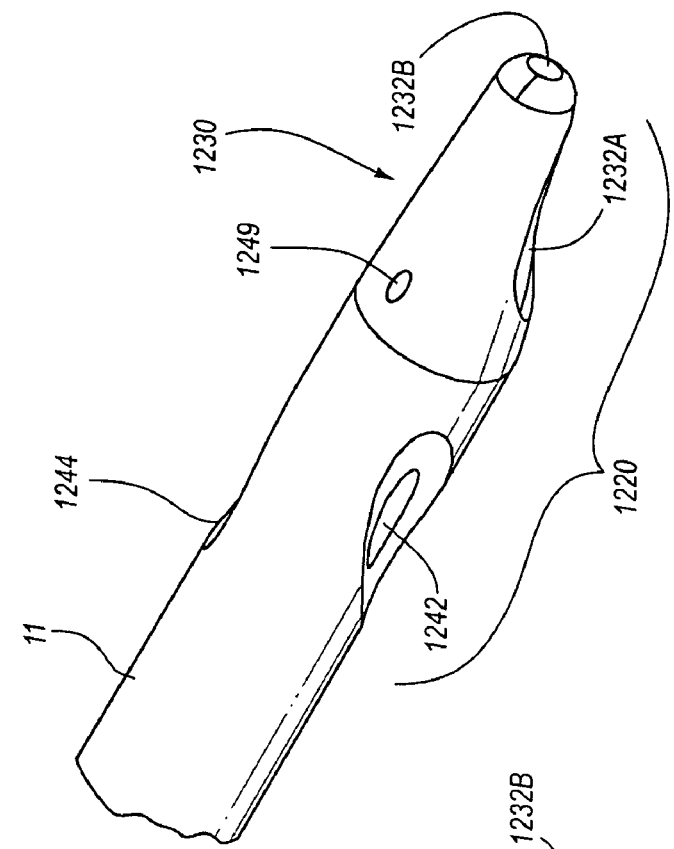
FIGS. 24A-24F are various views of the distal region of a catheter in accordance with one example embodiment.
Figure 24A:
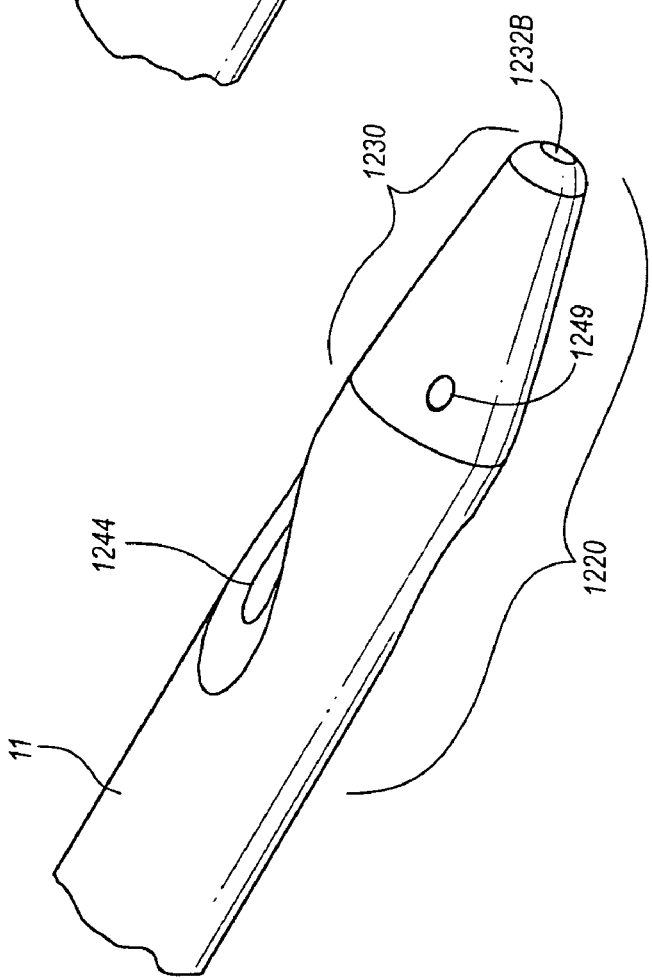
Figure 24C:
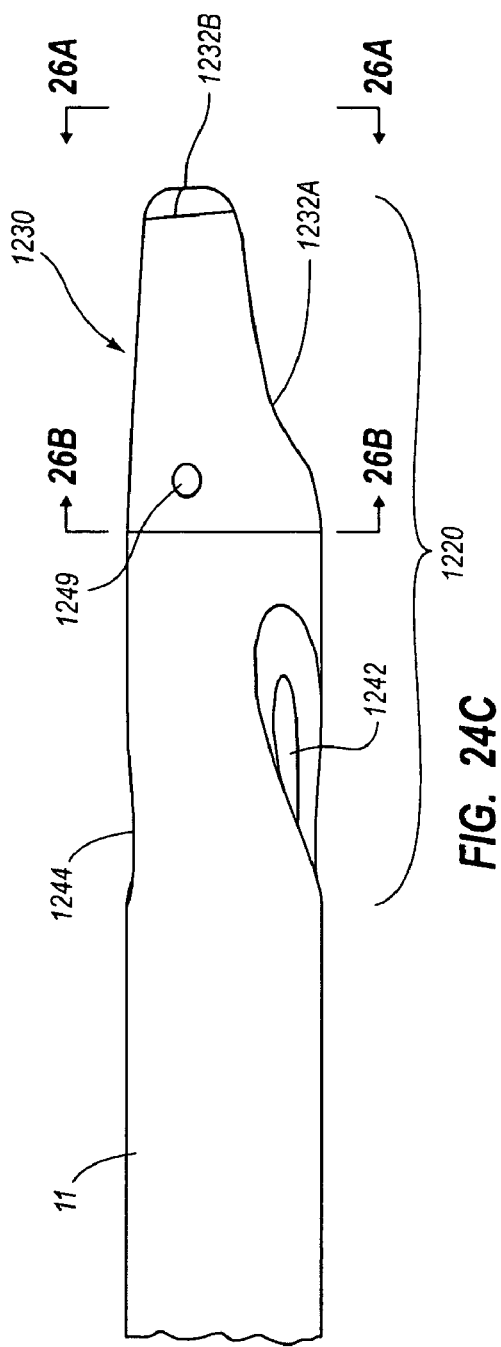
Figure 24D:
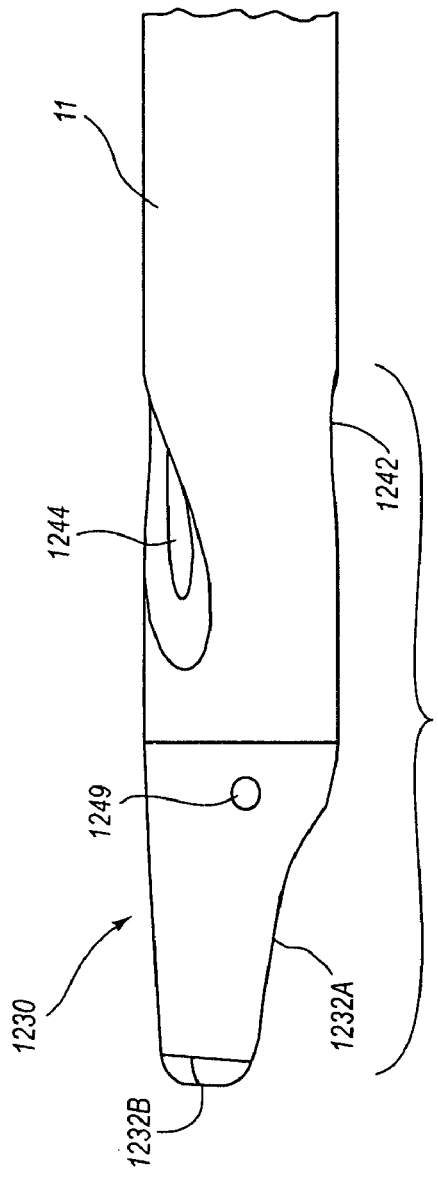
Figure 24E:
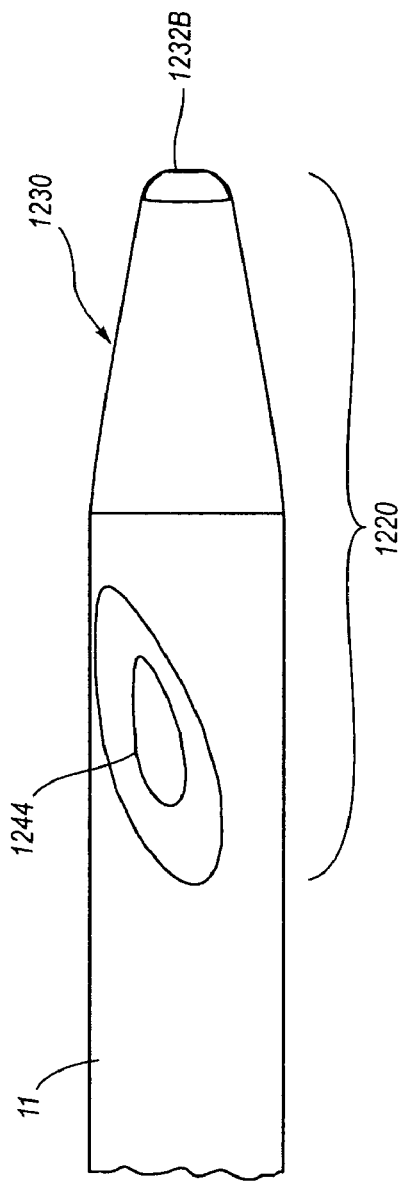
Figure 24F:
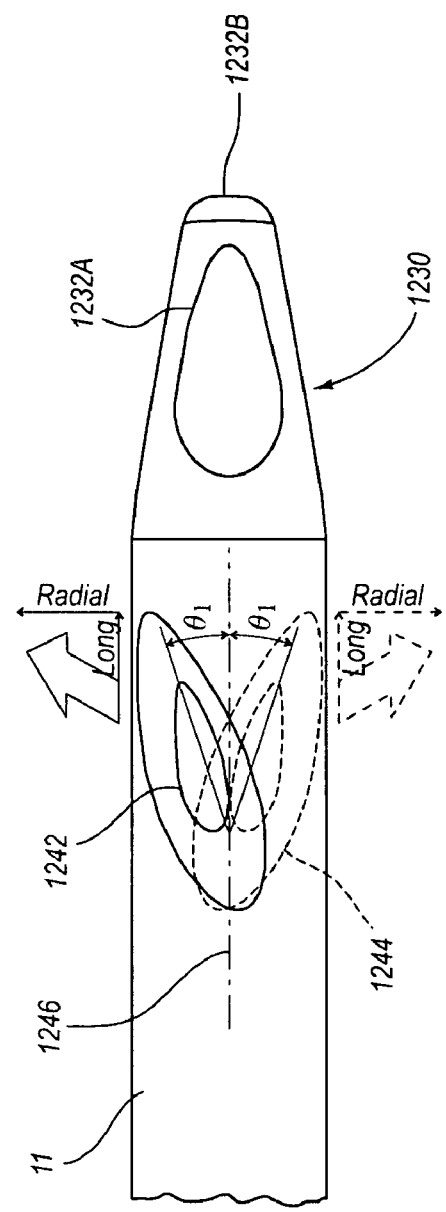

In one embodiment and as best seen in FIG. 24F, the longitudinal axis of each cross cut of the lateral openings 1242, 1244 defines an angle $\theta_1$ of about 35 degrees with a longitudinal axis 1246 of the catheter body 11 in the perspective shown in FIG. 24F, though this angle can vary in one embodiment from about 20 to about 90 degrees. In another embodiment, for example the angle $\theta_1$ can be defined at 30 degrees. The longitudinal axis of each cross cut of the lateral openings 1242, 1244 further defines an angle $\theta_2$ in one embodiment of about 15 degrees with the longitudinal axis 1246 in the perspective shown in FIG. 25A. In the perspective shown in FIG. 25A, the angle $\theta_2$ can also be defined with respect to a plane coincident with the longitudinal axis 1246 that bisects the first lumen 12 and second lumen 14, i.e., coplanar with the septum separating the first and second lumens, though this angle can vary in one embodiment from about 0 to about 45 degrees. In another embodiment, for example, angle $\theta_2$ is defined at 25 degrees.

This angular character imparts both a lateral, or radial, directional component, as well as a longitudinal directional component to fluid flow out of either lateral opening 1242, 1244, as represented by the flow arrows in FIG. 24F. So configured, the lateral openings 1242, 1244 make it such that fluid exiting the catheter from the venous lateral opening 1242 is imparted a flow direction that is substantially opposite in a radial direction and substantially similar in a longitudinal direction to fluid that would exit the catheter from the arterial lateral opening 1244. This aspect assists in reducing blood recirculation via the catheter 10.

Note that, in one embodiment, the angle defined by each lateral opening can be different. In another embodiment, noncompound-angle cross cuts may be used to define the lateral openings. It should be appreciated that the particular angular configuration of the lateral openings can vary from what is described herein while still residing within the scope of embodiments of the present invention.

In the present embodiment, the cross cut that defines the lateral openings 1242, 1244 is achieved via use of a cylindrical drill bit or coring tool having a size sufficient to define the lateral opening having the compound angle described above. For instance, in one embodiment a drill bit is used to diagonally cross cut the venous and arterial lateral openings 1242, 1244 through the catheter body. Note that the catheter body size in one embodiment can vary from 7-16 Fr., though other French sizes are also possible. Note here that, though identically sized and shaped in the present embodiment, the first and second openings could include respectively differing dimensions if desired or needed for a particular application. Of course, other methods for defining the lateral openings, including molding, cutting, heat forming, etc., may also be used.

As a result of defining the cross cuts as just described, the elongate venous and arterial openings 1242, 1244 are defined by perimeters shaped in the present embodiment as a figure-eight shape, or analemma, when viewed in a two-dimensional perspective and an elongate saddle shape when viewed in a three-dimensional perspective. "Elongate" and "elongated" are understood herein as including a long or extended shape, or including more length than width. Again, this enables the lateral openings 1242, 1244 to partially extend longitudinally and circumferentially about the outer perimeter of the catheter body 11. This helps to prevent undesired suctioning of the distal tip region 1220 to the vessel wall when one of the openings is removing blood from the vessel as the negative flow pressure of the opening is distributed about a portion of the catheter body circumference. If vessel suck-up does occur, the lateral openings 1242, 1244 are shaped so as to nonetheless provide acceptable fluid flow in and out of the catheter assembly 10. The relatively large size of the lateral openings 1242, 1244 also assists in the prevention of occlusion or sheath formation and provides a fanned-out or wide distribution of fluid flowing out therefrom. Recirculation efficiency rates are improved as a result.

In addition, the longitudinal axes of the lateral openings 1242, 1244 are symmetrically opposed in direction from one another, as best shown in FIG. 24D, to produce a "criss-cross" relationship between the lateral openings. This ensures that fluid entry and exit from the lateral openings occurs on opposite sides of the catheter body 11, thus further reducing recirculation of already treated blood. Furthermore, this symmetry ensures similar fluid flow characteristics to be realized even when fluid flow through the catheter assembly 10 is reversed.

It is noted that in one embodiment the size of the lateral openings 1242, 1244 is such that each can accommodate the entirety of fluid flow through their respective first or second lumens 12, 14. Thus, the inclusion of the lateral openings 1242, 1244 with their corresponding distal openings 1232A, 1232B provides a redundant system such that any clotting that occurs at one opening will not significantly impact fluid throughput of the respective lumen. In addition, the lateral opening configuration described herein minimizes radical redirection of the fluid upon exiting the catheter body 11 via either of the lateral openings 1242 and 1244, which in turn prevents fluid turbulence and possible clotting or hemolysis.

FIGS. 24A-24F show that in the present embodiment the venous and arterial lateral openings 1242 and 1244 are substantially un-staggered, i.e., equally placed with respect to one another along the longitudinal length of the catheter body 11 such that each is substantially disposed an equal distance from the distal catheter end 11B. Such un-staggered disposal of the lateral openings 1242 and 1244 enables both openings to be placed proximate a desired anatomical location within the vasculature and ensures that the recirculation rate of already treated blood through the catheter assembly 10 is held relatively constant regardless the respective directions of blood travel in/out of the lateral openings. This feature is useful should reversal of blood flow directions through the catheter be necessary. In one embodiment, the recirculation rate in either direction is less than or equal to about five percent. In another embodiment, the position of the venous and lateral openings can be staggered.

It should be appreciated that the labels "venous" and "arterial" as used above in describing the various components of the present catheter are employed for sake of convenience in describing aspects of embodiments of the present invention. Indeed, though the second (arterial) lumen 14 is normally employed in hemodialysis procedures for aspirating blood from the blood vessel in which the catheter is disposed and the first (venous) segment 12 for returning already treated blood to the vessel, this can be reversed such that blood is returned via the arterial segment and aspirated by the venous segment. As such, the present invention should not be considered limited by the use of this and other descriptive terminology herein.

In one embodiment, the nose portion 1230 is defined via a radiofrequency ("RF") tipping process, but other forming processes may also be employed to define the distal tip region in accordance with other embodiments and as appreciated by one skilled in the art.

Reference is now made to FIGS. 25A and 25B in describing flow characteristics with respect to the configuration of the distal tip region 1220 of the present catheter assembly 10. FIGS. 25A and 25B show the distal tip region 1220 as in position after the catheter assembly 10 has properly positioned within a vessel of a patient. Arrow 1248 shows the direction of blood flow past the distal tip region 1220 within the patient's vessel.

In greater detail, FIG. 25A shows fluid flow through the distal tip region 1220 in a "forward" direction, or first staggered flow configuration, wherein blood is aspirated by the second lumen 14, or "uptake" lumen, for removal from the body and treatment by a hemodialysis apparatus or for some other suitable purpose. Aspirated blood enters the second lumen 14 via both the arterial distal end opening 1232B and the arterial lateral opening 1244. However, because the second lumen 14 is under negative pressure during aspiration, the majority of blood aspirated by the second lumen is removed via the arterial lateral opening 1244 due to its relatively more proximal position with respect to the pressure differential in the proximate vessel region.

Simultaneously, blood is infused, or returned, to the vessel by the first lumen 12, or "return" lumen, after treatment by a hemodialysis apparatus or some other suitable purpose. Infused blood exits the first lumen 12 from both the venous distal opening 1232A and the venous lateral opening 1242. However, because the second lumen 12 is under positive pressure during infusion, the majority of blood returned to the bloodstream by the first lumen exits via the venous distal opening 1232A due to its relatively more distal position with respect to the pressure differential in the proximate vessel region. Note that this arrangement produces an effective stagger distance F in the "forward" direction between the primary aspiration site, i.e., the arterial lateral opening 1244, and the primary infusion site, i.e., the venous distal opening 1232A. This effective stagger distance, together with the lateral orientation of the lateral openings 1242, 1244 provides for low recirculation of already-treated blood within the vessel, recirculation being defined as already-treated blood that is returned to the bloodstream via the venous lumen being immediately aspirated by the arterial lumen to be re-treated. Such recirculation is undesirable as it results in lower treatment efficiency and longer treatment time.

During hemodialysis procedures, it is sometimes necessary to reverse the blood flow through the catheter assembly 10. FIG. 25B shows fluid flow through the distal tip region 1220 during such a "reverse" flow situation, or second staggered flow configuration. In contrast to the forward flow conditions of FIG. 25A, the second lumen 14 in FIG. 25B is employed to infuse blood into the vessel, while the first lumen 12 aspirates blood from the vessel. In this configuration, the majority of infused blood enters the vessel via the arterial distal opening 1232B, while the majority of aspirated blood is removed via the venous lateral opening 1242. This arrangement produces an effective stagger distance R in the "reverse" direction between the primary aspiration site, i.e., the venous lateral opening 1242, and the primary infusion site, i.e., the arterial distal opening 34. Thus, it is seen that a desired stagger between the primary infusion and aspiration points is achieved regardless of the direction in which the catheter is operating. In one embodiment, the effective stagger distance F in the forward direction is about 0.04 inch, while the effective stagger distance R in the reverse direction is about 0.6 inch, though the lateral and distal openings can be varied to produce other stagger distances. This can be compared to forward and reverse effective stagger distances of about 0.43 inch and about 0.23 inch, respectively, for the split-tip configuration shown in FIGS. 3A-3D. In one embodiment, both the forward and reverse effective stagger distances for the catheters described herein can be in a range of from about 0.1 inch to about 1 inch, though other distances can also be achieved.

In one embodiment, the catheter body 11 can define one or more arterial side holes 1249 that are in communication with the second lumen 14 to assist in providing desired fluid flow via the second lumen. In the present embodiment, the side holes 1249 each define a diameter of about 0.030 inch, compared with the arterial distal opening 1232B, which defines an opening of about 0.040 inch. Though shown here as round, the side holes can include other shapes and sizes as well. In other embodiments, the first lumen can include additional side holes as well.

Figure 25C:
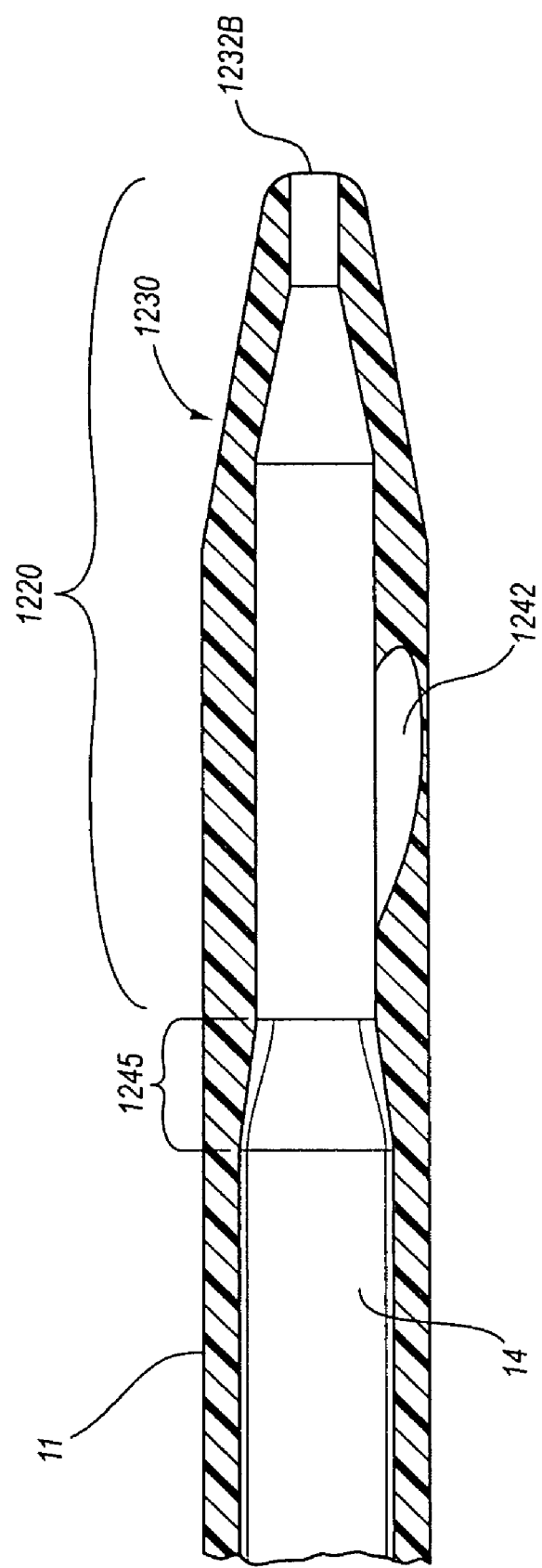
Figure 26B:
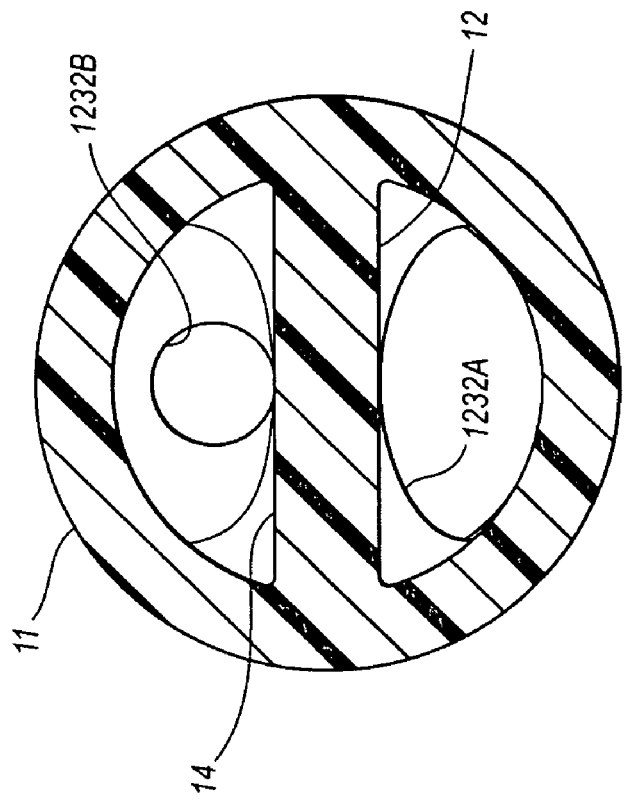
FIG. 26B is a cross sectional view of the catheter of FIG. 24C taken along the line 26B-26B.
Figure 26A:
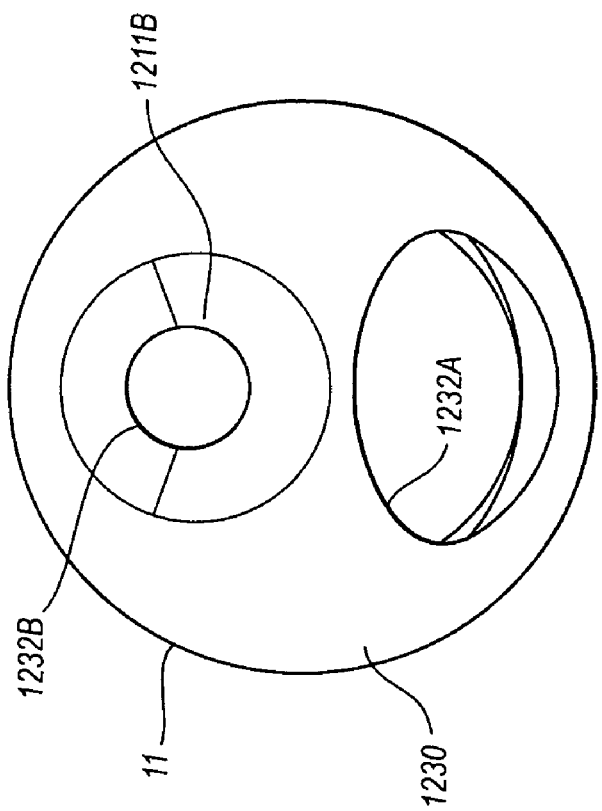
FIG. 26A is a distal end view of the catheter of FIG. 24C taken along the line 26A-26A.

As shown in FIGS. 25A-25C, the first and second lumens 12, 14, each include a transition region 1245 in which region the cross sectional shape of each lumen changes from a "D"-shape to an oval shape in a configuration similar to that described in connection with FIGS. 5C-5G. FIG. 25C depicts further narrowing of the lumen 14 in one embodiment in the nose portion 1230 proximate the arterial distal opening 1232B. It is appreciated that other lumen size configurations can also be used in other embodiments. Indeed, in other embodiments narrowing of the one or both lumens can occur proximal to the distal tip region, or only at the distal end thereof. In still other embodiments, no narrowing of the lumens through the distal tip region occurs. FIG. 26A shows an exterior distal end view of the distal tip portion 1220 of the catheter assembly 10, while FIG. 26B shows a distal facing internal view thereof.

Figure 27:
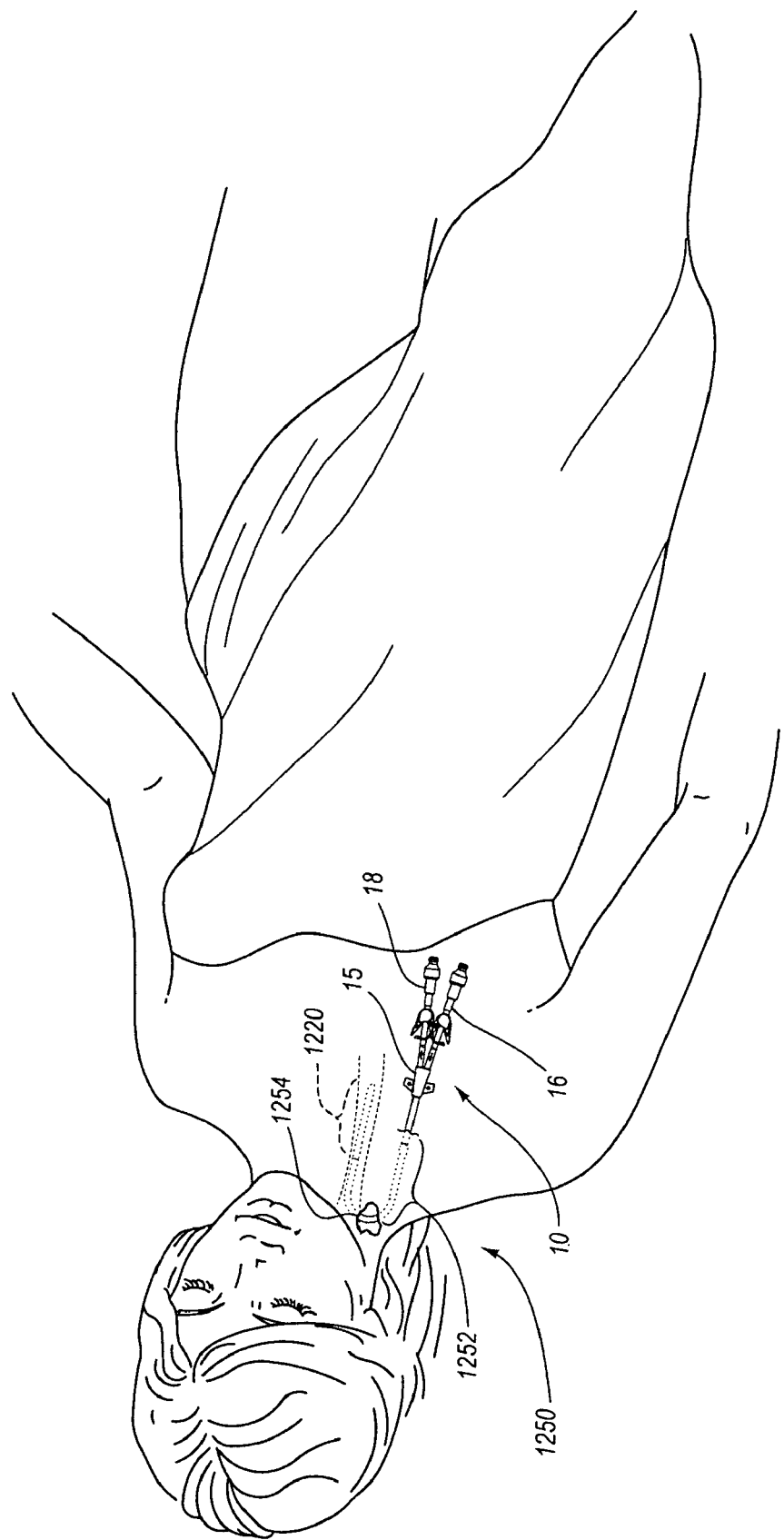
FIG. 27 is a simplified view of the catheter of FIG. 24A after insertion into a vasculature of a patient.

FIG. 27 depicts the catheter assembly 10 after placement in the vasculature of a patient 1250, wherein a tunneled region 1252 intermediate the proximal and distal ends of the catheter body 11 is disposed underneath the skin of the patient. As shown, the proximal portion of the catheter assembly 10, including the hub 15 and extension legs 16 and 18, is exposed proximal the tunneled region 1252. Correspondingly, a distal portion of the catheter assembly 10 is shown distal of the tunneled region 1252 and inserted through an incision site 1254 into the patient's vasculature such that the distal tip region 1220 is positioned in a desired location, such as in a lower region of the superior vena cava ("SVC"). The cuff 19 (FIG. 1) is included in the tunneled region 1252 of the catheter assembly 10 such that tissue in-growth into the cuff may be achieved to subcutaneously anchor the catheter to the patient's body and prevent unintended movement of the catheter. The process by which the tunneling configuration shown in FIG. 27 is achieved is referred to as antegrade tunneling. Note, however, that the catheter 10 can be placed by other insertion and tunneling methods as well.

Figure 28D:
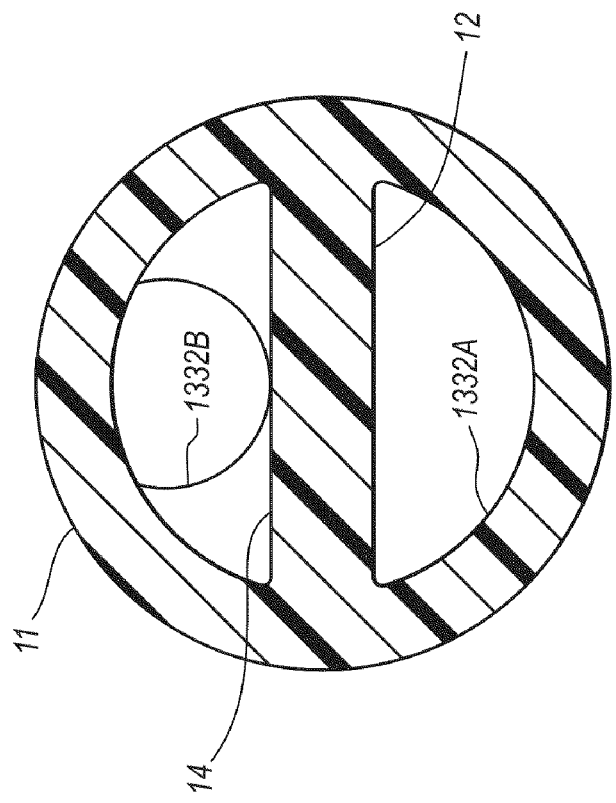
Figure 28C:
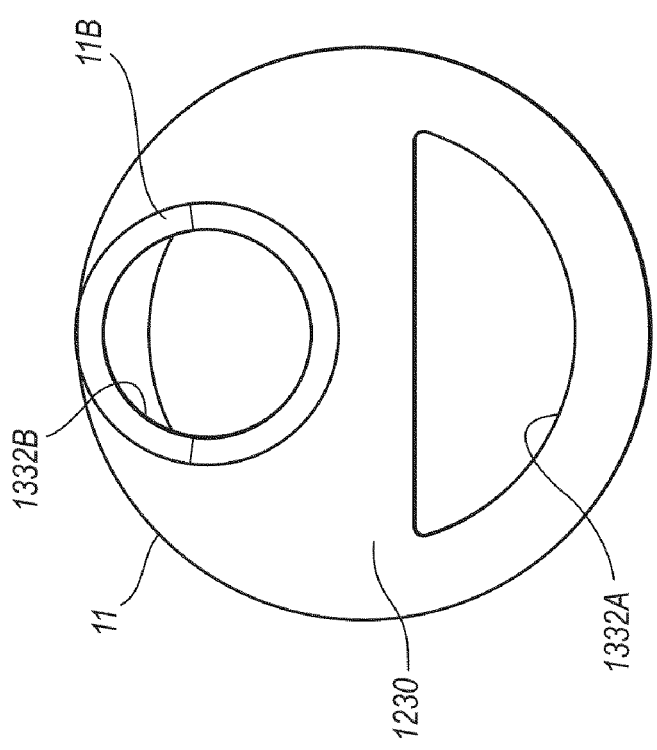

Reference is now made to FIGS. 28A-28D, which depict various aspects of the catheter body 11, according to another example embodiment. Note that, as the present catheter body shares various details with the catheter body described in previous embodiments, only selected differences are discussed here. The catheter body 11 of FIGS. 28A-28D comprises the distal tip region 1220, which in turn includes the venous lateral opening 1242 and the arterial lateral opening 1244, each defined by the catheter body. A venous distal opening 1332A and an arterial distal opening 1332B are also included in the distal tip region 1220, as defined by the catheter body 11. In contrast to earlier embodiments, the venous distal opening 1332A is defined as to be relatively larger than the venous distal opening 1232A of FIG. 26A, while the arterial distal opening 1332B is also defined to be larger relative to the arterial distal opening 1232B shown in FIG. 26A. The relatively larger sizes of the distal openings provide for enhanced fluid flow therethrough. As best seen in FIG. 28B, the distal profile of the distal tip region 1220 is relatively less tapered when compared to the profile of FIG. 25A, though it is appreciated that the profile and relative sizes of the lateral and distal openings of the distal tip region can be modified in various ways, as appreciated by one skilled in the art.

FIGS. 29A and 29B depict yet another example embodiment of the catheter body 11, wherein the distal tip portion 1220 comprises a plurality of distal end openings defined by the catheter body, including a venous distal opening 1432A and symmetrically opposed arterial distal opening 1432B. The openings 1432A and 1432B are each defined as circular segment openings so as to promote lateral and distal distribution of fluid flowing out therefrom. Their symmetrical opposition as best seen in FIG. 29A reduces the likelihood of blood recirculation. The nose of the catheter body is tapered in the illustrated embodiment, though other tip shapes are also possible.

A guidewire hole 1432C is also defined at the distal end of the catheter body 11, and is in communication with one of the catheter body lumens, such as the first lumen 12. This enables a guidewire to pass through the first lumen 12 and out the guidewire hole 1432C to enable the catheter to be placed by over-the-guidewire techniques.

Figure 30:
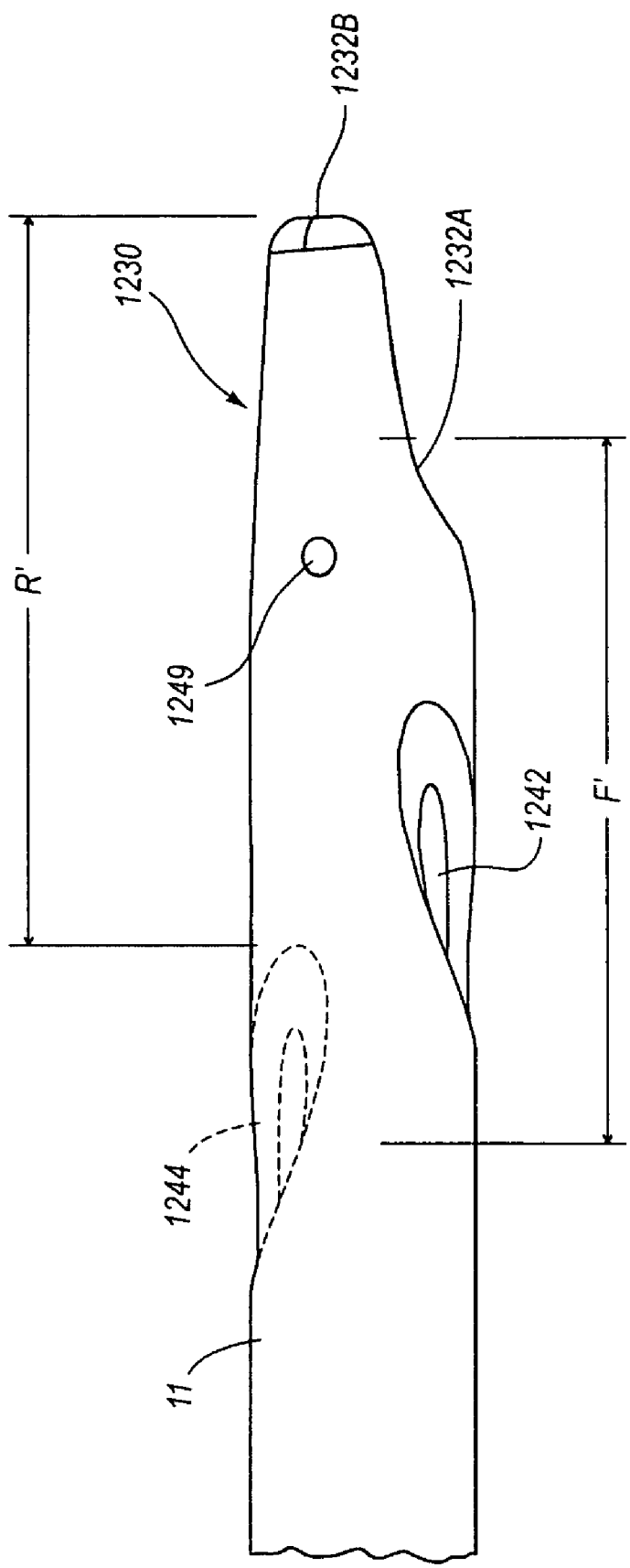
FIG. 30 is a side view of a distal region of a catheter body including staggered lateral openings in accordance with one example embodiment.

FIG. 30 depicts the catheter body 11 one possible embodiment, wherein the lateral openings 1242, 1244 are longitudinally staggered with respect to one another so as to provide substantially equal effective stagger distances in both the forward (F') and reverse (R') directions, during hemodialysis procedures as described above in connection with FIGS. 25A, 25B. As such, it should be appreciated that relative positioning of the lateral and distal openings may vary from what is described herein while still residing within the scope of the present claims, and that such variation in the lateral and distal openings can be applied to the split-tip as well as the unitary (solid-body) catheter configurations described herein.

It is appreciated that other lumen size configurations can also be used in other embodiments. Indeed, in other embodiments narrowing of one or both lumens can occur proximal to the distal tip region, or only at the distal end thereof. In still other embodiments, no narrowing of the lumens through the distal tip region occurs.

The present invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

The invention claimed is:

1. A catheter for vascular insertion, comprising:
a catheter body defining at least a first lumen and a second lumen, the catheter body including a distal region, the distal region including:
an atraumatic nose portion defining a first distal opening in fluid communication with the first lumen and a second distal opening in fluid communication with the second lumen;
a first lateral opening defined by the catheter body and in fluid communication with the first lumen, and
a second lateral opening defined by the catheter body and in fluid communication with the second lumen,
wherein at least one of the first and second lateral openings is defined by an angle cross-cut through an outer perimeter of the catheter body.

2. The catheter as defined in claim 1, wherein at least one of the first and second lateral openings is defined by the catheter body so as to define a predetermined first angle with respect to a longitudinal axis of the catheter body and a predetermined second angle with respect to a plane coincident with the longitudinal axis that is coplanar with a septum separating the first and second lumens.

3. The catheter as defined in claim 1, wherein a cross sectional shape of at least one of the first lumen and the second lumen transitions at a transition region from a "D" shape to an oval shape.

4. The catheter as defined in claim 3, wherein the transition region is proximal to the first and second lateral openings.

5. The catheter as defined in claim 4, wherein the distal region is a unitary structure.

6. The catheter as defined in claim 1, wherein the first and second lateral openings are longitudinally staggered with respect to one another.

7. The catheter as defined in claim 1, wherein the nose portion is tapered, and wherein the first and second lateral openings are oppositely disposed on the catheter and are configured such that fluid exiting the catheter from the first lateral opening is imparted a flow direction that is substantially opposite in a radial direction and substantially similar in a longitudinal direction to fluid exiting the catheter from the second lateral opening.

8. The catheter as defined in claim 1, wherein the first and second lateral openings extend longitudinally and circumferentially about a portion of the catheter body.

9. The catheter as defined in claim 1, wherein the second lateral opening is substantially un-staggered in a longitudinal direction with respect to the first lateral opening.

10. The catheter as defined in claim 1, further including at least one side hole defined by the catheter body and in fluid communication with the second lumen, the at least one side hole being interposed longitudinally between the second distal opening and the second lateral opening.

11. A catheter for vascular insertion, comprising:
a catheter body defining at least a first lumen and a second lumen, the catheter body including a distal region, the distal region including:
a circumferentially convergent nose portion defining a first distal opening in fluid communication with the first lumen and a second distal opening in fluid communication with the second lumen;
a first lateral opening defined by the catheter body proximal to the nose portion and in fluid communication with the first lumen, and
a second lateral opening defined by the catheter body proximal to the nose portion and in fluid communication with the second lumen, wherein the second lateral opening is substantially un-staggered longitudinally with respect to the first lateral opening,
wherein the catheter is capable of a first staggered flow configuration wherein a majority of a first fluid portion exits the first lumen via the first distal opening and wherein simultaneously a majority of a second fluid portion enters the second lumen via the second lateral opening.

12. The catheter as defined in claim 11, wherein a portion of the first fluid portion exits the first lumen via the first lateral opening and a portion of the second fluid portion enters the second lumen via the second distal opening in the first staggered flow configuration.

13. The catheter as defined in claim 11, wherein the catheter is capable of a second staggered flow configuration wherein a majority of a first fluid portion enters the first lumen via the first lateral opening and wherein simultaneously a majority of a second fluid portion exits the second lumen via the second distal opening.

14. The catheter as defined in claim 13, wherein a portion of the first fluid portion enters the first lumen via the first distal opening and a portion of the second fluid portion exits the second lumen via the second lateral opening in the second staggered flow configuration.

15. The catheter as defined in claim 13, wherein the first distal opening is disposed proximal to the second distal opening on the nose portion, and wherein a first stagger distance of the first staggered flow configuration is less relative to a second stagger distance of the second staggered flow configuration.

16. The catheter as defined in claim 11, wherein the first and second fluid portions include blood of a patient when the catheter is disposed within a vessel of the patient during a hemodialysis procedure.

17. The catheter as defined in claim 11, wherein the second distal opening is continuous with the second lumen and is sized to receive a guidewire therethrough.

18. The catheter as defined in claim 11, wherein the first and second lateral openings are elongate and symmetrically opposed to one another.

19. A method for infusing and aspirating fluids with respect to a vessel of a patient via a catheter, the catheter including a catheter body defining a first lumen, a second lumen, and a distal region, the method comprising:
infusing a first fluid portion into the vessel via both a first distal opening defined by a circumferentially convergent nose portion of the catheter body and in fluid communication with the first lumen and a first lateral opening defined by the catheter body proximal to the nose portion and in fluid communication with the first lumen such that a majority of the first fluid portion exits the first lumen via the first distal opening; and simultaneously aspirating a second fluid portion from the vessel via both a second distal opening defined by the nose portion and in fluid communication with the second lumen and a second lateral opening defined by the catheter body proximal to the nose portion and in fluid communication with the second lumen such that a majority of the second fluid portion enters the catheter via the second lateral opening to provide a first staggered flow configuration between the first fluid portion and the second fluid portion.

20. The method for infusing and aspirating fluids as defined in claim 19, wherein the first lateral opening is substantially un-staggered in a longitudinal direction with respect to the second lateral opening.

* * * * *

UNITED STATES PATENT AND TRADEMARK OFFICE
CERTIFICATE OF CORRECTION

PATENT NO. : 8,292,841 B2  
APPLICATION NO. : 12/414467  
DATED : October 23, 2012  
INVENTOR(S) : Colin S. Gregersen Page 1 of 1

It is certified that error appears in the above-identified patent and that said Letters Patent is hereby corrected as shown below:

At Column 2, after line 34, please insert the following paragraphs:

--FIG. 5C is a side view of the distal region of the split-tip catheter of FIG. 1;

FIG. 5D is a cross sectional view of the catheter of FIG. 5C taken along the line 5D-5D;

FIG. 5E is a cross sectional view of the catheter of FIG. 5C taken along the line 5E-5E;

FIG. 5F is a cross sectional view of the catheter of FIG. 5C taken along the line 5F-5F;

FIG. 5G is a cross sectional view of the catheter of FIG. 5C taken along the line 5G-5G;

FIG. 5H is a distal end view of the catheter of FIG. 5C taken along the line 5H-5H;--

At Column 3, after line 15, please insert the following paragraphs:

--FIGS. 22A-22B are perspective views of a split-tip catheter including a distal region configured in accordance with one embodiment of the present invention;

FIGS. 23A-23C are perspective views of a split-tip catheter including a distal region configured in accordance with one embodiment of the present invention;--

Signed and Sealed this  
Twenty-second Day of January, 2013

David J. Kappos  
*Director of the United States Patent and Trademark Office*